United States Patent
Al-Murrani et al.

(10) Patent No.: US 9,476,868 B2
(45) Date of Patent: Oct. 25, 2016

(54) COMPOSITIONS AND METHODS FOR DIAGNOSING AND TREATING KIDNEY DISORDERS IN A CANINE

(75) Inventors: Samer Al-Murrani, Topeka, KS (US); Sukhaswami Malladi, Lawrence, KS (US); Xiangming Gao, Topeka, KS (US)

(73) Assignee: Hill's Pet Nutrition, Inc., Topeka, KS (US)

(*) Notice: Subject to any disclaimer, the term of this patent is extended or adjusted under 35 U.S.C. 154(b) by 0 days.

(21) Appl. No.: 13/519,048

(22) PCT Filed: Dec. 23, 2010

(86) PCT No.: PCT/US2010/062031
§ 371 (c)(1),
(2), (4) Date: Jun. 25, 2012

(87) PCT Pub. No.: WO2011/079280
PCT Pub. Date: Jun. 30, 2011

(65) Prior Publication Data
US 2012/0283129 A1 Nov. 8, 2012

Related U.S. Application Data

(60) Provisional application No. 61/289,773, filed on Dec. 23, 2009.

(51) Int. Cl.
C12Q 1/68 (2006.01)
G01N 33/53 (2006.01)
G01N 33/50 (2006.01)

(52) U.S. Cl.
CPC ............. *G01N 33/50* (2013.01); *C12Q 1/6883* (2013.01); *C12Q 2600/158* (2013.01); *G01N 2800/347* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 4,800,159 A | 1/1989 | Mullis et al. |
| 4,965,188 A | 10/1990 | Mullis et al. |
| 5,333,675 A | 8/1994 | Mullis et al. |
| 5,445,934 A | 8/1995 | Fodor et al. |
| 5,541,061 A | 7/1996 | Fodor et al. |
| 5,547,839 A | 8/1996 | Dower et al. |
| 5,677,195 A | 10/1997 | Winkler et al. |
| 5,744,305 A | 4/1998 | Fodor et al. |
| 5,770,722 A | 6/1998 | Lockhart et al. |
| 5,800,992 A | 9/1998 | Fodor et al. |
| 5,856,092 A | 1/1999 | Dale et al. |
| 5,858,659 A | 1/1999 | Sapolsky et al. |
| 5,902,723 A | 5/1999 | Dower et al. |
| 6,013,449 A | 1/2000 | Hacia et al. |
| 6,020,135 A | 2/2000 | Levine et al. |
| 6,033,860 A | 3/2000 | Lockhart et al. |
| 6,040,138 A | 3/2000 | Lockhart et al. |
| 6,040,193 A | 3/2000 | Winkler et al. |
| 6,156,501 A | 12/2000 | McGall et al. |
| 6,177,248 B1 | 1/2001 | Oliner et al. |
| 6,197,506 B1 | 3/2001 | Fodor et al. |
| 6,203,825 B1 | 3/2001 | Hodgkins |
| 6,284,460 B1 | 9/2001 | Fodor et al. |
| 6,300,063 B1 | 10/2001 | Lipshutz et al. |
| 6,300,070 B1 | 10/2001 | Boles et al. |
| 6,309,822 B1 | 10/2001 | Fodor et al. |
| 6,333,179 B1 | 12/2001 | Matsuzaki et al. |
| 6,368,799 B1 | 4/2002 | Chee |
| 7,300,652 B2 | 11/2007 | Bailly et al. |
| 7,482,135 B2 | 1/2009 | Ver Heijen et al. |
| 2002/0142284 A1 | 10/2002 | Raha et al. |
| 2003/0073100 A1 | 4/2003 | Peyman et al. |
| 2003/0087259 A1* | 5/2003 | Clancy et al. ............... 435/6 |
| 2004/0038856 A1 | 2/2004 | Chakravarty et al. |
| 2004/0101924 A1 | 5/2004 | Ver Heijen et al. |
| 2005/0032063 A1 | 2/2005 | Kopreski |
| 2005/0124534 A1 | 6/2005 | Noble et al. |
| 2006/0008804 A1 | 1/2006 | Chibout et al. |
| 2006/0240437 A1 | 10/2006 | Krolewski et al. |
| 2006/0253262 A1* | 11/2006 | Ching et al. ............... 702/20 |
| 2007/0015227 A1 | 1/2007 | Moses et al. |
| 2007/0243214 A1 | 10/2007 | Schiemann et al. |
| 2007/0254290 A1 | 11/2007 | Yen et al. |
| 2009/0117604 A1 | 5/2009 | Ver Heijen et al. |
| 2009/0203547 A1* | 8/2009 | Banes et al. ............... 506/16 |

FOREIGN PATENT DOCUMENTS

| | | |
|---|---|---|
| EP | 0985932 | 3/2000 |
| EP | 1808694 | 7/2007 |
| JP | S60-153762 A | 8/1985 |
| JP | H08-191668 A | 7/1996 |
| WO | WO 01/88544 | 11/2001 |
| WO | WO 2004/005544 | 1/2004 |
| WO | WO 2004/005934 | 1/2004 |

OTHER PUBLICATIONS

Greer et al in "Gene expression analysis in a canine model of X-linked Alport syndrome" (Mammalian Genome: 2006, vol. 17, pp. 976-990).*

(Continued)

*Primary Examiner* — Catherine S Hibbert

(57) ABSTRACT

The present invention provides methods for: diagnosing of, devising and monitoring a treatment plan for, and monitoring the status of a kidney disorder characterized by an abnormal loss of renal function, renal failure, reduced glomerular filtration rate or glomerulonephritis, in a canine, wherein the kidney disorder is detectable by utilizing at least one relevant biomarker isolated and measured from a biological test sample taken from such canine. The invention additionally relates to compositions, reagents and kits for carrying out the specified methods.

5 Claims, No Drawings

(56) References Cited

OTHER PUBLICATIONS

Quan Dissertation entitled "Expression Profile of Drug Absorption Related Genes in MDCK in Vitro Model" (Sep. 2008).*
Mody et al entitled "Decreased clearance of serum retinol-binding protein and elevated levels of transthyretin in insulin-resistant ob/ob mice" (Am J Physiol Endocrinol Metab 294: E785-E793, published Feb. 19, 2008).*
Neame et al (CMLS, Cell Mol Life Sci vol. 57 2000, pp. 859-863).*
Altschul et al., 1990, "Basic Local Alignment Search Tool", Journal of Molecular Biology 215(3):403-410.
Altschul et al., 1997 "Gapped BLAST and PS1-Blast: a New Generation of Protein Database Search Programs", Nucleic Acids Research 25(17):3389-3402.
Braun et al., 2002, "Plasma Cystatin C in the Dog: Reference Values and Variations with Renal Failure", Comparative Clinical Pathology 11(1):44-49.
Eckert et al., 1991, "DNA Polymerase Fidelity and the Polymerase Chain Reaction", PCR Methods & Applications 1:17-24.
Fan et al., 2005, "A Class of Models for Analyzing GeneChip®, Gene Expression Analysis Array Data", BMC Genomics 16:6-16.
Folli et al., 2001, "Identification, Retinoid Binding, and X-ray Analysis of a Human Retinol-binding Protein", Proceedings of the National Academy of Sciences 98(7):3710-3715.
Forterre et al., 2004, "Protein Profiling of Urine from Dogs with Renal Disease using ProteinChip Analysis",Journal of Veterinary Diagnostic Investigation 16(4):271-277.
Gerhard et al., 2004, "The Status, Quailty, and Expansion of the NIH Full-Length cDNA Project: The Mammalian Gene Collection (MGC)", Genome Research 14:2121-2127.
Hein et al., 2005, "BGX: a Fully Bayesian Integrated Approach to the Analysis of Affymetrix GeneChip Data", Biostatistics 6:349-373.
Ho et al., 2007, "Down-regulation of Retinol Binding Protein 5 is Associated with Aggressive Tumor Features in Hepatocellular Carcinoma", Journal of Cancer Research & Clinical Oncology 133(12):929-936.
Irizarry et al. 2003, "Exploration, Normalization, and Summaries of High Density Oligonucleotide Array Probe Level Data", Biostatistics 4:249-264.
Irizarry et al., 2003, "Summaries of Affymetrix GeneChip Probe Level Data", Nucleic Acid Research 31(4):e15.
Lee et al, 2006, "Secreted Frizzled Related Protein 2 (sFRP2) Decreases Susceptibility to UV-Induced Apoptosis in Primary Culture of Canine Mammary Gland Tumors by NF-κB Activation or JNK Suppression", Breast Cancer Research and Treatment 100(1):49-58.
Karlin et al., 1990, "Methods for Assessing the Statistical Significance of Molecular Sequence Features by Using General Scoring Schemes", Proceedings of the National Academy of Sciences 87:2264-2268.
Laterza et. al., 2002, "Cystatin C: An Improved Estimator of Glomerular Filtration Rate?",Clinical Chemistry 48:699-707.
Lenz et al., 1998, "Glomerular Endothelial Cell; Synthesize Collagens but Little Gelatinase A and B. ", Journal of American Society of Nephrology 9:2040-2047.
Lenz et al., 2000, "Matrix Metalloproteinases in Renal Development and Disease", Journal of American Society of Nephrology 11:574-581.
Li et al., 2001, "Model-based Analysis of Oligonucleotide Arrays: Expression Index Computation and Outlier Detection", Proceedings of the National Academy of Sciences 98(1):31-36.
Mattila et al., 1991, "Fidelity of DNA Synthesis by the Thermococcus Litoralis DNA Polymerase—an Extremely Heat Stable Enzyme with Proofreading Activity", Nucleic Acids Research 19(18):4967-4973.
Miyagawa et al., 2009, "Evaluation of the Measurement of Serum Cystatin C by an Enzyme-linked Immunosorbent Assay for Humans as a Marker of the Glomerular Filtration Rate in Dogs", Journal of Veterinary Medical Science 71(9):1169-1176.
Nagase et al., 1999, "Matrix Metalloproteinases", Journal of Biological Chemistry 274(31):21491-21494.
Newman, 2002, "Cystatin C", Annals of Clinical Biochemistry 39:89-104.
Nielsen et al., 1991, "Sequence-selective recognition of DNA by strand displacement with a thymine-substituted polyamide", Science 254;1497-1500.
Nielsen, 1999, "Applications of Peptide Nucleic Acids", Current Opinion in Biotechnology 10(1):71-75.
Onetti Muda et al.,1998, "Expression of TGF-beta Receptors Type I and II in Human Glomerulonephritis", Nephrology, dialysis, transplantation 13(2):279-284.
Paciello et al., 2008, "G.P.5.12 Decorin and lumican are differentially expressed in canine masticatory muscle myositis", Neuromuscular Disorders 18(9-10):772-773, abstract No. G.P.5.12.
PCT/US2010/062031—ISR and Written Opinion mailed Sep. 22, 2011.
PCT/US2010/062031—Written Opinion mailed Feb. 23, 2011.
Piantedosi et al., 2005, "Cellular Retinol-binding Protein Type III Is Needed for Retinoid Incorporation into Milk", Journal of Biological Chemistry 280(25):24286-24292.
Raila et al., 2000, "The Distribution of Vitamin A and Retinol-binding Protein in the Blood Plasma, Urine, Liver and Kidneys of Carnivores", Veterinary Research 31(6):541-551.
Sanders et al., 2004, "Renal Expression of Matrix Metalloproteinases in Human ANCA-associated Glomerulonephritis", Nephrology Dialysis Transplantation 19:1412-1419.
Sato et al., 2005, "Roles of Membrane-type Matrix Metalloproteinase-1 in Tumor Invasion and Metastasis", Cancer Science 96(4):212-217.
Schaefer et al., 2001, "Small Proteoglycans in Human Diabetic Nephropathy: Discrepancy Between Glomerular Expression and Protein Accumulation of Decorin, Biglycan, Lumican, and Fibromodulin", FASEB Journal, Published online.
Schaeffer et al., 2000, "Small Proteoglycans of Normal Adult Human Kidney: Distinct Expression Patterns of Decorin, Biglyean, Fibromodulin, and Lumican", Kidney International 58:1557-1568.
Schmidt et al., 2009, "Effect of Azotemia on Sserum N-terminal proBNP Concentration in Dogs with Normal Cardiac Function: A Pilot Study", Journal of Vetrinary Cardiology 11(supp 1):S81-S86.
Schwab et al., 2004, "Microarray Analysis of Focal Segmental Glomerulosclerosis", American Journal of Nephrology 24:438-447.
van Hoek et al., 2008, "Immunoassay of Urinary Retinol Binding Protein as Putatuive Renal Marker in Cats", Journal of Immunization Methods 329:208-213.
Werten et al., 2000, "Geeko t-crystallin: How Cellular Retinol-binding Protein Became an Eye Lens Ultraviolet Filter", Proceedings of the National Academy of Sciences 97(7):3282-3287.
Zheng, 1999, "Global Gene Expression Profiling on a Canine Modelof X-linked Alport Syndrome: Cross-species cDNA Microarray Analysis Provides Insight into the Early Molecular Alterations Associated with the Onset of this Progressive Renal Disease", Poser Presentation, abstract No. 480.
Zhou et al., 2005, "An Expression Index for Affymetrix GeneChips Based on the Generalized Logarithm", Bioinformatics 21(21):3983-3989.
U.S. Appl. No. 60/319,253, filed May 17, 2002 by Shoulian et al.
Almy et al., 2002, "Evaluation of cystatin C as an endogenous marker of glomerular filtration rate in dogs," J. Vet. Intern. Med. 16(1):45-51.
Clements et al., 2009, "Cartilage gene expression correlates with radiographic severity of canine elbow osteoarthritis," Vet. J. 179(2):211-218.
Hoffer et al., 1993, "The mouse apolipoprotein C1 gene: structure and expression," Genomics 18(1):37-42.
Kawakami et al., 2001, "Relationship between testicular transferrin and plasma estradiol-17beta concentrations of dogs with azoospermia and dogs with sertoli cell tumors," J. Vet. Med. Sci. 63(5):579-581.
Lee et al., 2004, "Secreted frizzled-related protein 2 (SFRP2) is highly expressed in canine mammary gland tumors but not in normal mammary glands," Breast Cancer Res. Treat. 84(2):139-149.

(56) References Cited

OTHER PUBLICATIONS

Maddens et al., 2010, "Validation of immunoassays for the candidate renal markers C-reactive protein, immunoglobulin G, thromboxane B2 and retinol binding protein in canine urine," Vet. Immunol. Immunopathol. 134(3-4):259-264.

Yokota et al., 2001, "High expression of 92 kDa type IV collagenase (matrix metalloproteinase-9) in canine mammary adenocarcinoma," Biochim. Biophys. Acta 1568(1):7-12.

Zheng et al., 2009, "Microarray identifies extensive downregulation of noncollagen extracellular matrix and profibrotic growth factor genes in chronic isolated mitral regurgitation in the dog," Circulation 119(15):2086-2095.

Tsuchiya et al, 2004, "Urinary protein analysis and renal mRNA expression in dogs with renal papillary necrosis induced by nefiracetam, a neurotransmission enhancer," J. Toxicol. Sci., 29(4):447 (P7-18).

Hellman, N., et al., 'Matrix metalloproteinase 13 (MMP13) and tissue inhibitor of matrix metalloproteinase 1 (TIMP1), regulated by the MAPK pathway, are both necessary for Madin-Darby canine kidney tubulogenesis', Journal of Biological Chemistry, 2008, vol. 283, No. 7, pp. 4272-4282.

Ojaimi, C., et al., 'Altered expression of a limited number of genes contributes to cardiac decompensation during chronic ventricular tachypacing in dogs', Physiological Genomics, 2007, vol. 29, No. 1, pp. 76-83.

Suematsu, N., et al., 'Hyperhomocysteinemia alters cardiac substrate metabolism by impairing nitric oxide bioavailability through oxidative stress', Circulation, 2007, vol. 115, No. 2, pp. 255-262.

\* cited by examiner

SEQUENCE LISTING

<160> NUMBER OF SEQ ID NOS: 22

<210> SEQ ID NO 1
<211> LENGTH: 338
<212> TYPE: PRT
<213> ORGANISM: Canis familiaris

<400> SEQUENCE: 1

```
Met Asn Leu Gly Val Phe Thr Leu Leu Ala Leu Ile Gly Gly Ala
1               5                   10                  15

Ser Gly Gln Tyr Tyr Asp Tyr Asp Phe Ser Leu Pro Ile Tyr Gly Leu
                20                  25                  30

Ser Ser Pro Asn Cys Ala Pro Glu Cys Asn Cys Pro Glu Ser Tyr Pro
            35                  40                  45

Ser Ala Met Tyr Cys Asp Glu Leu Lys Leu Lys Ser Val Pro Met Val
        50                  55                  60
```

```
Pro Pro Gly Ile Lys Tyr Leu Tyr Leu Arg Asn Asn Gln Ile Asp His
 65                  70                  75                  80

Ile Asp Glu Lys Ala Phe Glu Asn Val Thr Asp Leu Gln Trp Leu Ile
                 85                  90                  95

Leu Asp His Asn Leu Leu Glu Asn Ser Lys Ile Lys Gly Arg Ile Phe
            100                 105                 110

Ser Lys Leu Lys Gln Leu Lys Lys Leu His Ile Asn His Asn Asn Leu
        115                 120                 125

Thr Glu Ser Val Gly Pro Leu Pro Lys Ser Leu Val Asp Leu Gln Leu
    130                 135                 140

Thr His Asn Lys Ile Gln Lys Leu Gly Ser Phe Asp Gly Leu Val Asn
145                 150                 155                 160

Leu Thr Phe Val His Leu Gln His Asn Gln Leu Lys Glu Asp Thr Val
                165                 170                 175

Ser Ala Ala Phe Lys Gly Leu Lys Ser Leu Glu Tyr Leu Asp Leu Ser
            180                 185                 190

Tyr Asn Gln Met Ala Lys Leu Pro Ser Gly Leu Pro Ala Ser Leu Leu
        195                 200                 205

Thr Leu Tyr Leu Asp Asn Asn Lys Ile Ser Asn Ile Pro Asp Glu Tyr
    210                 215                 220

Phe Lys Arg Phe Asn Gly Leu Gln Tyr Leu Arg Leu Ser His Asn Glu
225                 230                 235                 240

Leu Ala Asp Ser Gly Val Pro Gly Asn Ser Phe Asn Val Ser Ser Leu
                245                 250                 255

Leu Glu Leu Asp Leu Ser Tyr Asn Lys Leu Lys Asn Ile Pro Thr Val
            260                 265                 270

Asn Glu Asn Leu Glu Asn Tyr Tyr Leu Glu Val Asn Glu Leu Glu Lys
        275                 280                 285

Phe Glu Val Lys Ser Phe Cys Lys Ile Leu Gly Pro Leu Ser Tyr Ser
    290                 295                 300

Lys Ile Lys His Leu Arg Leu Asp Gly Asn Arg Leu Thr His Thr Ser
305                 310                 315                 320

Leu Pro Pro Asp Met Tyr Glu Cys Leu Arg Val Ala Asn Glu Ile Thr
                325                 330                 335

Val Asn

<210> SEQ ID NO 2
<211> LENGTH: 1466
<212> TYPE: PRT
<213> ORGANISM: Canis familiaris

<400> SEQUENCE: 2

Met Thr Ser Phe Val Gln Lys Gly Thr Trp Leu Leu Leu Ala Leu Leu
  1               5                  10                  15

Gln Pro Ala Val Ile Ser Ala Gln Gln Ala Ile Asp Gly Gly Cys
                 20                  25                  30

Ser His Leu Gly Gln Ser Tyr Ala Asp Arg Asp Val Trp Lys Pro Glu
            35                  40                  45

Pro Cys Gln Ile Cys Val Cys Asp Ser Gly Ser Val Leu Cys Asp Asp
        50                  55                  60

Ile Ile Cys Asp Glu Gln Glu Leu Asp Cys Pro Asn Pro Glu Ile Pro
 65                  70                  75                  80

Phe Gly Glu Cys Cys Ala Val Cys Pro Gln Pro Pro Thr Ser Pro Pro
                 85                  90                  95
```

Arg Pro Pro Asn Gly His Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Pro Asn Tyr Ser Pro Gln Phe Glu Ser Tyr Asp
145                 150                 155                 160

Val Lys Ala Gly Val Ala Gly Gly Ile Gly Tyr Pro Gly Pro
                165                 170                 175

Ala Gly Pro Pro Gly Pro Pro Gly Pro Pro Gly Thr Ser Gly His Pro
        180                 185                 190

Gly Ser Pro Gly Ser Pro Gly Tyr Gln Gly Pro Pro Gly Glu Pro Gly
        195                 200                 205

Gln Ala Gly Pro Ala Gly Pro Pro Gly Pro Pro Gly Ala Met Gly Pro
    210                 215                 220

Ser Gly Pro Ala Gly Lys Asp Gly Glu Ser Gly Arg Pro Gly Arg Pro
225                 230                 235                 240

Gly Glu Arg Gly Leu Pro Gly Pro Pro Gly Met Lys Gly Pro Ala Gly
                245                 250                 255

Met Pro Gly Phe Pro Gly Met Lys Gly His Arg Gly Phe Asp Gly Arg
            260                 265                 270

Asn Gly Glu Lys Gly Asp Thr Gly Ala Pro Gly Leu Lys Gly Glu Asn
        275                 280                 285

Gly Leu Pro Gly Glu Asn Gly Ala Pro Gly Pro Met Gly Pro Arg Gly
    290                 295                 300

Ala Pro Gly Glu Arg Gly Arg Pro Gly Leu Pro Gly Ala Ala Gly Ala
305                 310                 315                 320

Arg Gly Asn Asp Gly Ala Arg Gly Ser Asp Gly Gln Pro Gly Pro Pro
                325                 330                 335

Gly Pro Pro Gly Thr Ala Gly Phe Pro Gly Ser Pro Gly Ala Lys Gly
            340                 345                 350

Glu Val Gly Pro Ala Gly Ser Pro Gly Ser Asn Gly Ser Pro Gly Gln
        355                 360                 365

Arg Gly Glu Pro Gly Pro Gln Gly His Ala Gly Ala Pro Gly Pro Pro
    370                 375                 380

Gly Pro Pro Gly Ser Asn Gly Ser Pro Gly Gly Lys Gly Glu Met Gly
385                 390                 395                 400

Pro Ala Gly Ile Pro Gly Ala Pro Gly Leu Ile Gly Ala Arg Gly Pro
                405                 410                 415

Pro Gly Pro Pro Gly Thr Asn Gly Ala Pro Gly Gln Arg Gly Gly Ala
            420                 425                 430

Gly Glu Pro Gly Lys Asn Gly Ala Lys Gly Glu Pro Gly Pro Arg Gly
        435                 440                 445

Glu Arg Gly Glu Ala Gly Ser Pro Gly Ile Pro Gly Pro Lys Gly Glu
    450                 455                 460

Asp Gly Lys Asp Gly Ser Pro Gly Glu Pro Gly Ala Asn Gly Leu Pro
465                 470                 475                 480

Gly Ala Ala Gly Glu Arg Gly Ala Pro Gly Phe Arg Gly Pro Ala Gly
                485                 490                 495

Ala Asn Gly Leu Pro Gly Glu Lys Gly Pro Ala Gly Glu Arg Gly Gly
            500                 505                 510

Pro Gly Pro Ala Gly Pro Arg Gly Ala Pro Gly Glu Pro Gly Arg Asp

-continued

```
            515                 520                 525
Gly Val Pro Gly Gly Pro Gly Met Arg Gly Met Pro Gly Ser Pro Gly
        530                 535                 540
Gly Pro Gly Ser Asp Gly Lys Pro Gly Pro Gly Ser Gln Gly Glu
545                 550                 555                 560
Ser Gly Arg Pro Gly Pro Gly Pro Ser Gly Pro Arg Gly Gln Pro
                565                 570                 575
Gly Val Met Gly Phe Pro Gly Pro Lys Gly Asn Asp Gly Ala Pro Gly
                580                 585                 590
Lys Asn Gly Glu Arg Gly Gly Pro Gly Gly Pro Gln Gly Pro
            595                 600                 605
Ala Gly Lys Asn Gly Glu Thr Gly Pro Gln Gly Pro Pro Gly Pro Thr
        610                 615                 620
Gly Pro Ala Gly Asp Lys Gly Asp Ala Gly Pro Pro Gly Pro Gln Gly
625                 630                 635                 640
Leu Gln Gly Leu Pro Gly Thr Ser Gly Pro Pro Gly Glu Asn Gly Lys
                645                 650                 655
Pro Gly Glu Pro Gly Pro Lys Gly Glu Ser Gly Ser Pro Gly Val Pro
            660                 665                 670
Gly Gly Lys Gly Asp Ser Gly Ala Pro Gly Glu Arg Gly Pro Pro Gly
        675                 680                 685
Ala Ala Gly Pro Met Gly Pro Arg Gly Ala Gly Pro Pro Gly Pro
        690                 695                 700
Glu Gly Gly Lys Gly Ala Ala Gly Pro Pro Gly Pro Pro Gly Ser Ala
705                 710                 715                 720
Gly Thr Pro Gly Leu Gln Gly Met Pro Gly Glu Arg Gly Gly Pro Gly
                725                 730                 735
Gly Pro Gly Pro Lys Gly Asp Lys Gly Glu Pro Gly Ser Ala Gly Ala
            740                 745                 750
Asp Gly Ala Pro Gly Lys Asp Gly Pro Arg Gly Pro Thr Gly Pro Ile
        755                 760                 765
Gly Pro Pro Gly Pro Ala Gly Gln Pro Gly Asp Lys Gly Glu Gly Gly
        770                 775                 780
Ala Pro Gly Leu Pro Gly Ile Ala Gly Pro Arg Gly Gly Pro Gly Glu
785                 790                 795                 800
Arg Gly Glu His Gly Pro Pro Gly Ala Gly Phe Pro Gly Ala Pro
                805                 810                 815
Gly Gln Asn Gly Glu Pro Gly Ala Lys Gly Glu Arg Gly Ala Pro Gly
            820                 825                 830
Glu Lys Gly Glu Gly Gly Pro Pro Gly Val Ala Gly Pro Pro Gly Gly
        835                 840                 845
Ala Gly Pro Ala Gly Pro Pro Gly Pro Gln Gly Val Lys Gly Glu Arg
        850                 855                 860
Gly Ser Pro Gly Gly Pro Gly Ala Ala Gly Phe Pro Gly Gly Arg Gly
865                 870                 875                 880
Leu Pro Gly Pro Pro Gly Asn Asn Gly Asn Pro Gly Pro Pro Gly Ser
                885                 890                 895
Ser Gly Ala Pro Gly Lys Asp Gly Pro Pro Gly Pro Pro Gly Asn Asn
            900                 905                 910
Gly Ala Pro Gly Ser Pro Gly Val Ser Gly Pro Lys Gly Asp Ala Gly
        915                 920                 925
Gln Pro Gly Glu Lys Gly Ser Pro Gly Pro Gln Gly Pro Pro Gly Ala
        930                 935                 940
```

```
Pro Gly Pro Leu Gly Ile Ala Gly Ile Thr Gly Ala Arg Gly Leu Ala
945                 950                 955                 960

Gly Pro Pro Gly Ile Pro Gly Pro Arg Gly Ser Pro Gly Pro Gln Gly
                965                 970                 975

Val Lys Gly Glu Asn Gly Lys Pro Gly Pro Ser Gly His Asn Gly Glu
            980                 985                 990

Arg Gly Pro Pro Gly Pro Gln Gly Leu Pro Gly Leu Ala Gly Thr Ala
        995                 1000                1005

Gly Glu Pro Gly Arg Asp Gly Asn Pro Gly Ser Asp Gly Leu Pro
    1010                1015                1020

Gly Arg Asp Gly Ala Pro Gly Gly Lys Gly Asp Arg Gly Glu Asn
    1025                1030                1035

Gly Ser Pro Gly Ala Pro Gly Ala Pro Gly His Pro Gly Pro Pro
    1040                1045                1050

Gly Pro Val Gly Pro Ala Gly Lys Ser Gly Asp Arg Gly Glu Thr
    1055                1060                1065

Gly Pro Ala Gly Pro Ser Gly Ala Pro Gly Pro Ala Gly Ser Arg
    1070                1075                1080

Gly Pro Pro Gly Pro Gln Gly Pro Arg Gly Asp Lys Gly Glu Thr
    1085                1090                1095

Gly Glu Arg Gly Leu Asn Gly Ile Lys Gly His Arg Gly Phe Pro
    1100                1105                1110

Gly Asn Pro Gly Ala Pro Gly Ser Pro Gly Pro Ala Gly His Gln
    1115                1120                1125

Gly Ala Ile Gly Ser Pro Gly Pro Ala Gly Pro Arg Gly Pro Val
    1130                1135                1140

Gly Pro Ser Gly Pro Pro Gly Lys Asp Gly Thr Ser Gly His Pro
    1145                1150                1155

Gly Pro Ile Gly Pro Pro Gly Pro Arg Gly Asn Arg Gly Glu Arg
    1160                1165                1170

Gly Ser Glu Gly Ser Pro Gly His Pro Gly Gln Pro Gly Pro Pro
    1175                1180                1185

Gly Pro Pro Gly Ala Pro Gly Pro Cys Cys Gly Gly Gly Ala Ala
    1190                1195                1200

Ala Leu Ala Ala Ala Gly Gly Glu Lys Ala Gly Gly Phe Ala Pro
    1205                1210                1215

Tyr Tyr Gly Asp Glu Pro Met Asp Phe Lys Ile Asn Thr Glu Glu
    1220                1225                1230

Ile Met Thr Ser Leu Lys Ser Val Ser Gly Gln Ile Glu Ser Leu
    1235                1240                1245

Val Ser Pro Asp Gly Ser Arg Lys His Pro Ala Arg Asn Cys Arg
    1250                1255                1260

Asp Leu Lys Phe Cys His Pro Glu Leu Lys Ser Gly Glu Tyr Trp
    1265                1270                1275

Val Asp Pro Asn Gln Gly Cys Lys Leu Asp Ala Ile Lys Val Phe
    1280                1285                1290

Cys Asn Met Glu Thr Gly Glu Thr Cys Leu Asn Ala Ser Pro Gly
    1295                1300                1305

Ser Val Pro Arg Lys Asn Trp Trp Thr Asp Ser Gly Ala Glu Lys
    1310                1315                1320

Lys His Val Trp Phe Gly Glu Ser Met Asp Gly Gly Phe Gln Phe
    1325                1330                1335
```

```
Gly Tyr Gly Asn Pro Glu Leu Pro Glu Asp Val Leu Asp Val Gln
    1340                1345                1350

Leu Ala Phe Leu Arg Leu Leu Ser Ser Arg Ala Ser Gln Asn Ile
    1355                1360                1365

Thr Tyr His Cys Lys Asn Ser Ile Ala Tyr Met Asp His Ala Ser
    1370                1375                1380

Gly Asn Val Lys Lys Ala Leu Arg Leu Met Gly Ser Asn Glu Gly
    1385                1390                1395

Glu Phe Lys Ala Glu Gly Asn Ser Lys Phe Thr Tyr Thr Val Leu
    1400                1405                1410

Glu Asp Gly Cys Thr Lys His Thr Gly Glu Trp Gly Lys Thr Val
    1415                1420                1425

Phe Glu Tyr Arg Thr Arg Lys Ala Val Arg Leu Pro Ile Ile Asp
    1430                1435                1440

Ile Ala Pro Tyr Asp Val Gly Gly Pro Asp Gln Glu Phe Gly Val
    1445                1450                1455

Asp Val Gly Pro Val Cys Phe Leu
    1460                1465

<210> SEQ ID NO 3
<211> LENGTH: 360
<212> TYPE: PRT
<213> ORGANISM: Canis familiaris

<400> SEQUENCE: 3

Met Lys Ala Thr Ile Ile Phe Leu Leu Leu Ala Gln Val Ser Trp Ala
1               5                   10                  15

Gly Pro Phe Gln Gln Arg Gly Leu Phe Asp Phe Met Leu Glu Asp Glu
                20                  25                  30

Ala Ser Gly Ile Gly Pro Glu Asp Arg Ala Pro Asp Met Pro Asp Leu
            35                  40                  45

Glu Leu Leu Gly Pro Val Cys Pro Phe Arg Cys Gln Cys His Leu Arg
        50                  55                  60

Val Val Gln Cys Ser Asp Leu Gly Leu Asp Lys Val Pro Lys Asp Leu
65                  70                  75                  80

Pro Pro Asp Thr Thr Leu Leu Asp Leu Gln Asn Asn Lys Ile Thr Glu
                85                  90                  95

Ile Lys Asp Gly Asp Phe Lys Asn Leu Lys Asn Leu His Thr Leu Ile
            100                 105                 110

Leu Val Asn Asn Lys Ile Ser Lys Ile Ser Pro Gly Ala Phe Thr Pro
        115                 120                 125

Leu Leu Lys Leu Glu Arg Leu Tyr Leu Ser Lys Asn His Leu Lys Glu
    130                 135                 140

Leu Pro Glu Lys Met Pro Lys Thr Leu Gln Glu Leu Arg Ala His Glu
145                 150                 155                 160

Asn Glu Ile Thr Lys Val Arg Lys Ala Val Phe Asn Gly Leu Asn Gln
                165                 170                 175

Met Ile Val Val Glu Leu Gly Thr Asn Pro Leu Lys Ser Ser Gly Ile
            180                 185                 190

Glu Asn Gly Ala Phe Gln Gly Met Lys Lys Leu Ser Tyr Ile Arg Ile
        195                 200                 205

Ala Asp Thr Asn Ile Thr Thr Ile Pro Gln Gly Leu Pro Pro Ser Leu
    210                 215                 220

Thr Glu Leu His Leu Glu Gly Asn Lys Ile Thr Lys Val Asp Ala Ser
225                 230                 235                 240
```

-continued

```
Ser Leu Lys Gly Leu Asn Asn Leu Ala Lys Leu Gly Leu Ser Phe Asn
            245                 250                 255

Ser Ile Ser Ala Val Asp Asn Gly Thr Leu Ala Asn Thr Pro His Leu
            260                 265                 270

Arg Glu Leu His Leu Asp Asn Asn Lys Leu Ile Arg Val Pro Gly Gly
            275                 280                 285

Leu Ala Glu His Lys Tyr Ile Gln Val Val Tyr Leu His Asn Asn Asn
            290                 295                 300

Ile Ser Ala Val Gly Ser Asn Asp Phe Cys Pro Pro Gly Tyr Asn Thr
305                 310                 315                 320

Lys Lys Ala Ser Tyr Ser Gly Val Ser Leu Phe Ser Asn Pro Val Gln
            325                 330                 335

Tyr Trp Glu Ile Gln Pro Ser Thr Phe Arg Cys Val Tyr Val Arg Ser
            340                 345                 350

Ala Ile Gln Leu Gly Asn Tyr Lys
            355                 360

<210> SEQ ID NO 4
<211> LENGTH: 294
<212> TYPE: PRT
<213> ORGANISM: Canis familiaris

<400> SEQUENCE: 4

Met Pro Arg Gly Pro Gly Ser Leu Leu Leu Val Leu Ala Ser His
1               5                   10                  15

Cys Cys Leu Gly Ser Ala Arg Gly Leu Phe Phe Gly Gln Pro Asp Phe
            20                  25                  30

Ser Tyr Lys Arg Ser Asn Cys Lys Pro Ile Pro Ala Asn Leu Gln Leu
            35                  40                  45

Cys His Gly Ile Glu Tyr Gln Asn Met Arg Leu Pro Asn Leu Leu Gly
        50                  55                  60

His Glu Thr Met Lys Glu Val Leu Glu Gln Ala Gly Ala Trp Ile Pro
65                  70                  75                  80

Leu Val Met Lys Gln Cys His Pro Asp Thr Lys Lys Phe Leu Cys Ser
            85                  90                  95

Leu Phe Ala Pro Val Cys Leu Asp Asp Leu Asp Glu Thr Ile Gln Pro
            100                 105                 110

Cys His Ser Leu Cys Val Gln Val Lys Asp Arg Cys Ala Pro Val Met
            115                 120                 125

Ser Ala Phe Gly Phe Pro Trp Pro Asp Met Leu Glu Cys Asp Arg Phe
130                 135                 140

Pro Gln Asp Asn Asp Leu Cys Ile Pro Leu Ala Ser Ser Asp His Leu
145                 150                 155                 160

Leu Pro Ala Thr Glu Glu Ala Pro Lys Val Cys Glu Ala Cys Lys Asn
            165                 170                 175

Lys Asn Glu Asp Asp Asn Asp Ile Met Glu Thr Leu Cys Lys Asn Asp
            180                 185                 190

Phe Ala Leu Lys Ile Lys Val Lys Glu Ile Thr Tyr Ile Asn Arg Asp
            195                 200                 205

Thr Lys Ile Ile Leu Glu Thr Lys Ser Lys Thr Ile Tyr Lys Leu Asn
            210                 215                 220

Gly Val Ser Glu Arg Asp Leu Lys Lys Ser Val Leu Trp Leu Lys Asp
225                 230                 235                 240

Ser Leu Gln Cys Thr Cys Glu Glu Met Asn Asp Ile Asn Ala Pro Tyr
```

```
                    245                 250                 255
Leu Val Met Gly Gln Lys Leu Gly Gly Glu Leu Val Ile Thr Ser Val
            260                 265                 270

Lys Arg Trp Gln Lys Gly Gln Arg Glu Phe Lys Arg Ile Ser Arg Ser
            275                 280                 285

Ile Arg Lys Leu Gln Cys
            290

<210> SEQ ID NO 5
<211> LENGTH: 978
<212> TYPE: PRT
<213> ORGANISM: Canis familiaris

<400> SEQUENCE: 5

Met Glu Ala Glu Val Trp Lys Val Glu His Val Thr Val Ala
1               5                   10                  15

Ser Lys Gln Arg Gln Arg His Phe Gln Gly Thr Ser Cys His Leu Glu
            20                  25                  30

Leu Gln Thr Met Glu Lys Met Leu Val Gly Cys Phe Leu Leu Val Leu
            35                  40                  45

Gly Gln Ile Leu Leu Val Leu Pro Ala Glu Ala Lys Glu Arg Thr Pro
        50                  55                  60

Trp Arg Ser Ile Ser Arg Gly Arg His Ala Trp Thr His Pro Gln Thr
65              70                  75                  80

Ala Leu Leu Glu Ser Ser Cys Glu Asn Lys Gln Ala Asp Leu Val Phe
                85                  90                  95

Ile Ile Asp Ser Ser Arg Ser Val Asn Thr His Asp Tyr Ala Lys Val
            100                 105                 110

Lys Glu Phe Ile Leu Asp Ile Leu Gln Phe Leu Asp Ile Ser Pro Asp
        115                 120                 125

Leu Thr Arg Val Gly Leu Leu Gln Tyr Gly Ser Thr Ile Lys Asn Glu
    130                 135                 140

Phe Ser Leu Lys Thr Phe Lys Lys Lys Ser Glu Val Glu Arg Ala Val
145                 150                 155                 160

Lys Arg Met Arg His Leu Ser Thr Gly Thr Met Thr Gly Leu Ala Ile
                165                 170                 175

Gln Tyr Ala Leu Asn Ile Ala Phe Ser Glu Ala Glu Gly Ala Arg Pro
            180                 185                 190

Leu Arg Glu Asn Val Leu Arg Val Ile Met Ile Val Thr Asp Gly Arg
        195                 200                 205

Pro Gln Asp Ser Val Ala Glu Val Ala Ala Lys Ala Arg Asp Thr Gly
    210                 215                 220

Ile Leu Ile Phe Ala Ile Gly Val Gly Gln Val Asp Leu Asn Thr Leu
225                 230                 235                 240

Lys Ala Ile Gly Ser Glu Pro His Glu Asp His Val Phe Leu Val Ala
                245                 250                 255

Asn Phe Ser Gln Met Glu Ser Leu Thr Ser Val Phe Gln Lys Lys Leu
            260                 265                 270

Cys Met Val His Met Cys Ser Val Leu Glu His Asn Cys Ala His Phe
            275                 280                 285

Cys Ile Asn Thr Pro Gly Ser Tyr Val Cys Arg Cys Lys Gln Gly Tyr
        290                 295                 300

Ile Leu Asn Ser Asp Gln Thr Thr Cys Arg Ile Gln Asp Leu Cys Ala
305                 310                 315                 320
```

```
Ala Lys Ala His Gly Cys Glu Gln Leu Cys Val Asn Val Leu Gly Ser
            325                 330                 335

Phe Val Cys Gln Cys Tyr Ser Gly Phe Thr Leu Ala Glu Asp Gly Lys
            340                 345                 350

Thr Cys Ala Ala Val Asp Tyr Cys Ala Ser Glu Asn His Gly Cys Glu
            355                 360                 365

His Glu Cys Val Asn Ala Asp Ser Ser Tyr Phe Cys Arg Cys Arg Lys
            370                 375                 380

Gly Phe Thr Leu Asn Pro Asp Lys Lys Thr Cys Ala Lys Ile Asp Tyr
385                 390                 395                 400

Cys Ala Ser Pro Asn Gln Gly Cys Gln His Glu Cys Val Asn Thr Asp
                    405                 410                 415

Asp Ser Tyr Ser Cys Arg Cys Leu Lys Gly Phe Thr Leu Asn Pro Asp
                420                 425                 430

Lys Lys Thr Cys Arg Arg Ile Asn Tyr Cys Ala Leu Asn Lys Pro Gly
            435                 440                 445

Cys Glu His Glu Cys Ile Asn Ile Glu Asp Gly Tyr Tyr Cys Arg Cys
            450                 455                 460

Arg Gln Gly Tyr Thr Leu Asp Pro Asn Gly Lys Thr Cys Ser Arg Val
465                 470                 475                 480

Asp His Cys Ala Glu Gln Asp His Gly Cys Glu Gln Leu Cys Leu Asn
                485                 490                 495

Thr Glu Asp Ser Tyr Val Cys Gln Cys Ser Glu Gly Phe Leu Ile Asn
                500                 505                 510

Asp Asp Leu Lys Thr Cys Ser Arg Ala Asp Tyr Cys Leu Leu Ser Asn
            515                 520                 525

His Gly Cys Glu Tyr Ser Cys Val Asn Thr Asp Arg Ser Phe Val Cys
            530                 535                 540

Arg Cys Pro Glu Gly Tyr Val Leu Arg Ser Asp Gly Lys Thr Cys Ala
545                 550                 555                 560

Lys Leu Asp Ser Cys Ala Val Gly Asp His Gly Cys Glu His Ser Cys
                565                 570                 575

Val Ser Ser Gly Asp Ser Phe Val Cys Gln Cys Phe Glu Gly Tyr Ile
                580                 585                 590

Leu Arg Glu Asp Gly Lys Thr Cys Arg Arg Lys Gly Val Cys Gln Ser
            595                 600                 605

Val Asn His Gly Cys Glu His Ile Cys Val Asn Ser Asp Glu Ser Tyr
            610                 615                 620

Ile Cys Lys Cys Arg Glu Gly Phe Arg Leu Ala Glu Asp Gly Lys Arg
625                 630                 635                 640

Cys Arg Arg Lys Asp Val Cys Lys Ser Thr Tyr His Gly Cys Glu His
                645                 650                 655

Ile Cys Val Asn His Gly Asn Ser Tyr Ile Cys Lys Cys Ser Glu Gly
                660                 665                 670

Phe Val Leu Ala Glu Asp Gly Lys Arg Cys Lys Arg Cys Thr Glu Gly
            675                 680                 685

Pro Leu Asp Leu Val Phe Val Ile Asp Gly Ser Lys Ser Leu Gly Glu
            690                 695                 700

Glu Asn Phe Glu Ile Val Lys Gln Phe Val Ala Gly Ile Ile Asp Ser
705                 710                 715                 720

Leu Ala Val Ser Pro Lys Ala Ala Arg Val Gly Leu Leu Gln Tyr Ser
                725                 730                 735

Thr Gln Val Arg Thr Glu Phe Thr Leu Gly Asp Phe Ser Ser Ala Arg
```

```
                      740                 745                 750
Asp Met Lys Lys Ala Val Ala His Met Lys Tyr Met Gly Lys Gly Ser
            755                 760                 765
Met Thr Gly Leu Ala Leu Lys His Met Phe Glu Arg Ser Phe Asn Pro
        770                 775                 780
Val Glu Gly Ala Arg Pro Val Ser Pro Gly Val Ser Arg Val Ala Ile
785                 790                 795                 800
Val Phe Thr Asp Gly Arg Ala Gln Asp Val Ser Ala Trp Ala Arg
                805                 810                 815
Arg Ala Arg Ala Gly Gly Ile Thr Met Tyr Ala Val Gly Val Gly Lys
            820                 825                 830
Ala Ile Glu Glu Glu Leu Gln Glu Ile Ala Ser Glu Pro Thr Asp Lys
            835                 840                 845
His Leu Phe Tyr Ala Glu Asp Phe Ser Thr Met Gly Glu Ile Ser Glu
        850                 855                 860
Lys Leu Lys Lys Gly Ile Cys Glu Ala Leu Glu Asp Ser Asp Gly Ser
865                 870                 875                 880
Gln Asp Ser Pro Ala Gly Glu Leu Pro Lys Arg Val His Gln Pro Thr
                885                 890                 895
Glu Ser Glu Pro Val Thr Ile Asn Ile Arg Asp Leu Leu Ser Cys Ser
            900                 905                 910
Asn Phe Ala Val Gln His Arg Tyr Leu Phe Glu Glu Asp Ser Val Ser
            915                 920                 925
Arg Ser Thr Gln Lys Leu Phe His Ser Thr Lys Ser Ser Gly Ser Pro
        930                 935                 940
Leu Glu Glu Lys His Asp Gln Cys Lys Cys Glu Asn Leu Ile Met Phe
945                 950                 955                 960
Gln Asn Leu Ala Asn Glu Glu Val Arg Lys Leu Thr Gln Arg Tyr Ile
                965                 970                 975
Leu Phe

<210> SEQ ID NO 6
<211> LENGTH: 267
<212> TYPE: PRT
<213> ORGANISM: Canis familiaris

<400> SEQUENCE: 6

Met Gln Val Leu Ala Ala Gly Arg Arg Leu Pro Ser Val Phe His Pro
1               5                   10                  15
Gly Arg Tyr Glu Ser Glu Thr Pro Ser Arg Pro Gly Tyr Lys Ala Gly
            20                  25                  30
Gly Pro Ala Ala Pro Ala Asp Arg Arg Leu Pro Trp Leu His Ala Arg
        35                  40                  45
Pro Ala Pro Arg Pro Gly Leu Arg Ala Ala Pro Val Gly Gly Leu Pro
    50                  55                  60
Gly Thr Met Glu Trp Val Trp Ala Leu Val Leu Leu Ala Ala Leu Gly
65                  70                  75                  80
Ser Ala Arg Ala Glu Ser Asp Cys Arg Val Ser Asn Phe Gln Val Lys
                85                  90                  95
Lys Asn Phe Asp Lys Ala Arg Phe Ala Gly Thr Trp Tyr Ala Met Ala
            100                 105                 110
Lys Lys Asp Pro Glu Gly Leu Phe Leu Gln Asp Asn Ile Val Ala Glu
            115                 120                 125
Phe Ser Val Asp Glu Asn Gly Arg Met Ser Ala Thr Ala Lys Gly Arg
```

```
            130                 135                 140
Val Arg Leu Leu Asn Asn Trp Asp Val Cys Ala Asp Met Val Gly Thr
145                 150                 155                 160

Phe Thr Asp Thr Glu Asp Pro Ala Lys Phe Lys Met Lys Tyr Trp Gly
                165                 170                 175

Val Ala Ser Phe Leu Gln Lys Gly Asn Asp Asp His Trp Ile Ile Asp
            180                 185                 190

Thr Asp Tyr Asp Thr Tyr Ala Val Gln Tyr Ser Cys Arg Leu Leu Asn
        195                 200                 205

Leu Asp Gly Thr Cys Ala Asp Ser Tyr Ser Phe Val Phe Ser Arg Asp
    210                 215                 220

Pro Asn Gly Leu Pro Leu Glu Ala Gln Lys Ile Val Arg Gln Arg Gln
225                 230                 235                 240

Glu Glu Leu Cys Leu Ala Arg Gln Tyr Arg Leu Ile Val His Asn Gly
                245                 250                 255

Tyr Cys Asp Gly Arg Ser Glu Pro Asn Thr Leu
            260                 265

<210> SEQ ID NO 7
<211> LENGTH: 704
<212> TYPE: PRT
<213> ORGANISM: Canis familiaris

<400> SEQUENCE: 7

Met Ser Pro Arg Gln Pro Leu Val Leu Val Phe Leu Val Leu Gly Cys
1               5                   10                  15

Cys Ser Ala Ala Pro Arg Pro His Lys Pro Thr Val Val Phe Pro
            20                  25                  30

Gly Asp Leu Arg Thr Asn Leu Thr Asp Lys Gln Leu Ala Glu Glu Tyr
        35                  40                  45

Leu Phe Arg Tyr Gly Tyr Thr Gln Val Ala Glu Leu Ser Asp Asp Lys
    50                  55                  60

Gln Ser Leu Ser Arg Gly Leu Arg Leu Leu Gln Arg Arg Leu Ala Leu
65                  70                  75                  80

Pro Glu Thr Gly Glu Leu Asp Lys Thr Thr Leu Glu Ala Met Arg Ala
                85                  90                  95

Pro Arg Cys Gly Val Pro Asp Leu Gly Lys Phe Gln Thr Phe Glu Gly
            100                 105                 110

Asp Leu Lys Trp His His Asn Asp Ile Thr Tyr Trp Ile Gln Asn Tyr
        115                 120                 125

Ser Glu Asp Leu Pro Arg Asp Val Ile Asp Asp Ala Phe Ala Arg Ala
    130                 135                 140

Phe Ala Val Trp Ser Ala Val Thr Pro Leu Thr Phe Thr Arg Val Tyr
145                 150                 155                 160

Gly Pro Glu Ala Asp Ile Ile Ile Gln Phe Gly Val Arg Glu His Gly
                165                 170                 175

Asp Gly Tyr Pro Phe Asp Gly Lys Asn Gly Leu Leu Ala His Ala Phe
            180                 185                 190

Pro Pro Gly Pro Gly Ile Gln Gly Asp Ala His Phe Asp Asp Glu Glu
        195                 200                 205

Leu Trp Thr Leu Gly Lys Gly Val Val Val Pro Thr His Phe Gly Asn
    210                 215                 220

Ala Asp Gly Ala Pro Cys His Phe Pro Phe Thr Phe Glu Gly Arg Ser
225                 230                 235                 240
```

-continued

```
Tyr Ser Ala Cys Thr Thr Asp Gly Arg Ser Asp Thr Pro Trp Cys
                245                 250                 255

Ser Thr Thr Ala Asp Tyr Asp Thr Asp Arg Arg Phe Gly Phe Cys Pro
            260                 265                 270

Ser Glu Lys Leu Tyr Thr Gln Asp Gly Asn Gly Asp Gly Lys Pro Cys
        275                 280                 285

Val Phe Pro Phe Thr Phe Glu Gly Arg Ser Tyr Ser Thr Cys Thr Thr
    290                 295                 300

Asp Gly Arg Ser Asp Gly Tyr Arg Trp Cys Ser Thr Thr Gly Asp Tyr
305                 310                 315                 320

Asp Gln Asp Lys Leu Tyr Gly Phe Cys Pro Thr Arg Val Asp Ser Ala
                325                 330                 335

Val Thr Gly Gly Asn Ser Ala Gly Glu Pro Cys Val Phe Pro Phe Ile
            340                 345                 350

Phe Leu Gly Lys Gln Tyr Ser Thr Cys Thr Arg Glu Gly Arg Gly Asp
        355                 360                 365

Gly His Leu Trp Cys Ala Thr Thr Ser Asn Phe Asp Arg Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Ser Phe Thr Glu Gly Pro Pro Leu His
            420                 425                 430

Glu Asp Asp Val Arg Gly Ile Gln His Leu Tyr Gly Pro Arg Pro Glu
        435                 440                 445

Pro Glu Pro Gln Pro Pro Thr Ala Pro Pro Thr Ala Pro Pro Thr Val
    450                 455                 460

Cys Ala Thr Gly Pro Pro Thr Thr Arg Pro Ser Glu Arg Pro Thr Ala
465                 470                 475                 480

Gly Pro Thr Gly Pro Pro Ala Ala Gly Pro Thr Gly Pro Pro Thr Ala
                485                 490                 495

Gly Pro Ser Glu Ala Pro Thr Val Pro Val Asp Pro Ala Glu Asp Ile
            500                 505                 510

Cys Lys Val Asn Ile Phe Asp Ala Ile Ala Glu Ile Arg Asn Tyr Leu
        515                 520                 525

His Phe Phe Lys Glu Gly Lys Tyr Trp Arg Phe Ser Lys Gly Lys Gly
    530                 535                 540

Arg Arg Val Gln Gly Pro Phe Leu Ile Thr Asp Thr Trp Pro Ala Leu
545                 550                 555                 560

Pro Arg Lys Leu Asp Ser Ala Phe Glu Asp Gly Leu Thr Lys Lys Thr
                565                 570                 575

Phe Phe Phe Ser Gly Arg Gln Val Trp Val Tyr Thr Gly Thr Ser Val
            580                 585                 590

Val Gly Pro Arg Arg Leu Asp Lys Leu Gly Leu Gly Pro Glu Val Thr
        595                 600                 605

Gln Val Thr Gly Ala Leu Pro Gln Gly Gly Gly Lys Val Leu Leu Phe
    610                 615                 620

Ser Arg Gln Arg Phe Trp Ser Phe Asp Val Lys Thr Gln Thr Val Asp
625                 630                 635                 640

Pro Arg Ser Ala Gly Ser Val Glu Gln Met Tyr Pro Gly Val Pro Leu
                645                 650                 655

Asn Thr His Asp Ile Phe Gln Tyr Gln Glu Lys Ala Tyr Phe Cys Gln
```

```
                    660                 665                 670
Asp Arg Phe Tyr Trp Arg Val Asn Ser Arg Asn Glu Val Asn Gln Val
            675                 680                 685

Asp Glu Val Gly Tyr Val Thr Phe Asp Ile Leu Gln Cys Pro Glu Asp
        690                 695                 700

<210> SEQ ID NO 8
<211> LENGTH: 445
<212> TYPE: PRT
<213> ORGANISM: Canis familiaris

<400> SEQUENCE: 8

Met Met Lys Thr Leu Leu Leu Val Gly Leu Leu Leu Thr Trp Asp
1               5                   10                  15

Asn Gly Arg Val Leu Gly Asp Gln Ala Val Ser Asp Thr Glu Leu Gln
            20                  25                  30

Glu Met Ser Thr Glu Gly Ser Lys Tyr Ile Asn Lys Glu Ile Lys Asn
        35                  40                  45

Ala Leu Lys Gly Val Lys Gln Ile Lys Thr Leu Ile Glu Gln Thr Asn
    50                  55                  60

Glu Glu Arg Lys Ser Leu Leu Ser Asn Leu Glu Glu Ala Lys Lys Lys
65                  70                  75                  80

Lys Glu Asp Ala Leu Asn Asp Thr Lys Asp Ser Glu Thr Lys Leu Lys
                85                  90                  95

Ala Ser Gln Gly Val Cys Asn Asp Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly His Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Ala Leu Asp Val Met
                165                 170                 175

Gln Asp Ser Phe Asn Arg Ala Ser Ser Ile Met Asp Glu Leu Phe Gln
            180                 185                 190

Asp Arg Phe Phe Thr Arg Glu Pro Gln Asp Thr Tyr His Tyr Ser Pro
        195                 200                 205

Phe Ser Leu Phe Gln Arg Arg Pro Phe Phe Asn Pro Lys Phe Arg Ile
    210                 215                 220

Ala Arg Asn Ile Ile Pro Phe Pro Arg Phe Gln Pro Leu Asn Phe His
225                 230                 235                 240

Asp Met Phe Gln Pro Phe Phe Asp Met Ile His Gln Ala Gln Gln Ala
                245                 250                 255

Met Asp Val Asn Leu His Arg Ile Pro Tyr His Phe Pro Ile Glu Phe
            260                 265                 270

Pro Glu Glu Asp Asn Arg Thr Val Cys Lys Glu Ile Arg His Asn Ser
        275                 280                 285

Thr Gly Cys Leu Lys Met Lys Asp Gln Cys Glu Lys Cys Gln Glu Ile
    290                 295                 300

Leu Ser Val Asp Cys Ser Ser Asn Pro Ala Gln Val Gln Leu Arg
305                 310                 315                 320

Gln Glu Leu Ser Asn Ser Leu Gln Ile Ala Glu Lys Phe Thr Lys Leu
                325                 330                 335
```

```
Tyr Asp Glu Leu Leu Gln Ser Tyr Gln Lys Met Phe Asn Thr Ser
                340                 345                 350

Ser Leu Leu Lys Gln Leu Asn Glu Gln Phe Ser Trp Val Ser Gln Leu
355                 360                 365

Ala Asn Leu Thr Gln Ser Glu Asp Pro Phe Tyr Leu Gln Val Thr Thr
        370                 375                 380

Val Gly Ser Gln Thr Ser Asp Ser Asn Val Pro Val Gly Phe Thr Lys
385                 390                 395                 400

Val Val Val Lys Leu Phe Asp Ser Asp Pro Ile Thr Val Met Ile Pro
                405                 410                 415

Glu Ala Val Ser Arg Asn Asn Pro Lys Phe Met Glu Thr Val Ala Glu
                420                 425                 430

Lys Ala Leu Gln Glu Tyr Arg Gln Lys His Arg Glu Glu
            435                 440                 445

<210> SEQ ID NO 9
<211> LENGTH: 705
<212> TYPE: PRT
<213> ORGANISM: Canis familiaris

<400> SEQUENCE: 9

Met Arg Leu Ala Val Arg Ala Leu Leu Ala Cys Ala Val Leu Gly Leu
1               5                   10                  15

Cys Leu Ala Val Ser Pro Glu Lys Thr Val Arg Trp Cys Thr Val Ser
                20                  25                  30

Asn His Glu Ala Ser Lys Cys Ser Ser Phe Met Glu Asn Met Lys Thr
            35                  40                  45

Val Leu Glu Asn Gly Pro Phe Val Ser Cys Val Lys Arg Thr Ser Tyr
        50                  55                  60

Leu Glu Cys Ile Lys Ala Ile Trp Ala Asn Glu Ala Asp Ala Val Thr
65                  70                  75                  80

Leu Asp Ala Gly Leu Val Phe Glu Ala Gly Leu Asn Pro Tyr Asn Leu
                85                  90                  95

Lys Pro Val Val Ala Glu Phe Tyr Gly Lys Asp Lys Gln Thr Arg Tyr
                100                 105                 110

Tyr Ala Val Ala Val Val Lys Lys Ser Ser Thr Phe Asn Leu Asn Gln
            115                 120                 125

Leu Gln Gly Lys Lys Ser Cys His Thr Gly Leu Gly Arg Ser Ala Gly
        130                 135                 140

Trp Asn Ile Pro Met Gly Leu Leu Tyr Trp Lys Leu Pro Glu Pro Arg
145                 150                 155                 160

Glu Ser Leu Gln Lys Ala Ala Ser Ser Phe Phe Thr Ala Ser Cys Val
                165                 170                 175

Pro Cys Val Asp Arg Thr Ala Phe Pro Lys Leu Cys Gln Leu Cys Val
                180                 185                 190

Gly Lys Gly Thr Asp Lys Cys Ala Cys Ser Asn His Glu Pro Tyr Phe
            195                 200                 205

Gly Tyr Ser Gly Ala Phe Lys Cys Leu Met Glu Asp Ala Gly Glu Val
        210                 215                 220

Ala Phe Val Lys His Ser Thr Val Leu Glu Asn Leu Pro Asn Lys Ala
225                 230                 235                 240

Asp Leu Asp Gln Tyr Glu Leu Leu Cys Pro Asp Asn Lys Arg Lys Pro
                245                 250                 255

Val Gly Glu Tyr Lys Gln Cys Tyr Leu Ala Lys Val Pro Ser His Ala
                260                 265                 270
```

```
Val Val Ala Arg Ser Val Gly Gly Lys Glu Asp Leu Ile Trp Glu Leu
        275                 280                 285

Leu Asn Gln Ala Gln Glu His Tyr Gly Lys Asp Lys Ser Lys Val Phe
    290                 295                 300

Gln Leu Phe Ser Ser Thr Leu Gly Lys Asp Leu Leu Phe Lys Asp Ser
305                 310                 315                 320

Ala Glu Gly Phe Phe Arg Ile Pro Pro Lys Met Asp Thr Trp Leu Tyr
                325                 330                 335

Leu Gly Tyr Glu Tyr Val Thr Ala Leu Arg Asn Leu Arg Glu Asp Val
                340                 345                 350

Arg Pro Asp Thr Pro Arg Asp Glu Cys Lys Lys Val Lys Trp Cys Ala
                355                 360                 365

Val Gly His His Glu Ile Ala Lys Cys Asp Glu Trp Ser Val Asn Ser
    370                 375                 380

Glu Gly Lys Ile Glu Cys Glu Ser Ala Glu Ser Thr Glu Asp Cys Ile
385                 390                 395                 400

Ala Lys Ile Ala Lys Gly Glu Ala Asp Ala Met Ser Leu Asp Gly Gly
                405                 410                 415

Tyr Ile Tyr Ile Ala Gly Gln Cys Gly Leu Val Pro Val Leu Ala Glu
                420                 425                 430

Asn Tyr Lys Thr Gln Gly Ser Thr Cys Ser Asn Thr Ala Glu Glu Gly
            435                 440                 445

Tyr Leu Ala Val Ala Val Val Lys Arg Leu Asp Lys Thr Ile Ser Trp
    450                 455                 460

Asn Asn Leu Gln Gly Lys Lys Ser Cys His Thr Ala Val Asp Arg Thr
465                 470                 475                 480

Ala Gly Trp Asn Ile Pro Met Gly Leu Leu Tyr Asn Arg Ile Asn His
                485                 490                 495

Cys Glu Phe Asp Lys Phe Phe Ser Gln Gly Cys Ala Pro Gly Ser Met
                500                 505                 510

Arg Asn Ser Ser Leu Cys Ala Leu Cys Ile Gly Ser Ala Asn Val Pro
            515                 520                 525

Gly Lys Glu Cys Val Pro Asn Asn His Glu Arg Tyr Tyr Gly Tyr Thr
    530                 535                 540

Gly Ala Phe Arg Cys Leu Val Glu Lys Gly Asp Val Ala Phe Val Lys
545                 550                 555                 560

Asp Gln Thr Val Leu Gln Asn Thr Gly Gly Lys Asn Thr Glu Asp Trp
                565                 570                 575

Ala Lys Asp Leu Lys Glu Glu Asp Phe Glu Leu Leu Cys Pro Asp Gly
                580                 585                 590

Gln Arg Lys Ser Val Asp Lys Ala Pro Glu Cys Phe Leu Ala Lys Ala
            595                 600                 605

Pro Asn His Ala Val Val Ser Arg Lys Asp Lys Ala Ser Cys Val Ser
    610                 615                 620

Lys Met Leu Leu Asp Gln Gln Leu Leu Phe Gly Arg Asn Gly Asn Asp
625                 630                 635                 640

Cys Ser Gly Lys Phe Cys Leu Phe His Ser Ala Thr Lys Asp Leu Leu
                645                 650                 655

Phe Arg Asp Asp Thr Gln Cys Leu Ala Lys Leu Pro Glu Asp Thr Thr
                660                 665                 670

Tyr Lys Ser Tyr Leu Gly Ala Glu Tyr Ile Thr Ala Val Ala Asn Leu
            675                 680                 685
```

```
Arg Gln Cys Ser Thr Ser Lys Leu Leu Glu Ala Cys Thr Phe His Thr
    690                 695                 700

Ser
705
```

<210> SEQ ID NO 10
<211> LENGTH: 88
<212> TYPE: PRT
<213> ORGANISM: Canis familiaris

<400> SEQUENCE: 10

```
Met Arg Leu Ile Leu Ser Leu Pro Val Leu Val Val Leu Ser Met
1               5                   10                  15

Val Leu Glu Gly Pro Ala Pro Ala Gln Ala Ala Gly Glu Ile Ser Ser
            20                  25                  30

Thr Phe Glu Arg Ile Pro Asp Lys Leu Lys Glu Phe Gly Asn Thr Leu
        35                  40                  45

Glu Asp Lys Ala Arg Ala Ala Ile Glu Ser Ile Lys Lys Ser Asp Ile
50                  55                  60

Pro Ala Lys Thr Arg Asn Trp Phe Ser Glu Ala Phe Lys Lys Val Lys
65                  70                  75                  80

Glu His Leu Lys Thr Ala Phe Ser
                85
```

<210> SEQ ID NO 11
<211> LENGTH: 424
<212> TYPE: PRT
<213> ORGANISM: Canis familiaris

<400> SEQUENCE: 11

```
Met Pro Leu Leu Trp Leu Arg Gly Phe Leu Val Ala Ser Cys Trp Ile
1               5                   10                  15

Ile Val Arg Ser Ser Pro Thr Pro Gly Pro Glu Gly Pro Gly Ala Ala
            20                  25                  30

Pro Ala Cys Pro Ala Cys Ala Leu Thr Ala Leu Pro Arg Asp Ala Pro
        35                  40                  45

Asn Ser Gln Pro Glu Met Val Glu Ala Val Lys Lys His Ile Leu Asn
50                  55                  60

Met Leu His Leu Lys Lys Arg Pro Glu Val Thr Gln Pro Val Pro Lys
65                  70                  75                  80

Ala Ala Leu Leu Asn Ala Ile Arg Lys Leu His Val Gly Lys Val Gly
            85                  90                  95

Glu Asn Gly Phe Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Leu
            165                 170                 175

Gln Lys His Pro Gln Gly Ser Leu Asp Ala Gly Glu Glu Ala Glu Asp
        180                 185                 190

Met Gly Phe Pro Glu Glu Arg Asn Glu Val Leu Ile Ser Glu Lys Val
        195                 200                 205
```

```
Val Asp Ala Arg Lys Ser Thr Trp His Ile Phe Pro Val Ser Ser Ser
210                 215                 220

Ile Gln Arg Leu Leu Asp Gln Gly Arg Ser Ser Leu Asp Val Arg Ile
225                 230                 235                 240

Ala Cys Glu Gln Cys His Glu Thr Gly Ala Ser Leu Val Leu Leu Gly
                245                 250                 255

Lys Lys Lys Lys Lys Glu Glu Glu Gly Glu Gly Lys Lys Lys Asp Gly
                260                 265                 270

Gly Asp Ala Gly Ala Gly Gly Asp Glu Asp Lys Glu Gln Ser His Arg
                275                 280                 285

Pro Phe Leu Met Leu Gln Ala Arg Gln Ser Glu Asp His Pro His Arg
290                 295                 300

Arg Arg Arg Arg Gly Leu Glu Cys Asp Gly Lys Val Asn Ile Cys Cys
305                 310                 315                 320

Lys Lys Gln Phe Phe Val Ser Phe Lys Asp Ile Gly Trp Asn Asp Trp
                325                 330                 335

Ile Ile Ala Pro Ser Gly Tyr His Ala Asn Tyr Cys Glu Gly Gly Cys
                340                 345                 350

Pro Ser His Ile Ala Gly Thr Ser Gly Ser Ser Leu Ser Phe His Ser
                355                 360                 365

Thr Val Ile Asn His Tyr Arg Leu Arg Gly His Ser Pro Phe Thr Asn
370                 375                 380

Leu Lys Ser Cys Cys Val Pro Thr Lys Leu Arg Pro Met Ser Met Leu
385                 390                 395                 400

Tyr Tyr Asp Asp Gly Gln Asn Ile Ile Lys Lys Asp Ile Gln Asn Met
                405                 410                 415

Ile Val Glu Glu Cys Gly Cys Ser
                420

<210> SEQ ID NO 12
<211> LENGTH: 2028
<212> TYPE: DNA
<213> ORGANISM: Canis familiaris

<400> SEQUENCE: 12
agctagagta tttggactag ttaagcatga atctctctcc cattccatag ggaatgagct      60
gggcagtcct tcctccccac gtccacctgc acttcgttag agagcagaat gctcacatgc     120
caccccacaa gatccccaca gtgacataac tccatgcaga gactggcgtg actgggctgg     180
gtttcccccc cttcagctct tgtatcacta agaatctggc agccagttcc gtcctgacag     240
agttcacagc atatattggt ggattcttgt ccatagtgca tctgctttaa gaattaacga     300
aagcagtgtc aagacagaag gattcaaagc atttgccaaa aatgaatcta ggtgtgttta     360
ctctactctt ggcattaatt ggtggtgcca gcggccagta ctatgattac gatttctccc     420
taccgattta tgggctgtca tcaccaaact gtgcaccaga atgtaactgc cctgaaagct     480
acccatcggc catgtactgc gatgagctga aattgaaaag tgtaccaatg gtgcctcctg     540
gaatcaagta tctttacctt aggaataacc agatcgacca tattgatgaa aaggcctttg     600
aaaacgtaac tgacctgcag tggctcattc tggatcataa ccttctagaa aattccaaga     660
ttaaaggaag aatttttctct aaactgaaac aactgaagaa gctgcatata aatcacaaca     720
acctgacaga gtctgtgggc ccgcttccca atctctggt ggacctgcag cttacacaca     780
acaagatcca gaagctgggc tccttcgatg gactggtaaa cctgaccttt gtccaccttc     840
aacacaatca gctgaaagag gatactgtgt cagctgcttt taaggtctt aagtccctcg     900
```

```
agtaccttga cttgagctac aatcagatgg ccaaactgcc ttctggtctc ccagcatctc     960
ttctgactct ctacttggac aacaataaga tcagcaacat ccctgatgag tatttcaagc    1020
gttttaatgg actgcagtat ctgcgtttat ctcataatga actggcggat agtggagtac    1080
ctggaaattc ttttaatgta tcatccctgc tggagctgga tctctcctac aataagctta    1140
aaaacatacc gactgtcaat gagaaccttg aaaactatta cctggaggtc aatgaactcg    1200
aaaagtttga ggtaaagagc ttctgtaaga tccttggacc attatcctac tccaagatta    1260
aacatttgcg tctggatggc aaccgtctta cccacaccag tctgccacct gatatgtacg    1320
aatgtctacg tgttgcaaat gaaatcactg ttaattaaca tctactaatt ccaattctat    1380
tgaggtgtac cctggagcaa cattttatgg tttatgtttt tgtgtgtgtc agttttcata    1440
gtattcaatt ttttgggtca ctttattagt ttcatgaatt tcagattctg agggaaatgt    1500
tttgtaaaca ttttactact tttttttta agataagatg aaaggcaggc ctatttcatc    1560
acaagcacag acatagacac acagagacaa caaacttatg ctttatttgt aaatttagtg    1620
ttttctccat ctctactgtc aaatgatgtg caaagtcttc tcttggttga atggaagtca    1680
gccaaggatt ataactcctg aatcttaact taatatgcca aacagcatgg gctacacaca    1740
tatgaatatt taatatcttg aaccaaatga tctcaaattt caatgttcag atttgcttaa    1800
ctgaaaaata ggtggtaaat tttaagactg atgattttgc aaaatactag accaaattca    1860
tgaagccaca tacacttaga gcaatatttt tagtattaag aattatatag ttacctagtg    1920
aaacttctct tttctagaat tatttttcac tctaagtcat gtgtatgttc cttttttaatc    1980
atttgcatgt tatgtttaac aagctcatag caaaataaaa catagcaa                2028

<210> SEQ ID NO 13
<211> LENGTH: 5511
<212> TYPE: DNA
<213> ORGANISM: Canis familiaris

<400> SEQUENCE: 13
gaagccaaac ttttttcctat ttaaggccga agcgaaggaa tctcagtggc tgagttttat     60
gacgggcccg gtgctgcagg gcagggaaca tctgatggtg ctactttgag ctgctgctct    120
ccctcctcg ctgcacaaag agtctcatgt ctcacattta gacatgacga gctttgtgca    180
aaagggacc tggttgcttc tcgctctgct tcagcccgct gtcatctcgg cacagcagca    240
agctattgat ggaggatgct cccatcttgg tcagtcctat gcggatagag atgtctggaa    300
gccagaaccg tgccaaatat gcgtctgtga ctcaggatct gttctctgcg atgacataat    360
atgtgacgaa caagaattag actgtcccaa cccagagatc ccatttggag aatgttgtgc    420
agtttgccca cagcctccaa catctcctcc tcgccctcct aatggtcatg acctcaaagg    480
ccctaaggga gatccaggcc ctcctggtat tcctgggaga aatggcgacc ccggtattcc    540
cggacagcca ggctcccctg ttctcctgg ccccctgga atctgtgaat cctgccctac    600
tggtcctcag cctaactatt ctccccagtt cgagtcctat gacgtcaagg ctggtgtcgc    660
aggaggcggc atcggaggct accccgggcc agctggtccc cctggtcctc ctggtccccc    720
tggtacatct ggtcatcctg ctccccgggg ttccccagga taccaaggcc ccctggtga    780
gcctgggcaa gctggtcctg cgggccctcc aggaccccct ggtgctatgg gtccatctgg    840
tcctgctgga aaagatgggg aatcaggaag acctggacga cctggagagc gagggctgcc    900
tggacctcca ggtatgaaag gtccagctgg catgcctgga ttccccggta tgaaaggaca    960
```

```
tagaggcttt gatggacgaa atggagaaaa gggtgataca ggtgctcctg gattaaaggg      1020
tgaaaatggc ctcccaggtg aaaatggagc cccggaccc atgggtcccc gaggtgctcc      1080
tggtgagcga ggacggccag gcctccccgg ggccgcgggt gctcgaggta acgatggtgc     1140
tcgtggaagt gacggacaac caggccctcc cggtccccct ggaactgcag gattccccgg     1200
ttcccctggt gctaagggtg aagttggacc cgcgggatct cctggttcaa acggctcccc    1260
tggacaaaga ggagaacctg gacctcaggg acatgctggt gctccaggcc ctcctggccc    1320
ccctgggagc aatggtagtc ctggcggtaa aggtgaaatg ggtcccgctg gcattcctgg     1380
agcccctgga ctgataggag cccgggcccc tcctggacca cccggtacca atggtgctcc     1440
tggacagcga ggtggtgcag gtgaacccgg taaaaatggt gccaaaggag agccaggccc    1500
acgcggtgaa cgtggtgaag ctggttctcc aggtatccca ggacctaaag gtgaagatgg    1560
caaagatggc tcgcctggag aaccaggtgc aaacggactt ccgggagctg ccggagaaag    1620
gggtgcacct ggattccgag gacctgctgg agcaaatggc cttccaggag aaaagggtcc    1680
cgctggggag cgtggtggtc caggccctgc agggcccaga ggagctcctg gagaacccgg    1740
ccgagatggt gtcccaggag gtccaggaat gaggggcatg cccggaagcc caggagggcc    1800
aggcagcgat gggaaaccag ggcctccccgg aagtcaagga gaaagtggtc gaccaggtcc    1860
tccaggcccg tctggtcccc gaggtcagcc tggcgtcatg ggtttccctg gtcctaaagg    1920
aaatgatggt gcacctggca agaatggaga gcgaggtggt cctggaggtc ccggccctca    1980
gggtcctgct ggaaagaatg tgaaactgg acctcagggt ccccgggc ctactgggcc        2040 ggctggtgac aaaggagacg cgggacccc tggtccccaa gggctacagg gttgccccgg      2100
aaccagtgga cccccaggag aaaatggaaa accggtgaa ccaggcccga gggtgaatc       2160 tggttcacct ggagttccag gaggcaaggg cgactcaggt gcaccgggcg agcgtggtcc    2220
tcccggggct gcaggcccca tgggcccccg aggtggagct ggaccccag gccccgaagg     2280 agggaagggc gctgctggcc ccctgggcc accggctcg gcaggtaccc ctggtctgca       2340
ggggatgccc ggagagagag gagccccgg cggccccggc cccaagggtg acaagggcga    2400
accaggcagt gcaggtgcag atggagcccc ggggaaggat ggtccagggg gtcctaccgg    2460
tcccatcggc cccctggcc cagccggtca gcctggagat aagggtgaag gtggtgcccc    2520
cggcctcccg gcatagctg gtcctcgcgg tggcccggc gagagaggtg agcacggccc      2580
cccgggaccc gccggcttcc ccggagctcc cggacagaac ggcgagcccg gcgctaaggg    2640
cgaaaagggc gccccccggcg agaagggtga aggaggcccc cccggagtgg cagggccccc   2700
cggaggagcc gggcctgcgg gtcccccggg tccccaggt gtcaaaggtg aacgtggcag    2760
tcccggcggt cccggtgccg ctggcttccc tggtggtcgt ggtcttcctg gccctcctgg    2820
caataatggt aacccaggcc ccccaggctc cagtggtgct ccaggcaagg atgggccccc    2880
cggtccaccc ggtaacaacg gcgctcctgg cagccctggg gtgtccggac ctaaaggtga    2940
tgctggccaa cccggtgaga agggatcgc tggcccccag ggccctccgg agccccagg      3000 ccctctcgga attgctggga tcaccggggc caggggtctc gcgggaccac caggcattcc    3060
aggtcctagg ggaagcccag gcccacaggg cgtcaagggt gaaaatggga agccaggacc    3120
cagtggtcac aacggagagc gcggtcctcc cgggccccag ggcttcccg gcctggccgg     3180 cacggctggt gaacctggaa gagatggaaa cccaggctcc gacggctgc caggccgcga     3240 cggcgctccg ggcggcaagg gtgatcgtgg ggagaacggg tctcctggcg ccccgggcgc    3300
ccccggccac cccggcccc ccggcccccgt gggcccggcg gggaagagcg gcgaccgagg     3360
```

```
cgagacgggc cccgctggtc cctccggcgc tcctggtcct gcaggctccc gaggccccccc    3420
tggtccccaa ggtccacgcg gtgacaaagg tgaaaccggt gaacgtggcc ttaacggcat    3480
caaaggccat cgaggattcc ccggtaaccc aggtgcccca ggctctccgg gtcctgcagg    3540
ccaccaggga gcaatcggta gtccaggccc cgcaggcccc agaggaccag ttggacccag    3600
tggacccccct ggtaaagacg gaacaagtgg acatccaggt cccattggac caccaggccc    3660
tcgaggtaac agaggagaaa gaggatctga gggctccccc ggccacccag acagccagg     3720
tccccccggg cctcctggtg cccctggacc ctgctgtggt gggggcgctg ccgccctggc    3780
tgccgccgga gggagaaaag ctggcgggtt gccccctat tacgagatg agccaatgga     3840
tttcaaaatc aacaccgagg agattatgac ttcgctcaaa tccgtcagtg gacaaataga    3900
aagcctcgtt agcccgacg ggtcccgcaa cacccccgct cggaactgcc gggacctcaa     3960
attctgccat ccagagctca agagcggaga gtactgggtt gaccccaacc aaggctgcaa    4020
gttggatgcg atcaaagtat ctgcaacat ggaaacaggg gagacgtgcc tgaatgccag     4080
tcccgggagc gttccccgga agaactggtg gacagatct ggtgctgaga agaaacatgt     4140
ttggttttgga gaatccatgg atggtggctt ccagtttggc tacggcaatc ccgagctgcc    4200
tgaagacgtc ctcgatgtcc agctggcatt cctccgcctt ctctccagcc gggcctccca    4260
gaacatcacg tatcactgca agaatagcat cgcgtacatg gatcacgcca gtgggaatgt    4320
aaagaaagcc ctgaggctga tggggtcaaa tgaaggtgaa ttcaaggctg aaggaaacag    4380
caaattcaca tacacagtcc tggaggatgg ttgcactaaa cacactgggg aatggggcaa    4440
aacagtcttc gaataccgaa cacgcaaggc tgtgagacta cctattatag atattgcacc    4500
ctatgatgtt ggtggtcctg atcaagaatt tggtgtggac gttggccctg tttgcttttt    4560
ataaaccaaa ctctatctga aacccccagca aaaaatttca cactccatat gtgttcctct    4620
cgttctaacc ttgtcaacca gtacaagtga ccaactcaat tccagttatt tatttccaaa    4680
agttttggaa aaaagtataa tttggcaaaa aaaaagatac ctttttttt tttttttttg    4740
ctgttacacc aaatacagtt caaatgcttt ttgttctatt ttttaccaa tttcaatttc    4800
aaaatgtctc aatggtgcta taataaataa acttcaacac tcttacaata acactgtgtt    4860
atattctttg aatcctagcc catttgcaga gcaatgacta ggcttaccat taaaagataa    4920
cctttctttc tgaaatagtc aaacatgaaa ttagagaaga cctccctgtt tcaactacct    4980
caacctggtc agaaatacag atgaattcta gaagtcctgg aagatgaaaa aaatcataaa    5040
ttagcaataa tttcctaaaa tattgataaa aaagtatagt acgagaattt aaagaaaaaa    5100
tttttttaaa tctacgattt taatcttgga tatcaactgc ttttaaaggt gcttttctcc    5160
tttcttgtca ttgctgaaat ggtcaagatt acccacattt gggaaggctt taagacaca     5220
tgttatggtg ctaatgtact ttcactttaa aaactccagg tcagaattgt tgccttgcat    5280
tcaaaacata aatgcacacc atcttttcaaa aaaatttatt gccgtgtcac ttcaggggac    5340
tctctctccc ttgatcctgt aaaagtcaac aacaacaaca acaacaacaa aaaattatgg    5400
ggctgctttt gtcacagtaa cacagagaat gtgctgaaat ttaactttgt aagcttgtat    5460
gtggttgttg gtctttttt ttttttcctc cagacaccca taataaaata t             5511
```

<210> SEQ ID NO 14
<211> LENGTH: 1470
<212> TYPE: DNA
<213> ORGANISM: Canis familiaris

<400> SEQUENCE: 14

```
taaaaccagg aggttctcaa cctattaaca ttcacaaaac agcacctacc ccctcctcct      60
ttccacacct gcaaactctt tgcttgggc tgaatattta gtttaattac atctcacctt     120
taagggctcc tgtggcaaat ccccggatta aaaggttcct tggctgtgaa aatacataac    180
ctaaaccatg aaggcaacta tcatcttcct cctgcttgca caagtttcct gggctgggcc    240
gttccaacag agaggcttat ttgactttat gctagaagat gaggcttccg ggataggccc    300
ggaggaccgt gcacctgaca tgcctgacct cgagcttctg ggacctgtgt gtcccttccg    360
ctgtcagtgc catctccgag tggtccagtg ttccgacctg ggtctggaca agtaccaaa    420
agatcttccc cctgacacta cgctgctcga cttgcaaaac aacaaaatca ccgaaatcaa    480
agatggagac ttcaagaacc tcaagaacct gcataccttg attcttgtaa acaacaaaat    540
tagcaaaatc agccctggag catttacacc tttgttgaaa ttggaacgac tttatctgtc    600
caagaatcat ctgaaggaat tgccagaaaa aatgcccaaa actcttcagg agctgcgtgc    660
ccatgagaat gagatcacca aagttcgaaa agctgtgttc aatggactga accagatgat    720
cgtcgtagag ctgggcacca atcccctgaa gagttcaggg attgaaaatg gagccttcca    780
gggaatgaag aagctctcct atatccgcat tgctgatacc aatataacta ccatccctca    840
aggtcttcct ccttccctta ctgaattaca tcttgaaggc aacaaaatca ccaaggttga    900
tgcatctagc ctgaaaggac tgaataattt ggctaagttg ggactgagtt ttaacagcat    960
ctccgctgtt gacaatggca ctctagccaa cactcctcat ctgagggagc ttcacttgga   1020
caacaataag ctcatcagag tacccggtgg gctggcggag cataagtaca tccaggttgt   1080
ctaccttcat aacaacaata tatctgcagt cggatctaat gacttctgcc cacctggata   1140
caacaccaaa aaggcttctt attcaggtgt gagccttttc agcaacccag tgcagtactg   1200
ggagatccag ccatccacct tccggtgtgt ctacgtgcgc tctgccatcc agcttggaaa   1260
ttataaataa ttcccaagaa agccctcgtt tttataacct ggcaaaatcc cattaatatc   1320
attgctcaaa aaaaaaaaa aaaaaaacta aatacgggaa acttagctgc aatgtgaatg   1380
ttttcccct aatttataat actaaaccaa attgcattta aaatgccaaa aaaaaaaat    1440
tttggccgcc aaaaaaaaaa aaaaaaaaaa                                   1470
```

<210> SEQ ID NO 15
<211> LENGTH: 1760
<212> TYPE: DNA
<213> ORGANISM: Canis familiaris

<400> SEQUENCE: 15

```
attcggcacg aggatgccgc ggggccccgg ctcgctgctg ctgctcgtcc tagcgtcgca      60
ctgctgcttg ggctcggcgc gcgggctctt cttcggccag cccgacttct cctacaagcg    120
cagcaactgc aagcccatcc cggccaacct gcagctgtgc cacggcatcg agtaccagaa    180
catgcggctg cccaacctgc tgggccacga gaccatgaag gaggtgctgg agcaggcggg    240
cgcctggatc ccgctggtca tgaagcagtg ccaccccgga ccaagaagt tcctctgctc    300
gctcttcgcc ccgtgtgcc tcgacgacct ggacgagacc atccagccgt gccactctct    360
ctgcgtgcag gtgaaggacc gctgcgcccc ggtcatgtcg gccttcggct tcccctggcc    420
ggacatgctc gagtgcgacc gattcccca ggacaacgac ctctgcatac ccctcgctag    480
cagcgaccat ctcctgccgg ccaccgagga agctccaaag gtatgcgaag cctgcaaaaa    540
taaaaatgag gatgacaacg acataatgga aactctttgt aaaaatgatt ttgcactgaa    600
```

```
aataaaagtg aaggagataa cctacatcaa cagagatacc aaaatcatcc tggagaccaa    660
gagcaagacc atttacaagc tgaacggtgt gtctgaaagg gacctgaaga aatccgtgct    720
gtggctgaaa gacagcctgc agtgcacctg cgaggagatg aatgacatca acgcgcctta    780
tctggtcatg ggacagaaac taggtgggga gctggtgatc acctcagtga agcggtggca    840
aaaggggcag agagagttca agcgcatctc ccgaagcatc cgcaagttgc agtgctagtt    900
tgccccccc  tccccaggcc gcctccagag ccaggctgac cacttccgct ctgggtcccc    960
agctctcatc cccccaagca caggcccttg cagctctggc cccagcctgg agcagcttcc   1020
cttgcctttt gcacgtttgc accctggcat ctcctgaatt ataaggcctt aggaagcttc   1080
aggagtggat actgttttaa acatacggga ggaacccacc cagatcttgt agaaatgttc   1140
aaactaataa aatcatggaa tattttacg  gaagttttta aatagctcaa ctttagtttt   1200
gaataggtac agctgtgact tgggtctgac tttccttctt tctgtttggt ttgggccaac   1260
tgattttcaa tttcgtggta aggttgccgt aacgtgcaaa tggcttcatt tttcgatgtg   1320
gcccaaaatg tggtgggtca caatccttcg ttgagataaa gctggctgtt attcgacgtt   1380
tctcagctcc agcctgagac ttcagagcct aagtcttata ataattcacc tgtcatttta   1440
tgccccgtt  gggaacttac aacagtagca gcatgtactg atttccgggt agagtacttc   1500
catttatcaa aagcacatta accaccatag catgattctt cgaataaagg gcaaaacaga   1560
ttttataatt gacctgagta ctttaagctt ttgtttaaaa cattttttac ttaatttgc    1620
aaattaaacc attgtagctt acctgtaata tacatagtag ttgaccttaa aaagttgtaa   1680
aaatattgct ttaaccaaca ctgtaaatat ttcagataag cattatattc ttgtatataa   1740
actttgcttc ctgttttaaa                                               1760
```

<210> SEQ ID NO 16
<211> LENGTH: 2937
<212> TYPE: DNA
<213> ORGANISM: Canis familiaris

<400> SEQUENCE: 16

```
atggaggctg aagtgccatg gaaagtggag catgtcgtca ctgttgctag taaacagcgc     60
cagaggcact tccaagggac cagttgccac ttggagctcc agactatgga aaagatgctg    120
gtgggctgct ttctgttggt cctcggacag atcctccttg tcctccctgc tgaggccaaa    180
gagcggactc cctggaggtc catctccaga gggagacatg cttgacccca tccccagacg    240
gccctcctgg agagctcctg tgagaataaa caggcagacc tggtcttcat catcgacagc    300
tcccgcagtg tcaacaccca tgactatgca aaagttaagg agttcatcct ggacatcttg    360
cagttcttgg acatcagtcc tgacctcacc cgagtgggcc tgctgcagta tggcagcacc    420
atcaagaacg agttctccct caagaccttc aagaagaagt ctgaagtgga gcgtgccgtc    480
aagaggatga ggcacctgtc cacaggcacc atgacgggc  tggccatcca gtacgccctg    540
aacattgcat tctcagaagc agagggggca cggcccctga gggagaacgt gctgcgggtc    600
ataatgattg tgaccgacgg gaggccacag gactccgtgg ccgaggtggc tgccaaggca    660
cgtgacacag gcatcctgat ctttgccatc ggtgtgggcc aggtggacct caacacactg    720
aaggccattg ggagtgagcc ccatgaggac catgtcttcc tggtggccaa cttcagccag    780
atggagtccc tgacctcggt gttccagaag aagttgtgca tggtccacat gtgcagcgtc    840
ctggagcata actgtgccca cttctgcatc aatacccccg gctcatacgt ctgcaggtgc    900
```

```
aaacaagggt acatcctcaa ctcagatcag acgacttgca gaatccagga tctgtgtgcg    960
gccaaggccc atgggtgtga gcagctctgt gtcaatgtgc tcggctcctt tgtctgccag   1020
tgttacagcg gcttcacact ggctgaggac gggaagacgt gtgcggctgt ggactactgt   1080
gcctcagaga accacggatg tgaacatgag tgtgtgaatg ctgacagctc ctactttgc    1140 cggtgccgta aaggatttac tcttaaccca gataaaaaaa catgtgcaaa gatagactac   1200
tgtgcctcgc ctaatcaagg atgtcagcac gagtgtgtta acacagatga ctcctattcc   1260
tgtcgctgcc taaaaggttt taccttgaat ccagataaga aaacctgcag aaggatcaac   1320
tactgtgcat tgaacaaacc gggctgtgag catgaatgca tcaacataga ggatggctac   1380
tactgccgct gccgccaggg ctacaccctg acccccaatg caagacttg cagcagggtg     1440 gatcactgcg cggagcagga ccatggctgt gagcagctgt gcctgaacac tgaggattct   1500
tacgtctgcc agtgctcaga aggcttcctc atcaacgacg acctcaagac ctgctccagg   1560
gcggattatt gcttgctgag caaccatggt tgcgaatact cctgcgtcaa cactgaccga   1620
tcctttgttt gtcggtgtcc tgaggatac gtgctccgca gtgacgggaa gacctgtgcc     1680
aaattggact cctgtgctgt gggagaccat ggctgtgaac attcatgtgt aagcagtgga   1740
gactcttttg tgtgccagtg ctttgaaggg tatatactcc gtgaagatgg gaaaacctgc   1800
agaaggaaag gtgtctgcca atcagtaaac catggctgtg agcatatttg tgtgaacagt   1860
gatgagtcgt acatctgcaa gtgccgggaa ggattcaggc ttgctgaaga tgggaagcgc   1920
tgcagaagga aggatgtctg caaatcgacc taccacggct gtgaacacat ttgtgttaat   1980
catggcaact cctacatctg caaatgctca gagggatttg ttctagctga ggatggaaaa   2040
cggtgcaaga gatgcactga aggcccgctt gacctggtct ttgtgatcga tgggtccaag   2100
agcctcgggg aagagaattt cgagattgtg aagcagttcg tcgcgggcat tatagattcc   2160
ttggcggttt ccccccaaagc cgcccgagtg gggctgctgc agtactccac gcaggtccgc   2220
acggagttca ccctgggaga cttcagctcg gccagagaca tgaaaaaagc cgtggcccac   2280
atgaagtaca tgggcaaggg ctctatgacg gggctggccc tgaaacacat gtttgagaga   2340
agttttaacc cagtggaagg ggccagaccc gtgtccccg gggtgtccag agtggccatc     2400
gtgttcacgg acggccgggc ccaggacgac gtctccgcgt gggcccgcag agcccgggcc   2460
ggcggcataa ctatgtatgc tgtcggggta ggaaaagcta ttgaggaaga gctacaagag   2520
attgcctctg agcccacaga caagcatctc ttctatgccg aagacttcag cacaatggga   2580
gagataagtg aaaaactaaa gaagggtata tgtgaagctc tggaagactc tgatggaagt   2640
caggactccc cagcagggga actgccaaag agggtccacc agccaacaga atctgagcca   2700
gtcaccataa atatccgaga cctactttcc tgttctaatt ttgcagtgca acaccggtat   2760
ctgtttgaag aagacagtgt ttcacggtcc acacaaaaac tttttcattc aacaaaatct   2820
tcaggaagtc ctttggaaga aaaacacgat cagtgcaaat gtgaaaatct tataatgttc   2880
cagaaccttg cgaatgaaga agtgagaaag ttaacacaac gctatatcct tttctaa     2937
```

<210> SEQ ID NO 17
<211> LENGTH: 1054
<212> TYPE: DNA
<213> ORGANISM: Canis familiaris

<400> SEQUENCE: 17

```
ttatgcaagt gctggccgcc ggccggcgcc tcccctcggt ctttcacccc ggccgttacg     60
aaagcgagac cccctcccgc cccggctata aagcgggcgg cccggcggcc ccggcggatc    120
```

```
gccgccttcc ctggctccac gcgcgccccg caccgcggcc aggcttgcgc gcagctccgg      180
tgggcggact cccgggcacg atggagtggg tgtgggcgct cgtgctgctg gcggcgctgg      240
gcagcgcccg gcggagagc gactgccgag tgagcaactt ccaagtcaag aagaacttcg       300
acaaggctcg cttcgccggg acctggtacg ccatggccaa gaaggacccc gagggcctct      360
ttctgcagga caacatcgtc gctgagttct cggtggatga aatggccgg atgagcgcca       420 cggccaaggg ccgagtccgg cttttgaata actgggacgt gtgtgcagac atggttggca     480
ccttcacaga caccgaggac cctgctaaat tcaagatgaa gtattgggc gtagcgtcct      540 tcctccagaa aggaaatgat gaccactgga tcatcgacac ggactatgac acctatgccg     600
tgcagtattc ctgccgcctc ctgaacctcg atggcacctg tgctgacagc tactccttcg    660
tgttttcccg tgaccccaat ggccttcccc tggaggcaca aaagatcgtg aggcagaggc    720
aggaggagct gtgcctggcc aggcagtaca ggctgatcgt tcacaatggg tattgtgacg   780
gcagatcaga accaaacact ttgtagcaac gtggagtttc atttgaaaag ttcccattaa    840
ttcatgcagc cttcaattgt ctcgtatctt aggggtttag tttgccctgc tctgcacccc   900
tgccctccgc aaacatggaa tctcagcaca cctaaaaata tcggtgggga tcagtgaatc   960
tgcactcaga tgactgtctt tcctggagtt ttctaaggaa ttgtttcaag cttaggattc   1020
cagactttga tttattaaaa tgtagtcacc tgtt                                1054

<210> SEQ ID NO 18
<211> LENGTH: 2138
<212> TYPE: DNA
<213> ORGANISM: Canis familiaris

<400> SEQUENCE: 18
gagacacacc actaccctca ccatgagccc caggcagccc ctggtcctgg tgttcctggt     60
gctgggctgc tgctctgcag ctcccagacc acacaagccc accgttgtgg tctttccagg    120
agacctgaga actaatctca ctgacaagca gctggcagag gaatatctgt ttcgctatgg    180
ctacactcaa gtggccgagc tgagcgacga caagcagtcc ctgagtcgcg ggctgcggct    240
tctccagagg cgcctggctc tgcctgagac tggagagctg gacaaaacca ccctggaggc    300
catgcgggcc ccgcgctgcg cgtcccggga cctgggcaaa ttccagacct tgagggcga    360 cctcaagtgg caccacaacg acatcactta ctggatacaa aactactcgg aagacttgcc    420
ccgcgacgtg atcgacgacg cctttgcccg agccttcgcg gtctggagcg cggtgacacc    480
gctcaccttc actcgcgtgt acggccccga agccgacatc atcattcagt ttggtgttag    540
ggagcacgga gatgggtatc ccttcgatgg gaagaacggg cttctggctc acgcctttcc    600 tccccggcccg gcattcagg agacgcccca cttcgacgac gaggagttat ggactctggg   660
caagggcgtc gtggttccga cccacttcgg aaacgcagat ggcgcccct gccacttccc   720 cttcaccttc gagggccgct cctactcggc ctgcaccacg gacggccgct ccgatgacac    780
gccctggtgc agcaccacgg ccgactatga caccgaccgt cggttcggct ctgccccag    840 cgagaaactc tacacccagg acggcaatgg ggacggcaag ccctgcgtgt tccgttcac    900 cttcgagggc cgctcctact ccacgtgcac caccgacggc cgctcggacg ctaccgctg    960 gtgctccacc accggcgact acgaccagga caaactctac ggcttctgcc caacccgagt   1020
cgattccgcg gtgaccgggg caactccgc cggggagccc tgtgtcttcc ccttcatctt   1080
cctgggcaag cagtactcga cgtgcaccag ggagggccgc ggagatgggc acctctggtg   1140
```

-continued

| | |
|---|---|
| cgccaccact tcgaactttg acagagacaa gaagtggggc ttctgcccgg accaaggata | 1200 |
| cagcctgttc cttgtggccg cccatgagtt cggccacgcg ctgggtttag atcattcatc | 1260 |
| ggtgccagaa gcgctcatgt accccatgta cagcttcacc gagggccccc ccctgcatga | 1320 |
| agacgacgtg aggggcatcc agcatctgta cggtcctcgc cctgaacctg agccacagcc | 1380 |
| tccaaccgcc ccgcccaccg cccgcccac cgtctgcgct actggtcctc ccaccacccg | 1440 |
| cccctcagag cgccccactg ctggccccac aggcccccct gcagctggcc cacgggtcc | 1500 |
| ccccactgct ggcccctctg aggcccctac agtgcctgtg gatccggcag aggatatatg | 1560 |
| caaagtgaac atcttcgacg ccatcgcgga gatcaggaac tacttgcatt tcttcaagga | 1620 |
| agggaagtac tggcgattct ccaagggcaa gggacgccgg gtgcagggcc ccttccttat | 1680 |
| caccgacacg tggcctgcgc tgccccgcaa gctggactcc gcctttgagg acgggctcac | 1740 |
| caagaagact ttcttcttct ctgggcgcca agtgtgggtg tacacaggca cgtcggtggt | 1800 |
| aggcccgagg cgtctggaca agctgggcct gggcccggag gttacccaag tcaccggcgc | 1860 |
| cctcccgcaa ggcgggggta aggtgctgct gttcagcagg cagcgcttct ggagtttcga | 1920 |
| cgtgaagacg cagaccgtgg atcccaggag cgccggctcg gtggaacaga tgtaccccgg | 1980 |
| ggtgcccttg aacacgcatg acatcttcca gtaccaagag aaagcctact tctgccagga | 2040 |
| ccgcttctac tggcgtgtga attctcggaa tgaggtgaac caggtggacg aagtgggcta | 2100 |
| cgtgaccttt gacattttgc agtgccctga ggattaga | 2138 |

<210> SEQ ID NO 19
<211> LENGTH: 1636
<212> TYPE: DNA
<213> ORGANISM: Canis familiaris

<400> SEQUENCE: 19

| | |
|---|---|
| cgccggcgcc gctgaccgag gcctgctggg attccagaat tggagaagga ggcatgatga | 60 |
| agactctcct gctgctggtg gggctgctgc tgacctggga caatggacgg gttctgggag | 120 |
| accaggctgt ctcagacacc gagctccagg aaatgtccac cgaaggtagt aagtacatta | 180 |
| ataaggaaat aaaaaatgct ctcaaggggg tgaaacagat aaagacccta atagaacaga | 240 |
| caaacgaaga gcgcaaatca ctgctcagca acctggagga agccaagaag aagaaagagg | 300 |
| atgcactaaa tgataccaag gattctgaaa cgaagctgaa ggcgtcccag ggggtgtgca | 360 |
| atgacaccat gatggccctc tgggaggagt gcaagccctg cctgaaacag acctgcatga | 420 |
| agttctacgc acgtgtctgc agaagtggct cggggctagt tggccaccag ctcgaggagt | 480 |
| tcctgaacca gagttctccc ttctacttct ggatgaatgg cgatcgtatc gactccctgc | 540 |
| tggagaacga ccggcagcag acccacgccc tggacgtcat gcaggacagc ttcaaccggg | 600 |
| catccagcat catggatgag cttttccagg acagattctt cacccgggag ccccaggata | 660 |
| cttaccacta ctcaccctttc agcttattcc agaggaggcc tttcttcaat cccaaatttc | 720 |
| gcatcgcccg gaacataata cctttcccta gattccagcc cttaaacttc catgacatgt | 780 |
| ttcagccctt ctttgacatg atacaccagg ctcaacaggc catggatgtt aacctgcata | 840 |
| gaattcctta ccacttccca attgaattcc agaagaagaa taaccgcacc gtgtgcaagg | 900 |
| agatccgtca caactccaca ggttgcctga aaatgaagga ccagtgtgaa aagtgccagg | 960 |
| agatcttgtc agtggattgt tcttccaaca accctgcgca ggtccagctg cgacaggaac | 1020 |
| ttagtaattc cctccagatt gcggagaagt tcaccaagct ctacgacgag ctgctgcagt | 1080 |
| cctaccagga gaagatgttc aacacgtcct ccctgctgaa gcagctgaac gagcagttta | 1140 |

```
gctgggtgtc ccaactggct aacctcactc aaagtgaaga cccattctat ctccaggtca   1200
cgacggtggg ttctcagact tctgactcca atgttcccgt gggcttcact aaggtggttg   1260
tgaagctctt tgattctgac cccatcacgg tgatgatccc agaagcagtc tccaggaaca   1320
atcctaaatt tatggagact gtggcagaga aggctcttca ggagtatcgc caaaagcacc   1380
gagaggaatg agatgtgaac attgcttctc caaatatggg agggctgagt tcctttgacc   1440
ccaagatgag tgctaggccc ctagagagag ctctgcatgt caccaagtga ccaggccttg   1500
cctcgaggcg ctcctgtctc ctaacccagc tttccttcct ctggactccg cactgtaacg   1560
cctacgtttg ctgatcatgg gaagaactcc tgtgtgccac taactcaata aaaccgccaa   1620
ggaatctgaa aaaat                                                    1636

<210> SEQ ID NO 20
<211> LENGTH: 2321
<212> TYPE: DNA
<213> ORGANISM: Canis familiaris

<400> SEQUENCE: 20
caggtctgtg ctccaggctc ctagccacag gcccaggaag atgaggctcg ccgtccgcgc     60
tctgctggcc tgcgcggtcc tggggctgtg tctggctgtc tcccctgaga aaactgtgag    120
atggtgcact gtctcaaatc atgaggccag taagtgttcc agtttcatgg aaaatatgaa    180
aaccgtcctt gaaaatggtc cttttgtcag ctgtgtgaag agaacctcct accttgagtg    240
catcaaggct atttgggcaa atgaagcaga tgctgtgaca cttgatgcag gtttggtgtt    300
tgaggcaggc ctgaaccccct acaacctaaa gcctgtagtg gcagagttct atgggaaaga    360
taagcaaacc cgctatattg ctgtggctgt ggtgaagaag agcagtacgt tcaatctgaa    420
tcagctccaa ggcaagaaat cctgccacac aggccttggc aggtctgctg ggtggaacat    480
ccccatgggc ttactttatt ggaagttgcc agagccacgt gaatctcttc agaaggcagc    540
gtccagtttc ttcacggcca gctgtgttcc ctgtgtggat cggacagctt tccccaaact    600
gtgtcaactg tgtgtgggga agggacggaa caagtgtgcc tgctccaacc atgagccata    660
cttcggctac tcgggtgcct tcaagtgtct gatggaggac gctggggaag tggccttgt    720 caagcattca acagtgttgg agaacctgcc aaacaaagct gacctggacc agtatgagct    780
gctctgccca gacaacaaac gaaagccagt gggggaatat aagcagtgct acctggccaa    840
ggtcccttcc catgctgttg tggcccgaag tgtgggggc aaggaagact tgatctggga    900
gcttctaaac caggcccagg aacattatgg caaagacaaa tctaaagtct ccagctctt     960 cagctcaact ttggggaagg acctgctgtt taaagactct gccgaagggt tttttaggat   1020
tcctcctaaa atggacacct ggctgtacct gggatatgag tatgtcactg ctcttcggaa   1080
cctaagggaa gatgtgcgcc cagataccc aagggatgaa tgcaagaagg tgaaatggtg   1140
tgcagtaggt caccatgaga ttgccaagtg tgatgagtgg agtgtaaaca gcgaagggaa   1200
aatagagtgt gaatcagcag agtctactga agactgtatt gccaagattg cgaaaggaga   1260
ggctgatgcc atgagcttgg atggaggcta tatctacata gcgggccagt gcggtctggt   1320
gcctgtcctg gcagagaact acaaaactca gggctctaca tgtagcaaca cagcagagga   1380
agggtatctt gctgtggccg tagttaagag attagataaa accatctctt ggaataatct   1440
gcaaggcagg aagtcctgcc acactgcagt agatagaact gcaggctgga acattcccat   1500
gggcctgctc tacaacagga tcaaccactg tgaatttgat aaatttttct ctcaaggctg   1560
```

| | |
|---|---|
| tgcccccgga tctatgcgga attccagtct ctgtgctctg tgtattggct cagcaaatgt | 1620 |
| tccaggaaag gagtgtgttc ccaataacca tgagagatac tatggctaca caggggcttt | 1680 |
| caggtgtctg gttgagaagg gagatgtggc ctttgtgaaa gaccagactg tcttgcagaa | 1740 |
| cactgggga aagaacactg aagattgggc taaggatctg aaggaagagg actttgagct | 1800 |
| gctgtgccct gatggccaaa ggaagtctgt ggacaaggct cctgagtgct tcctagccaa | 1860 |
| agccccaaat catgctgtgg tctcaaggaa agacaaggca tcttgtgtta gcaaaatgtt | 1920 |
| acttgaccag cagcttttgt ttggaagaaa tggaaatgac tgctcgggca gttttgctt | 1980 |
| gttccactca gcaaccaagg accttctgtt cagggacgac acacaatgtt tggccaaact | 2040 |
| tccagaggac acaacatata aatcatactt aggagcagag tatatcacgg ctgttgctaa | 2100 |
| cctgagacaa tgctccacct cgaaactcct ggaggcctgc actttccata catcttaaaa | 2160 |
| tccaagaggc ggagacacac cagatggtga tgggagctca cgtgacccat aagttccctc | 2220 |
| ggggcctcac tggcctgggt ggtttgtctg gtttcacagt tcagcggtgg aacctctgta | 2280 |
| gaacattaaa taaacattat tattggtgtt atcttttaaa a | 2321 |

<210> SEQ ID NO 21
<211> LENGTH: 576
<212> TYPE: DNA
<213> ORGANISM: Canis familiaris

<400> SEQUENCE: 21

| | |
|---|---|
| ctttccgaga ccgctccagg ttggtgctcg atacctgatg cccctgatgc cccgggaggg | 60 |
| ctgcccctcc aagaacacta gaaaaggggt ggagggaact ccggggaggg aggaggggtg | 120 |
| tcactgatcg ctcccacccc tgcttctgct tccagagagc ccctccggcc ccgccatgag | 180 |
| gctcattctg tcgctcccgg ttttggtggt ggttctgtcg atggttttgg aaggtccagc | 240 |
| ccccgcccag gcggccggag aaatctccag cacttttgag cgcatcccgg ataagctgaa | 300 |
| ggagtttggt aacaccctgg aagacaaggc ccggcagcc attgagagca tcaagaagag | 360 |
| cgacattcct gcaaagaccc gaaactggtt ttctgaggct ttcaagaaag tgaaggagca | 420 |
| tctcaaaact gccttctcct gaacaccagg agagccgccc ctctactctg gcctgtgtgc | 480 |
| cccaggaggg ggctctgaaa tttcccatcc cctggctcct tgccaaggac ttcatgatgt | 540 |
| tcatgtctac ccccaacctc caataaaaat cctata | 576 |

<210> SEQ ID NO 22
<211> LENGTH: 1275
<212> TYPE: DNA
<213> ORGANISM: Canis familiaris

<400> SEQUENCE: 22

| | |
|---|---|
| atgcccttgc tctggctgag aggattcttg gtggcgagtt gctggattat agtgcggagc | 60 |
| tccccgaccc cggggcccga ggggcccggc gcggccccg cctgcccggc ctgcgcgctc | 120 |
| accgccctgc ccaggatgc ccccaactcc cagcccgaga tggtggaggc cgtcaagaag | 180 |
| cacatcctca acatgctgca cttgaagaag agacccgaag tcacccagcc ggtgcccaag | 240 |
| gcggcgcttc tgaacgcgat ccgcaagctg cacgtaggca aagtcgggga gaacgggttc | 300 |
| gtggagatag aggatgacat cggcaggagg gcagaaatga atgaactcat ggagcagacc | 360 |
| tcggagatca tcacgttcgc ggaatcaggc acagccagga aacgctgca ctttgagatt | 420 |
| tccaaagaag gcagtgacct gtcggtggtg gagcgtgcag aagtctggct cttcctcaaa | 480 |
| gtccccaagg ccaacaggac caggaccaaa gtcaccatcc ggctcttgca gaagcacccc | 540 |

```
cagggcagct tggatgcggg ggaggaggcc gaggacatgg gcttcccgga ggagaggaac      600
gaggtgttga tttctgaaaa ggtggtggac gcacggaaga gcacctggca catcttccct      660
gtctccagca gcatccagcg cttgctggac cagggcagga gctccctgga cgttcggatt      720
gcctgcgagc agtgccacga gacgggcgcc agcctggtgc tcctgggcaa gaagaagaag      780
aaggaggagg aggggaagg gaagaagaag gacggaggag acgcaggggc cggggggac        840 gaggacaagg agcagtccca cagacctttc ctcatgctgc aggcccgcca gtctgaagac      900
caccctcatc ggcggcggcg gcggggcctg gagtgtgacg gcaaggtcaa catctgctgt      960
aagaaacagt tctttgtgag cttcaaggac attggctgga acgactggat cattgccccc     1020
tccggctatc acgccaacta ctgcgagggt gggtgcccga gccacatagc aggcacgtcg     1080
gggtcctcgc tctcctttca ctcgaccgtc atcaaccact accgcctgcg gggtcacagc     1140
cccttcacca acctcaagtc gtgctgtgtg cccaccaagc tgagaccaat gtccatgctg     1200
tactacgatg atgggcaaaa catcatcaaa aaggacattc agaacatgat cgtggaggag     1260
tgcgggtgct catag                                                       1275
```

COMPOSITIONS AND METHODS FOR DIAGNOSING AND TREATING KIDNEY DISORDERS IN A CANINE

This application is a national stage entry under 35 U.S.C. §371 of International Patent Application No. PCT/US2010/062031, filed 23 Dec. 2010, which claims priority to U.S. Provisional Patent Application Ser. No. 61/289,773, filed on 23 Dec. 2009, which are incorporated herein by reference.

FIELD OF THE INVENTION

The present invention relates to compositions and methods for: diagnosing of, devising and monitoring a treatment plan for, and monitoring the status of a kidney disorder characterized by an abnormal loss of renal function, renal failure, reduced glomerular filtration rate or glomerulonephritis, in a canine, wherein the kidney disorder is detectable by utilizing at least one relevant biomarker isolated and measured from a biological test sample taken from such canine. A relevant biomarker for practice of the compositions and methods of the present invention comprises an RNA transcript or its translation product taken from such biological test sample of such canine. A biological test sample for the practice of the method of the invention comprises a tissue sample of a kidney of such canine or a specimen of a biological fluid taken from such canine.

The present invention also relates to the identification of combinations of novel biomarkers for use in diagnosing of, devising and monitoring a treatment plan for, and monitoring the status of, a kidney disorder characterized by an abnormal loss of renal function, renal failure, reduced glomerular filtration rate or glomerulonephritis, in a canine.

BACKGROUND OF THE INVENTION

Glomerulonephritis or glomerular nephritis ("GN") is a renal disease which is characterized by inflammation of the glomeruli or capillary loops of the kidney. It is a pathologic process associated with a number of diverse underlying diseases. The condition occurs in acute, sub-acute and chronic forms and also secondary to an infection. The former conditions, where a concurrent illness cannot be found, are generally referred to as idiopathic glomerulonephritis. The latter conditions are generally referred to as secondary GN. Whatever the underlying cause, immune complexes form and result in a series of events leading to glomerular injury and loss of renal function, proteinuria and ultimately, in some cases, renal failure.

Nephritis is an inflammation of the kidney, which may be a focal or diffuse proliferative or destructive disease involving the glomerulus, renal tubule or the kidney interstitial (or connective) tissue. The most common form of nephritis is glomerulonephritis. Nephritis may progress through a number of stages ending in end-stage kidney disease or end-stage renal failure.

Renal failure results from the inability of the kidney to maintain its normal functions. As a result, metabolic waste products and metabolites accumulate in the blood. These waste products and metabolites may adversely affect most bodily systems. Disturbances in the maintenance of fluid and electrolyte balances are characteristics of renal failure.

Acute renal failure may occur suddenly due to trauma, infection, inflammation or exposure to nephrotoxic substances. This condition may result in dehydration, hypotension and circulatory collapse. Acute renal failure is frequently segregated into three categories: (1) pre-renal failure, which is associated with decreased renal blood flow; (2) intra-renal failure, which is associated with ischemia and toxins; and (3) post-renal failure, which results from obstruction of urine flow.

Chronic renal failure involves a progressive loss of kidney function that may eventually progress to end-stage renal disease or failure. At inception, chronic renal failure begins as a diminishing kidney function, without appreciable accumulation of metabolic waste products in the blood. As the glomerular filtration rate slows due to inflammation, waste products begin to accumulate. The disease progresses to uremia due to low kidney function, and high levels of protein end products start to accumulate and impair bodily functions. Common causes of chronic renal failure include: inflammation, infection, urinary tract obstruction and certain systemic diseases and toxicities, including hypercalcemia, lupus erythematosus, diabetes mellitus and hypertension.

End-stage renal disease is marked by irreversible chronic renal failure. Serum creatinine and blood urea nitrogen levels continue to rise and the resulting uremia impairs all bodily systems. The kidney can suffer permanent and almost complete loss of function on the order of 10% or less of normal kidney function. One cause of end-stage kidney disease is glomerulonephritis. Other causes include those mentioned for chronic renal failure.

Glomerulonephritis may arise as a result of a biological insult to the immune system. Foreign substances may adhere to the basement membrane and cause an immune response resulting in the production of antibodies. These antibodies may combine with the foreign substances to cause immune complexes that become deposited on the walls of the tiny glomerular capillaries, resulting in damage to the nephron. Alternatively, in some individuals the immune system can create autoantibodies which are immunoglobulins that may attack kidney cells resulting in a so-called autoimmune response. If proteins in the body are altered, an autoantibody response may ensue because the autoantibodies recognize the altered proteins as non-self. These autoantibody-protein complexes may likewise be deposited on the basement membrane of the glomerulus causing a disruption of the functioning of the nephron.

Glomerulonephritis is a common cause of proteinuria in dogs and may be either the idiopathic or secondary form of the condition. In the latter situation, the condition may develop secondary to neoplasia, inflammatory diseases, endocrine malfunctions, infections or familial nephropathies. As in humans, GN in dogs is mediated immunologically, involving immunoglobulins and complement factors in the body of the animal. Injury occurs within the glomeruli of the kidney resulting in morphological changes to the glomeruli. Eventually the injury is irreversible and leads to malfunction of the nephrons.

It is generally accepted in the scientific community that the regulation of gene expression plays a key role in the development of some diseases or conditions that affect an animal's health and well being. Similarly, a differential expression of genes is one factor in the development of such diseases and conditions and the evaluation of gene expression patterns has become widely recognized as important to understanding the development and control of such diseases and conditions at the molecular level. To advance the understanding of genes and their relationship to disease, a number of methods have been developed for studying differential gene expression, e.g., DNA microarrays, expressed tag sequencing (EST), serial analysis of gene expression (SAGE), subtractive hybridization, subtractive cloning and differential display (DD) for mRNA, RNA-arbitrarily primed PCR (RAP-PCR), real-time PCR (RT-PCR), representational difference analysis (RDA), two-dimensional gel electrophoresis, mass spectrometry, and protein microarray based antibody-binding for proteins.

Due to the complexity of the biological pathways implicated in renal disease and the inherent molecular interactions and intercellular signaling processes, it is highly desirable to understand at a genetic level the interactions that are taking place. Detection of dysregulated genes in the early stages of loss of renal function in canines is helpful in understanding the biology of renal disease, especially glomerulonephritis on a genome-wide basis. The fact that gene dysregulation may be detected at an early stage of disease development in animals subjected to repeated ischemic injury is helpful in designing methods for diagnosing of, and devising and monitoring a treatment plan for, an abnormal loss of kidney function, renal failure, reduced glomerular filtration rate or glomerulonephritis, in a canine.

A more detailed understanding of the biological pathways involved through gene expression profiling will aid in the development of diagnostic procedures, reagents and test kits as well as salutary pharmaceutical, nutraceutical and nutritional (dietary) interventions in the disease pathways. These approaches may enable early detection and potentially prevention or treatment of the underlying kidney disorder, particularly glomerulonephritis, as well as in monitoring the prognosis of early stage renal failure and glomerulonephritis, especially in canines. Dysregulated genes involved in the pathology of such disorders may serve as important biomarkers for diagnosis and potentially prevention or treatment of the disorder and to optimize selection of appropriate pharmaceutical, nutraceutical and nutritional (dietary) interventions.

The level of gene expression and/or the determination of the level of functioning of an expressed gene product in a canine may be used to select an appropriate agent for therapeutic or prophylactic use. This data may be employed by the skilled worker in selecting appropriate drugs as agents for the prevention or treatment of renal diseases in canines through gene expression profiling. Gene expression data and analysis may also be used to select nutritional compositions, dietary supplements, and nutraceuticals having a salutary effect on kidney performance by utilizing biomarkers indicative of a healthy state of kidney functioning.

Only very limited work has been done to date in screening the canine genome for gene expression profiles in connection with the diagnosis of diseases in dogs. Certain work employing animal models has utilized cDNA array technologies to screen for gene expression in renal tissues associated with renal disease.

Studies in healthy populations of canines versus populations having a disease such as a kidney disease and loss of kidney function as described in this specification have not been extensively conducted. Little data is available with respect to the expression profile of the canine genome, especially with respect to the development of renal diseases in canines over time. Gene expression data contained in this specification identifies the genes associated with renal function in dogs. Such gene expression data enables development of compositions and methods for diagnosing of, devising and monitoring a treatment plan for, and monitoring the status of, a kidney disorder characterized by an abnormal loss of renal function, renal failure, reduced glomerular filtration rate or glomerulonephritis, in a canine, wherein the kidney disorder is detectable by utilizing at least one relevant biomarker isolated and measured from a biological test sample taken from such canine.

Gene expression data contained in the specification and examples enables a variety of desirable inventions based on the gene expression profiles described in the specification and examples of this patent application. The data permits identification and quantification of gene expression products as biomarkers of disease prevention, identification and treatment of the underlying renal disease. Gene expression data elicited as a result of the practice of the methods of the invention also permits monitoring the progression of such renal disease. These inventions further include genetic testing to identify susceptible subpopulations of animals likely to be afflicted with such renal disease, to identify optimal diets for the prevention or treatment of such renal diseases, to identify pharmaceutical, nutraceutical and nutritional (dietary) interventions based on the findings set forth on this specification in order to treat the underlying renal diseases. The inventions also include biomarkers for early disease detection, targeted therapeutics, diagnostic reagents and kits for the analysis of tissue and blood samples from canines susceptible to or having such a renal disease.

SUMMARY OF THE INVENTION

The present invention relates to compositions and methods for: diagnosing of, devising and monitoring a treatment plan for, and monitoring the status of a kidney disorder characterized by an abnormal loss of renal function, renal failure, reduced glomerular filtration rate or glomerulonephritis, in a canine, wherein the kidney disorder is detectable by utilizing at least one relevant biomarker isolated and measured from a biological test sample taken from such canine.

A relevant biomarker for practice of the compositions and methods of the present invention comprises an RNA transcript or its translation product taken from such biological test sample of such canine. A biological test sample for the practice of the method of the invention comprises a tissue sample of a kidney of such canine or a specimen of a biological fluid taken from such canine.

In particular, this invention relates to methods for: diagnosing of, devising and monitoring a treatment plan for, and monitoring the status of, a kidney disorder characterized by an abnormal loss of renal function, renal failure, reduced glomerular filtration rate or glomerulonephritis, in a canine, through use of gene expression analysis.

The present invention also relates to the identification of combinations of novel biomarkers for use in determining diagnosing of, devising and monitoring a treatment plan for, and monitoring the status of, a kidney disorder characterized by an abnormal loss of renal function, renal failure, reduced glomerular filtration rate or glomerulonephritis, in a canine.

The invention additionally relates to compositions, reagents and kits for carrying out the specified methods.

The invention is based, in part, on the discovery that particular gene expression profiles in canines correlate with a change in such animal from a normal to an abnormal biological process in the kidney that may lead to a decline in renal function over time. A correlation of a particular gene expression profile with the risk of experiencing a decline in renal function can be predicted, detected and diagnosed in a canine without rendering a conventional clinical diagnosis based on art-recognized clinical signs and symptoms of renal disease. An altered gene expression profile in a canine is, therefore, predictive of a decline in renal function, as might otherwise be diagnosed at a later time by art-recognized measurements of renal function. Such art-recognized measurements of renal function typically may include, for example, one of the following measurements: glomerular filtration rate, creatinine clearance rate, urinary protein levels, serum creatinine levels, urinary creatinine levels, blood urea nitrogen (BUN) levels, radioisotope metabolic labeling, soft tissue imaging, including sonography, magnetic resonance imaging and/or computed tomography. Non-intrusive assays such as serum creatinine and BUN levels typically show poor correlation with kidney histopathology and generally would not be predictive of future changes in the kidney.

The methods of evaluating a canine to diagnose a kidney disorder involve evaluating the gene expression level or activity of one or more of the following genes or the expression (translation) product of such genes in a canine, selected from the group consisting of: secreted frizzled-related protein 2 (sFRP2); matrilin-2 (Matn2); lumican (LUM); collagen alpha 1 (III) chain, variant 12 (COL3A1); decorin (DCN); retinol binding protein 4 (rbp4); MMP-9; clusterin (CLU); transferrin (TF); Apo-C-1 (ApoC1); and inhibin beta A (INHBA).

The methods of evaluating a canine to diagnose a kidney disorder involve evaluating the gene expression level or activity of one or more of the following genes or the expression product of such gene in a canine selected from the group consisting of: secreted frizzled-related protein 2 (sFRP2) or matrilin-2 (Matn2); and optionally, a second group consisting of: lumican (LUM); decorin (DCN); collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA).

The biomarkers useful in the practice of the present invention are: lumican (LUM); collagen alpha 1 (III) chain, variant 12 (COL3A1); decorin (DCN); secreted frizzled-related protein 2 (sFRP2); matrilin-2 (Matn2); retinol binding protein 4 (rbp4); MMP-9; clusterin (CLU); transferrin (TF); Apo-C-1 (ApoC1); and inhibin beta A (INHBA), as more fully described below and in the sequence listings appended to this specification.

Canine lumican. Affymetrix probe CfaAFFx.10198.1.S1_s_at corresponds to NCBI Reference Sequence: XP_539716.1, accession XP_539716, predicted to be similar to Lumican precursor (keratin sulfate proteoglycan lumican [KSPG lumican]) [Canis familiaris]. Canine lumican is a 338 amino acid leucine-rich repeat protein coded by XM_539716.2 at GeneID:482599 [SEQ. ID. NO: 1].

The terms "Lumican" and "LUM" and "Lum" denote a protein having substantially the amino acid sequence as shown in SEQ. ID. NO: 1. Preferably, lumican is a protein substantially consisting of the amino acid sequence as shown in SEQ. ID. NO: 1. Lumican also includes protein variants of the sequence as shown in SEQ. ID. NO: 1, such as allelic variants and other mutations such as substitutions, additions and/or deletions. The term lumican also refers to the nucleic acid sequence encoding the protein. The sequence corresponds to XM_539716.2 and appended SEQ. ID. NO: 12. Lumican also refers to nucleic acid sequences that hybridize to SEQ. ID. NO: 12 and to fragments of SEQ. ID. NO: 12.

Canine collagen alpha 1 (III), variant 12 (COL3A1). Affymetrix probe CfaAffx.22804.1S1_s_at corresponds to NCBI Reference Sequence: XP_863148.1, accession XP_863148, predicted to be similar to Collagen alpha (III) chain precursor isoform 12. Canine COL3A1 is a 1446 amino acid protein coded by XM_863148.1 at GeneID: 478835 [SEQ. ID. NO: 2].

The terms "Collagen alpha (III) chain precursor isoform 12," "Col3a1" and "COL3A1" denote a protein having substantially the amino acid sequence as shown in SEQ. ID. NO: 2. Preferably, COL3A1 is a protein substantially consisting of the amino acid sequence as shown in SEQ. ID. NO: 2. COL3A1 also includes protein variants of the sequence as shown in SEQ. ID. NO: 2, such as allelic variants and other mutations such as substitutions, additions and/or deletions. The term COL3A1 also refers to the nucleic acid sequence encoding the protein. The sequence corresponds to XM_863148.1 and appended SEQ. ID. NO: 13. COL3A1 also refers to nucleic acid sequences that hybridize to SEQ. ID. NO: 13 and to fragments of SEQ. ID. NO: 13.

Canine decorin (DCN). Affymetrix probe Cfa.6065.1.A1_s_at corresponds to NCBI Reference Sequence: NP_001003228.1, accession NP_001003228, decorin [Canis lupus familiaris]. Canine decorin is a 360 amino acid leucine-rich repeat protein coded by NM_001003228.1 at GeneID: 403904 [SEQ. ID. NO: 3].

The terms "Decorin," "Dcn" and "DCN" denote a protein having substantially the amino acid sequence as shown in SEQ. ID. NO: 3. Preferably, decorin is a protein substantially consisting of the amino acid sequence as shown in SEQ. ID. NO: 3. Decorin also includes protein variants of the sequence as shown in SEQ. ID. NO: 3, such as allelic variants and other mutations such as substitutions, additions and/or deletions. The term decorin also refers to the nucleic acid sequence encoding the protein. The sequence corresponds to NM_001003228.1 and appended SEQ. ID. NO: 14. Decorin also refers to nucleic acid sequences that hybridize to SEQ. ID. NO: 14 and to fragments of SEQ. ID. NO: 14.

Canine secreted frizzled-related protein 2 (sFRP2). Affymetrix probe Cfa.1200.1.S1_s_at corresponds to NCBI Reference Sequence: NP_001002987.1, accession NP_001002987 XP_532695, secreted frizzled-related protein 2 (sFRP2) [Canis lupus familiaris]. Canine secreted frizzled-related protein 2 (sFRP2) is a 294 amino acid protein coded by NM_001002987.1 at GeneID: 475471 [SEQ. ID. NO: 4].

The terms "secreted frizzle-related protein 2," "SFRP2," and "sFRP2" denote a protein having substantially the amino acid sequence as shown in SEQ. ID. NO: 4. Preferably, sFRP2 is a protein substantially consisting of the amino acid sequence as shown in SEQ. ID. NO: 4. sFRP2 also includes protein variants of the sequence as shown in SEQ. ID. NO: 4, such as allelic variants and other mutations such as substitutions, additions and/or deletions. The term sFRP2 also refers to the nucleic acid sequence encoding the protein. The sequence corresponds to NM_001002987.1 and appended SEQ. ID. NO: 15. sFRP2 also refers to nucleic acid sequences that hybridize to SEQ. ID. NO: 15 and to fragments of SEQ. ID. NO: 15.

Canine matrilin-2 (Matn2). Affymetrix probe Cfa.9487.1A1_at corresponds to NCBI Reference Sequence: XP_5485552.2, accession NP_5485552, similar to matrilin 2 isoform a precursor [Canis lupus familiaris]. Canine matrilin-2 is a 978 amino acid protein coded by XM_5485552.2 at GeneID: 491431 [SEQ. ID. NO: 5].

The terms "matrilin 2 isoform a precursor," "matrilin 2" and "Matn2" denote a protein having substantially the amino acid sequence as shown in SEQ. ID. NO: 5. Preferably, Matn2 is a protein substantially consisting of the amino acid sequence as shown in SEQ. ID. NO: 5. Matn2 also includes protein variants of the sequence as shown in SEQ. ID. NO: 5, such as allelic variants and other mutations such as substitutions, additions and/or deletions. The term Matn2 also refers to the nucleic acid sequence encoding the protein. The sequence corresponds to XM_5485552.2 and appended SEQ. ID. NO: 16. Matn2 also refers to nucleic acid sequences that hybridize to SEQ. ID. NO: 16 and to fragments of SEQ. ID. NO: 16.

Canine retinol binding protein 4 (rbp4). Affymetrix probe Cfa.15489.1.S1_at corresponds to NCBI Reference Sequence: XP_534969.2 accession NP_534969, similar to retinol binding protein 4, plasma precursor (rbp4) [*Canis lupus* familiaris]. Canine retinol binding protein 4 (rbp4) is a 267 amino acid protein coded by XM_534969.2 at GeneID: 477775 [SEQ. ID. NO: 6].

The terms "retinol binding protein 4," "plasma precursor," "retinol" and "Rbp4" denote a protein having substantially the amino acid sequence as shown in SEQ. ID. NO: 6. Preferably, Rbp4 is a protein substantially consisting of the amino acid sequence as shown in SEQ. ID. NO: 6. Rbp4 also includes protein variants of the sequence as shown in SEQ. ID. NO: 6, such as allelic variants and other mutations such as substitutions, additions and/or deletions. The term Rbp4 also refers to the nucleic acid sequence encoding the protein. The sequence corresponds to XM_534969.2 and appended SEQ. ID. NO: 17. Rbp4 also refers to nucleic acid sequences that hybridize to SEQ. ID. NO: 17 and to fragments of SEQ. ID. NO: 17.

Canine matrix metalloproteinase 9 (MMP-9). Affymetrix probe Cfa.3470.1S1_at corresponds to NCBI Reference Sequence: NP_001003219.1 accession NP_001003219, matrix metalloproteinase 9 [*Canis lupus* familiaris]. Canine matrix metalloproteinase 9 (MMP9) is a 704 amino acid protein coded by NM_001003219.1 at GeneID: 403885 [SEQ. ID. NO: 7].

The terms "matrix metalloproteinase 9" and "MMP9" denote a protein having substantially the amino acid sequence as shown in SEQ. ID. NO: 7. Preferably, MMP9 is a protein substantially consisting of the amino acid sequence as shown in SEQ. ID. NO: 7. MMP9 also includes protein variants of the sequence as shown in SEQ. ID. NO: 7, such as allelic variants and other mutations such as substitutions, additions and/or deletions. The term MMP9 also refers to the nucleic acid sequence encoding the protein. The sequence corresponds to NM_001003219.1 and appended SEQ. ID. NO: 18. MMP9 also refers to nucleic acid sequences that hybridize to SEQ. ID. NO: 18 and to fragments of SEQ. ID. NO: 18

Canine clusterin (CLU). Affymetrix probe Cfa1254.S1_s_at corresponds to NCBI Reference Sequence: NM_001003370.1 accession NM_001003370 canine clusterin. Canine clusterin is a 445 amino acid protein coded by NM_001003370.1 at GeneID: 442971 [SEQ. ID. NO: 8].

The terms "clusterin" and "Clu" denote a protein having substantially the amino acid sequence as shown in SEQ. ID. NO: 8. Preferably, clusterin is a protein substantially consisting of the amino acid sequence as shown in SEQ. ID. NO: 8. Clusterin also includes protein variants of the sequence as shown in SEQ. ID. NO: 8, such as allelic variants and other mutations such as substitutions, additions and/or deletions. The term clusterin also refers to the nucleic acid sequence encoding the protein. The sequence corresponds to NM_001003370.1 and appended SEQ. ID. NO: 19 Clusterin also refers to nucleic acid sequences that hybridize to SEQ. ID. NO: 19 and to fragments of SEQ. ID. NO: 19

Canine transferrin (TF). Affymetrix probe Cfa2217.1.A1_at corresponds to NCBI Reference Sequence: XP_534268.2 accession XP_534268 similar to canine serotransferrin precursor (Transferrin) isoform 1. Canine transferrin is a 705 amino acid protein coded by XM_534268.2 at GeneID: 477072 [SEQ. ID. NO: 9].

The terms "canine serotransferrin precursor (Transferrin) isoform 1," "transferrin" and "TF" denote a protein having substantially the amino acid sequence as shown in SEQ. ID. NO: 9. Preferably, transferrin is a protein substantially consisting of the amino acid sequence as shown in SEQ. ID. NO: 9. Transferrin also includes protein variants of the sequence as shown in SEQ. ID. NO: 9, such as allelic variants and other mutations such as substitutions, additions and/or deletions. The term transferrin also refers to the nucleic acid sequence encoding the protein. The sequence corresponds to XM_534268.2 and appended SEQ. ID. NO: 20 Transferrin also refers to nucleic acid sequences that hybridize to SEQ. ID. NO: 20 and to fragments of SEQ. ID. NO: 20.

Canine apolipoproetin C-1 (ApoC1). Affymetrix probe Cfa1254.S1_s_at corresponds to NCBI Reference Sequence: XP_533643.2 accession XP_533643 similar to canine apolipoproetin C-I precursor (ApoCI). Canine apolipoproetin C-I (ApoCI) is an 88 amino acid protein coded by NM_533643.2 at GeneID: 113459 [SEQ. ID. NO: 10].

The terms "apolipoproetin C-1" and "ApoC1" denote a protein having substantially the amino acid sequence as shown in SEQ. ID. NO: 10. Preferably, transferrin is a protein substantially consisting of the amino acid sequence as shown in SEQ. ID. NO: 10. ApoC1 also includes protein variants of the sequence as shown in SEQ. ID. NO: 10, such as allelic variants and other mutations such as substitutions, additions and/or deletions. The term ApoC1 also refers to the nucleic acid sequence encoding the protein. The sequence corresponds to NM_533643.2 and appended SEQ. ID. NO: 21 ApoC1 also refers to nucleic acid sequences that hybridize to SEQ. ID. NO: 21 and to fragments of SEQ. ID. NO: 21.

Inhibin beta A (INHBA). Affymetrix probe Cfa596.1A1_at corresponds to NCBI Reference Sequence: XP_540364 accession XP_540364 similar to inhibin beta A chain precursor (INHBA) (Activin beta-A-chain) (erythroid differentiation protein; EDF). Canine inhibin beta A chain precursor (INHBA) is a 424 amino acid protein coded by XM_540364.2 at GeneID: 483245 [SEQ. ID. NO: 11].

The terms "Inhibin beta A chain precursor" and "INHBA" denote a protein having substantially the amino acid sequence as shown in SEQ. ID. NO: 11. Preferably, inhibin is a protein substantially consisting of the amino acid sequence as shown in SEQ. ID. NO: 11. Inhibin also includes protein variants of the sequence as shown in SEQ. ID. NO: 11, such as allelic variants and other mutations such as substitutions, additions and/or deletions. The term inhibin also refers to the nucleic acid sequence encoding the protein. The sequence corresponds to XM_540364.2 and appended SEQ. ID. NO: 22 Transferrin also refers to nucleic acid sequences that hybridize to SEQ. ID. NO: 22 and to fragments of SEQ. ID. NO: 22.

In a preferred embodiment of the present invention, a method for diagnosing a kidney disorder in a canine comprises the steps of: (a) measuring the level of expression of at least one biomarker in a biological sample from the canine, wherein the at least one biomarker is selected from secreted frizzle-related protein-2 (SFRP2); matrilin-2 (Matn2); lumican (LUM); decorin (DCN); collagen alpha 1 (III) chain, variant 12 (COL3A1); retinol binding protein 4

(rbp4); MMP-9; clusterin (CLU); transferrin (TF); Apo-C-1 (ApoC1); and inhibin beta A (INHBA); and (b) identifying the canine as having a kidney disorder wherein differences in expression of the one or more biomarkers in the sample relative to a control value for expression in a sample from a normal animal indicates the existence of a kidney disorder.

In a another preferred embodiment of the present invention, the canine has normal kidney function as defined by art-recognized clinical measurements, e.g., glomerular flirtation rate, creatinine clearance, urinary protein levels, blood creatinine levels, urinary creatinine levels and/or blood urea nitrogen levels and the methods of the invention may be used to detect and diagnose in such canine a change from a normal state to an abnormal state leading to a kidney disorder characterized by reduced renal function, renal failure, reduced glomerular filtration rate and glomerulonephritis.

In another preferred embodiment, an elevated level of activity or expression of one or more genes in a canine selected from the group consisting of: lumican (LUM); collagen alpha 1 (III) chain, variant 12 (COL3A1); decorin (DCN); secreted frizzle-related protein 2 (sFRP2); and matrilin-2 (Matn2) correlates with a kidney disorder characterized by an abnormal loss of renal function, renal failure, reduced glomerular filtration rate or glomerulonephritis. The level of activity or expression of one or more genes may be determined by measuring the expression product of such genes which may be a polynucleotide or a polypeptide or protein, typically an RNA transcript or its translation product.

In another preferred embodiment, differential expression of one or more genes in a canine selected from at least one RNA transcript or its translation product selected from the group consisting of: secreted frizzled-related protein 2 (sFRP2); matrilin-2 (Matn2); lumican (LUM); decorin (DCN); collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA) correlates with an abnormal loss of renal function, renal failure, reduced glomerular filtration rate or glomerulonephritis.

In another preferred embodiment, differential expression of one or more genes in a canine selected from a first group of at least one RNA transcript or its translation product selected from the group consisting of: secreted frizzled-related protein 2 (sFRP2) orrmatrilin-2 (Matn2); and optionally, a second group of at least one RNA transcript or its translation product selected from the group consisting of: lumican (LUM); decorin (DCN); collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA) correlates with an abnormal loss of renal function, renal failure, reduced glomerular filtration rate or glomerulonephritis. It is to be understood that the present invention contemplates combination of biomarkers comprising genes or their expression products that are both (i) selected from a first group of at least one RNA transcript or its translation product selected from the group consisting of: secreted frizzled-related protein 2 (sFRP2) or matrilin-2 (Matn2); and optionally, a second group of at least one RNA transcript or its translation product selected from the group consisting of: lumican (LUM); decorin (DCN); collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA); as well as (ii) selected from a first group of at least one RNA transcript or its translation product selected from the group consisting of: secreted frizzled-related protein 2 (sFRP2) or matrilin-2 (Matn2); and a second group of at least one RNA transcript or its translation product selected from the group consisting of: lumican (LUM); decorin (DCN); collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA). Embodiments of the invention contemplate constructing panels of biomarkers from various combinations of the two groupings of genes and their expression products.

In another preferred embodiment, the invention encompasses measurement and correlation of differential expression in a canine of one or more genes selected from at least one RNA transcript or its translation product selected from the group consisting of: secreted frizzled-related protein 2 (sFRP2); matrilin-2 (Matn2); lumican (LUM); decorin (DCN); collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA), with accelerated or early loss of renal function in canines as evidenced by an abnormal process leading to a kidney disorder characterized by reduced renal function, reduced glomerular filtration rate, glomerulonephritis or renal failure.

In one aspect the invention includes contacting a tissue sample or bodily fluid specimen with an agent that detects in a canine one or more genes or the expression product of such one or more genes selected from at least one RNA transcript or its translation product selected from the group consisting of: secreted frizzled-related protein 2 (sFRP2); matrilin-2 (Matn2); lumican (LUM); decorin (DCN); collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA). The agent can be an antibody or a nucleic acid probe used in conjunction with conventional assay means such as immobilization on a solid phase, microtiter wells, tubes, dipsticks or other conventional means.

Another embodiment of the method of the invention encompasses use of conventional assay means to determine gene expression in a canine either alone or in conjunction with gene expression array displays employing polypeptides and/or polynucleotides, such conventional assay means comprising one or more of ELISA, RIA, immunoblot assays, in situ hybridization, Northern blot analysis, Western blot analysis and Luminex X-Map® analysis.

Another embodiment of the invention encompasses diagnosing a kidney disorder characterized by an abnormal loss of renal function, renal failure, reduced glomerular filtration rate or glomerulonephritis over time by determining gene expression profiles for one or more genes or their expression products selected from at least one RNA transcript or its translation product selected from the group consisting of: secreted frizzled-related protein 2 (sFRP2); matrilin-2 (Matn2); lumican (LUM); decorin (DCN); collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA) in conjunction with one or more conventional diagnostic measurements selected from the group consisting of: determining levels of albumin, serum cystatin C, blood creatinine, urinary creatinine, creatinine clearance, urinary protein, blood urea nitrogen and glomerular filtration rate, to choose a course of treatment for such canine.

In another embodiment, the invention features a kit for diagnosing and/or monitoring a kidney disorder in a canine over time, the kit comprising one or more agents capable of detecting expression profiles for one or more genes or their expression products selected from at least one RNA transcript or its translation product selected from the group consisting of: secreted frizzled-related protein 2 (sFRP2); matrilin-2 (Matn2); lumican (LUM); decorin (DCN); collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA), and instructions for using said one or more agents to evaluate the risk of such canine developing a kidney disorder characterized by an abnormal loss of renal function, renal failure, reduced glomerular filtration rate or glomerulonephritis over time.

In another aspect, the invention includes contacting a tissue sample or bodily fluid specimen with an agent that detects in one or more genes or their expression products selected from at least one RNA transcript or its translation product selected from the group consisting of: secreted frizzled-related protein 2 (sFRP2); matrilin-2 (Matn2); lumican (LUM); decorin (DCN); collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA). The agent can be an antibody or a nucleic acid probe used in conjunction with conventional assay means such as immobilization on a solid phase, microtiter wells, tubes, dipsticks or other conventional means.

Particularly preferred embodiments of the present invention follow below. In each of the following embodiments, the present invention contemplates a test sample comprising either solid kidney tissue samples, or samples of biological fluids from a canine. Differential expression of the recited genes contemplates a significant difference in absolute terms. In preferred embodiments the differential expression may be greater than about 1.1, 1.2, 1.3, 1.4, 1.5, 1.6, 1.7, 1.8, 1.9, 2.0, 2.1, 2.2, 2.3, 2.4, 2.5, or 3.0 fold or greater. Especially preferred differential expression values are greater than about 2 fold or one standard deviation around the mean. Also, the embodiments of the invention may employ a variety of art-recognized detection means, including an array of one or more hybridization probes, panels of one or more antibodies and combinations of these technologies. When immunoassays are desired, the skilled worker can select among many art-recognized techniques, including immunoassays selected from the group consisting of a competitive binding assay, a non-competitive binding assay, a radioimmunoassay, an enzyme linked immunosorbent assay (ELISA), a sandwich assay, a precipitin reaction, a gel diffusion immunodiffusion assay, an agglutination assay, a fluorescent immunoassay, chemiluminescence immunoassay, immunoPCR immunoassay, a protein A or protein G immunoassay and an immunoelectrophoresis assay. When conventional diagnostic measurements are specified, these may be selected from the group consisting of: determining levels of albumin, serum cystatin C, blood creatinine, urinary creatinine, creatinine clearance, urinary protein, blood urea nitrogen and glomerular filtration rate In addition, the methods and compositions of the invention contemplate utilizing at least one RNA transcript or its translation product which may be an altered form of the gene or its translation product.

A still further embodiment of the invention comprises a method for diagnosing a kidney disorder in a canine, comprising the steps of: (a) measuring the level of expression of at least one biomarker in a biological sample from the canine, wherein the at least one biomarker is selected from at least one gene or the translation product of such gene selected from the group consisting of secreted frizzle-related protein-2 (SFRP2); matrilin-2 (Matn2); lumican (LUM); decorin (DCN); collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA); and (b) identifying the canine as having a kidney disorder wherein difference in expression of the one or more biomarkers in the sample relative to a control value for expression in a sample from a normal animal indicates the existence of a kidney disorder.

Another embodiment comprises a kit for the diagnosis, prognosis or monitoring a kidney disorder in a canine, comprising at least one or more agent capable of detecting at least one or more RNA transcript or its translation product selected from a first group of at least one gene or the translation product of such gene selected from the group consisting of: secreted frizzle-related protein-2 (SFRP2); matrilin-2 (Matn2); lumican (LUM), decorin (DCN), collagen alpha 1 (III) chain, variant 12 (COL3A1); retinol binding protein 4 (rbp4); MMP-9; clusterin (CLU); transferrin (TF); Apo-C-1 (ApoC1); and inhibin beta A (INHBA); and instructions for using such at least one or more agent to measure the expression of the one or more biomarkers and to diagnose a kidney disease in such canine.

In a further aspect, the invention relates to compositions comprising one or more nucleic acid probes that specifically hybridize to a nucleic acid, or fragment thereof, encoding a biomarker of the present invention selected from the group consisting of: secreted frizzle-related protein-2 (SFRP2); matrilin-2 (Matn2); lumican (LUM); decorin (DCN); collagen alpha 1 (III) chain, variant 12 (COL3A1); retinol binding protein 4 (rbp4); matrix metalloproteinase 9 (MMP9); clusterin (CLU); transferrin (TF); Apo-C-1 (ApoC1); and inhibin beta A (INHBA).

In an additional aspect, the invention relates to compositions comprising antibodies that specifically bind to a polypeptide encoded by a gene expressing a biomarker of the present invention selected from the group consisting of: secreted frizzle-related protein-2 (SFRP2); matrilin-2 (Matn2); lumican (LUM); decorin (DCN); collagen alpha 1 (III) chain, variant 12 (COL3A1); retinol binding protein 4 (rbp4); matrix metalloproteinase 9 (MMP9); clusterin (CLU); transferrin (TF); Apo-C-1 (ApoC1); and inhibin beta A (INHBA).

It is further contemplated herein that the methods of the present invention may be used in combination with traditional diagnostic techniques that are able to detect the physical and morphological characteristics of kidney disorders. Thus, for example, the characterization of differential expression in genes for kidney in cells obtained from a tissue samples or bodily fluid specimens of a canine may be combined with conventional diagnostic (e.g., radiological) techniques in order to corroborate a diagnosis of a kidney disorder in a canine, including, for example, glomerulonephritis.

The invention also relates to kits to diagnose an abnormal kidney disorder in a canine comprising components that can be used to detect expression of the biomarkers of the present invention, including, but not limited to, the compositions and microarrays described herein.

A further aspect of the invention is a method for diagnosis and/or prognosis of kidney disorder in a canine, wherein the method comprises the steps of: obtaining at least one tissue sample or bodily fluid specimen from the animal; determining the amount of one or more biomarkers selected from Table 3 in said at least one sample or specimen obtained from the animal, wherein said biomarker is a polypeptide, protein, RNA, DNA, polynucleotide or metabolite thereof.

Yet another embodiment of the invention is a kit for diagnosis and/or prognosis of a kidney disorder in a canine, particularly for carrying out the method for diagnosis and/or prognosis of glomerulonephritis in a canine wherein the method comprises the steps of: obtaining at least one tissue sample or bodily fluid specimen from the animal; determining the amount of one or more biomarkers selected from Table 3 in said at least one sample or specimen obtained from the animal, wherein said biomarker is a polypeptide, protein, RNA, DNA, polynucleotide or metabolite thereof, and optionally, further comprising a detectable agent linked to said biomarker.

A still further embodiment of the invention is a reagent for diagnosis and/or prognosis of glomerulonephritis in a canine particularly for carrying out the method for diagnosis and/or prognosis of glomerulonephritis in a canine, wherein the method comprises the steps of: obtaining at least one tissue sample or bodily fluid specimen from the animal; determining the amount of one or more biomarkers selected from Table 3 in said at least one sample or specimen obtained from a canine, wherein said biomarker is a polypeptide, protein, RNA, DNA, polynucleotide or metabolite thereof, and optionally further comprising a detectable agent linked to said biomarker.

A further aspect of the invention is a method for diagnosis and/or prognosis of kidney disorder in a canine, wherein the method comprises the steps of: obtaining at least one tissue sample or bodily fluid specimen from the animal; determining the amount of one or more biomarkers selected from Tables 3 and 4 in said at least one sample or specimen obtained from the animal, wherein said biomarker is a polypeptide, protein, RNA, DNA, polynucleotide or metabolite thereof.

Another embodiment of the invention is the use of one or more polypeptides, proteins, RNAs, DNAs, polynucleotides or metabolites thereof selected from the group consisting of secreted frizzle-related protein-2 (SFRP2); matrilin-2 (Matn2); lumican (LUM); decorin (DCN); collagen alpha 1 (III) chain, variant 12 (COL3A1); retinol binding protein 4 (rbp4); matrix metalloproteinase 9 (MMP9); clusterin (CLU); transferrin (TF); Apo-C-1 (ApoC1); and inhibin beta A (INHBA) as a biomarker for diagnosis and/or prognosis of a kidney disorder, particularly for forming a kit for diagnosis or prognosis of a kidney disorder in a canine.

Another embodiment of the invention is the use of one or more polypeptides, proteins, RNAs, DNAs, polynucleotides or metabolites thereof selected from the group consisting of: secreted frizzle-related protein-2 (SFRP2); matrilin-2 (Matn2); lumican (LUM); decorin (DCN); collagen alpha 1 (III) chain, variant 12 (COL3A1); retinol binding protein 4 (rbp4); matrix metalloproteinase 9 (MMP9); clusterin (CLU); transferrin (TF); Apo-C-1 (ApoC1); and inhibin beta A (INHBA) as a biomarker for diagnosis and/or prognosis of a kidney disorder, particularly for forming a kit for diagnosis or prognosis of a kidney disorder in a canine.

Yet another embodiment is such kit, wherein the reagents and equipment comprise DNA microarray analysis materials including oligonucleotide microarray, c-DNA microarray, and focused gene chip, or a combination thereof.

Another embodiment of the invention is a method of assessing the progression of a course of nutritional management for a canine suffering from a kidney disorder, the method comprising (a) measuring a first level of one or more biomarker polypeptides, proteins, RNAs, DNAs, polynucleotides or metabolites thereof selected from the group consisting of: secreted frizzle-related protein-2 (SFRP2); matrilin-2 (Matn2); lumican (LUM); decorin (DCN); collagen alpha 1 (III) chain, variant 12 (COL3A1); retinol binding protein 4 (rbp4); matrix metalloproteinase 9 (MMP9); clusterin (CLU); transferrin (TF); Apo-C-1 (ApoC1); and inhibin beta A (INHBA) in a tissue sample or a specimen of bodily fluid from said canine at a first point in time during the course of treatment, (b) measuring a second level of said biomarker in said sample or specimen from said canine at a second point in time during the course of treatment, and (c) comparing the measurements of the biomarker at said first point and said second point; wherein expression of the biomarker has at least about a 1.0, 1.1, 1.2, 1.3, 1.4, 1.5, 1.6, 1.7, 1.8, 1.9, 2.0, 2.5, or 3.0 fold differential or greater difference in gene expression compared with expression in a cell of a control animal.

Still another embodiment of the invention is a method for identifying a plurality of genes that are differentially expressed between tissue samples or specimens of a bodily fluid for use in an informative array, comprising: providing a first set of heterogeneous nucleic acid probes derived from a first tissue sample; providing a second set of heterogeneous nucleic acid probes derived from a second tissue sample; hybridizing a nucleic acid array comprising a plurality of sequences derived from genes of a biological process with the first set of probes and determining a first level of expression for sequences of the array; hybridizing the array with said second set of probes and determining a second level of expression for sequences of the array; identifying a plurality of genes that are differentially expressed in said biological process by comparing the first level of expression with said second level of expression for hybridized sequences; and establishing a ranking of the identified genes by a step selected from the group of steps consisting of: determining an absolute value of the difference between the first level of expression and the second level of expression, and ranking genes having a higher difference over genes having a lower difference; and determining a standard deviation of the difference between the first level of expression and the second level of expression, and ranking genes having a higher standard deviation over genes having a lower standard deviation, wherein the genes are selected from the group consisting of: secreted frizzle-related protein-2 (SFRP2); matrilin-2 (Matn2); lumican (LUM); decorin (DCN); collagen alpha 1 (III) chain, variant 12 (COL3A1); retinol binding protein 4 (rbp4); matrix metalloproteinase 9 (MMP9); clusterin (CLU); transferrin (TF); Apo-C-1 (ApoC1); and inhibin beta A (INHBA).

Another embodiment of the invention is a method for converting a nucleic acid array into an informative array, comprising: providing a first set of heterogeneous nucleic acid probes derived from a first tissue sample; providing a different, second set of heterogeneous nucleic acid probes derived from a second tissue sample; hybridizing a nucleic acid array comprising a plurality of sequences with the first set of probes and determining a first level of expression for sequences of the array; hybridizing the array with said second set of probes and determining a second level of expression for sequences of the array; identifying a plurality of genes that are differentially expressed in said biological process based on a difference between the first level of expression and the second level of expression for identified genes, by a step selected from the group of steps consisting of: determining an absolute value for the difference between the first level of expression and the second level of expression, and ranking genes having a higher difference over genes having a lower difference; and determining a standard deviation of the difference between the first level of expression and the second level of expression, and ranking genes having a higher standard deviation over genes having a lower standard deviation; and selecting genes from the plurality of identified differentially expressed genes for inclusion on the informative array, wherein said genes are selected from the group consisting of: secreted frizzle-related protein-2 (SFRP2) and matrilin-2 (Matn2); and, optionally, one or more genes selected from the group consisting of: lumican (LUM); decorin (DCN); collagen alpha 1 (III) chain, variant 12 (COL3A1); retinol binding protein 4 (rbp4); matrix metalloproteinase 9 (MMP9); clusterin (CLU); transferrin (TF); Apo-C-1 (ApoC1); and inhibin beta A (INHBA).

Another embodiment of the invention is a method of determining the efficacy of a treatment for a kidney disorder, comprising the steps of: (a) providing a biological sample from a canine affected by a kidney disorder, who has been subjected to said treatment, (b) determining the level in said sample of one or more biomarkers for glomerulonephritis, to create an expression profile for said canine, and (c) comparing said expression profile with: i) a comparable expression profile obtained from said test canine before initiation of said treatment, and/or ii) a comparable expression profile obtained from said test canine at an earlier stage of said treatment, and/or iii) a comparable expression profile characteristic of a subject who is unaffected by a kidney disorder, wherein the one or more biomarkers for a kidney disorder, comprise expression products of one or more gene selected from the group consisting of secreted frizzle-related protein-2 (SFRP2) and matrilin-2 (Matn2); and, optionally, one or more genes selected from the group consisting of: lumican (LUM); decorin (DCN); collagen alpha 1 (III) chain, variant 12 (COL3A1); retinol binding protein 4 (rbp4); matrix metalloproteinase 9 (MMP9); clusterin (CLU); transferrin (TF); Apo-C-1 (ApoC1); and inhibin beta A (INHBA).

Other and further objects, features, and advantages of the present invention will be readily apparent to those skilled in the art.

DETAILED DESCRIPTION OF THE INVENTION

As used herein, an abnormal canine is a canine that has a risk of developing, predisposition for, or an abnormal loss of kidney function, renal failure, reduced glomerular filtration rate or glomerulonephritis, wherein the abnormality is detectable by utilizing at least one relevant biomarker isolated and measured from a biological specimen taken from such canine.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 5 should be considered to have specifically disclosed subranges such as from 1 to 3, from 1 to 4, from 2 to 4, from 2 to 5, from 3 to 5 etc., as well as individual numbers within that range, for example, 1, 2, 3, 4, and 5. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label.

The present invention also contemplates many uses for polymers attached to solid substrates. These uses include gene expression monitoring, profiling, library screening, genotyping and diagnostics.

Those skilled in the art will recognize that the products and methods embodied in the present invention may be applied to a variety of systems, including commercially available gene expression monitoring systems involving nucleic acid probe arrays, membrane blots, microwells, beads and sample tubes, constructed with various materials using various methods known in the art. Accordingly, the present invention is not limited to any particular environment, and the following description of specific embodiments of the present invention are for illustrative purposes only.

The gene expression monitoring system, in a preferred embodiment, may comprise a nucleic acid probe array (including an oligonucleotide array, a cDNA array, a spotted array, and the like), membrane blot (such as used in hybridization analysis such as Northern, Southern, dot, and the like), or microwells, sample tubes, beads or fibers (or any solid support comprising bound nucleic acids). The gene expression monitoring system may also comprise nucleic acid probes in solution.

The present invention also contemplates sample preparation involving amplification. A genomic sample may be amplified by a variety of mechanisms, some of which may employ PCR. The sample may be amplified on the array. Other suitable amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA).

The gene expression monitoring system according to the present invention may be used to facilitate a comparative analysis of expression in different cells or tissues, different subpopulations of the same cells or tissues, different physiological states of the same cells or tissue, different developmental stages of the same cells or tissue, or different cell populations of the same tissue. In a preferred embodiment, the proportional amplification methods of the present invention can provide reproducible results (i.e., within statistically significant margins of error or degrees of confidence) sufficient to facilitate the measurement of quantitative as well as qualitative differences in the tested samples.

The term "antibody" means any immunoglobulin that binds to a specific antigen, including IgG, IgM, IgA, IgD, and IgE antibodies. The term includes polyclonal, monoclonal, monovalent, humanized, heteroconjugate, antibody compositions with polyepitopic specificity, chimeric, bispecific antibodies, diabodies, single-chain antibodies and antibody fragments such as Fab, Fab', F(ab')$_2$, and Fv, or other antigen-binding fragments.

The term "array" means an ordered arrangement of at least two probes on a substrate. At least one of the probes is a control or standard and at least one of the probes is a diagnostic probe. The arrangement of from about two to about 40,000 probes on a substrate assures that the size and signal intensity of each labeled complex formed between a probe and a sample polynucleotide or polypeptide is individually distinguishable. The collection of molecules deposited on the array may be prepared either synthetically or biosynthetically. The array may take a variety of forms including libraries of soluble molecules, libraries of compounds tethered to resin beads, silica chips or other solid supports. The nucleic acid array may include libraries of nucleic acids which can be prepared by spotting nucleic acids in essentially any length (for example, from 1 to about 1,000 nucleotides in length) onto a substrate. A nucleic acid probe array preferably comprises nucleic acids bound to a substrate in known locations. In other embodiments, the system may include a solid support or substrate, such as a membrane, filter, microscope slide, microwell, sample tube, bead, bead array, or the like. The solid support may be made of various materials, including paper, cellulose, nylon, polystyrene, polycarbonate, plastics, glass, ceramic, stainless steel, or the like. The solid support may preferably have a rigid or semi-rigid surface, and may preferably be spherical (e.g., bead) or substantially planar (e.g., flat surface) with appropriate wells, raised regions, etched trenches, or the like. The solid support may also include a gel or matrix in which nucleic acids may be embedded.

The term "biomarker" refers to genes and gene products encoded by the gene of the invention, i.e., where the gene has been determined to have been differentially regulated as a result of a kidney disorder. In addition, the term can be generally used to refer to any portion of such gene or protein that can identify or correlate with the full-length gene or protein, for example, in an assay or other method of the invention.

Biomarker expression can also be identified by detection of biomarker translation (i.e., detection of biomarker protein in a sample). Methods suitable for the detection of biomarker protein include any suitable method for detecting and/or measuring proteins from a cell or cell extract. Such methods include, but are not limited to, immunoblot (e.g., Western blot), enzyme-linked immunosorbent assay (ELISA), radioimmunoassay (RIA), immunoprecipitation, immunohistochemistry and immunofluorescence. Particularly preferred methods for detection of proteins include any single-cell assay, including immunohistochemistry and immunofluorescence assays. Such methods are well known in the art. Furthermore, antibodies against certain of the biomarkers described herein are known in the art and are described in the public literature, and methods for their preparation are well known to the skilled worker.

The term "differential expression" or "differentially expressed" means increased or unregulated gene expression or means decreased or downregulated gene expression as detected by the absence, presence, or at least two-fold, or at least a 2.0, 1.9, 1.8, 1.7, 1.6, 1.5, 1.4, 1.3, 1.2, 1.1 or 1.0-fold change in the amount of transcribed messenger RNA or translated protein in a sample.

The term "fold" when used as a measure of differential gene expression means an amount of gene expression in a canine that is a multiple or a fraction of gene expression compared to the amount of gene expression against a control value. For example, a gene that is expressed 2 times as much in the animal as compared to the control value has a 2-fold differential gene expression and a gene that is expressed one-third as much in the animal as compared to the control value also has a 2-fold differential gene expression.

The term "fragment" means (1) an oligonucleotide or polynucleotide sequence that is a portion of a complete sequence and that has the same or similar activity for a particular use as the complete polynucleotide sequence or (2) a peptide or polypeptide sequence that is a portion of a complete sequence and that has the same or similar activity for a particular use as the complete polypeptide sequence. Such fragments can comprise any number of nucleotides or amino acids deemed suitable for a particular use. Generally, oligonucleotide or polynucleotide fragments contain at least about 10, 50, 100, or 1000 nucleotides and polypeptide fragments contain at least about 4, 10, 20, or 50 consecutive amino acids from the complete sequence. The term encompasses polynucleotides and polypeptides variants of the fragments. A polynucleotide, for example, can be broken up, or fragmented into, a plurality of segments.

Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

The term "gene" or "genes" means a complete or partial segment of DNA involved in producing a polypeptide, including regions preceding and following the coding region (leader and trailer) and intervening sequences (introns) between individual coding segments (exons). The term encompasses any DNA sequence that hybridizes to the complement of gene coding sequences.

The term "homolog" means (1) a polynucleotide, including polynucleotides from the same or different animal species, having greater than 30%, 50%, 70%, 90%, 91%, 92%, 93%, 94%, 95%, 96%, 97%, 98% or 99% sequence similarity to a polynucleotide and having the same or substantially the same properties and performing the same or substantially the same function as the complete polynucleotide, or having the capability of specifically hybridizing to a polynucleotide under stringent conditions or (2) a polypeptide, including polypeptides from the same or different animal species, having greater than 30%, 50%, 70%, 90%, 91%, 92%, 93%, 94%, 95%, 96%, 97%, 98% or 99% sequence similarity to a polypeptide identified by the expression of polynucleotides and having the same or substantially the same properties and performing the same or substantially the same function as the complete polypeptide, or having the capability of specifically binding to a polypeptide identified by the expression of polynucleotides. Sequence similarity of two polypeptide sequences or of two polynucleotide sequences is determined using methods known to skilled artisans, e.g., the algorithm of Karlin and Altschul (Proc. Natl. Acad. Sci. USA 87:2264-2268 (1990)). Such an algorithm is incorporated into the NBLAST and XBLAST programs of Altschul et al. (J. Mol. Biol. 215:403-410 (1990)). To obtain gapped alignments for comparison purposes, Gapped Blast can be utilized as described in Altschul et al. (Nucl. Acids Res. 25: 3389-3402 (1997)). When utilizing BLAST and Gapped BLAST programs, the default parameters of the respective programs (e.g., XBLAST and NBLAST) are used. See http://www.ncbi.nlm.nih.gov.

The term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid." The proportion of the population of polynucleotides that forms stable hybrids is referred to herein as the "degree of hybridization".

Hybridization reactions can be performed in absolute or differential hybridization formats. In the absolute hybridization format, polynucleotides derived from one sample are hybridized to the probes in a nucleic acid array. Signals detected after the formation of hybridization complexes correlate to the polynucleotide levels in the sample. In the differential hybridization format, polynucleotides derived from two samples are labeled with different labeling moieties. A mixture of these differently labeled polynucleotides is added to a nucleic acid array. The nucleic acid array is then examined under conditions in which the emissions from the two different labels are individually detectable. In one embodiment, the fluorophores Cy3 and Cy5 (Amersham Pharmacia Biotech, Piscataway, N.J.) are used as the labeling moieties for the differential hybridization format.

Signals gathered from nucleic acid arrays can be analyzed using commercially available software, such as those provided by Affymetrix or Agilent Technologies. Controls, such as for scan sensitivity, probe labeling and cDNA or cRNA quantization, are preferably included in the hybridization experiments. Hybridization signals can be scaled or normalized before being subject to further analysis. For instance, hybridization signals for each individual probe can be normalized to take into account variations in hybridization intensities when more than one array is used under similar test conditions. Hybridization signals can also be normalized using the intensities derived from internal normalization controls contained on each array. In addition, genes with relatively consistent expression levels across the samples can be used to normalize the expression levels of other genes. In one embodiment, probes for certain maintenance genes are included in a nucleic acid array of the present invention. These genes are chosen because they show stable levels of expression across a diverse set of tissues. Hybridization signals can be normalized and/or scaled based on the expression levels of these maintenance genes.

The term "hybridization complex" means a complex that is formed between sample polynucleotides when the purines of one polynucleotide hydrogen bond with the pyrimidines of the complementary polynucleotide, e.g., 5'-A-G-T-C-3' base pairs with 3'-T-C-A-G-5'. The degree of complementarily and the use of nucleotide analogs affect the efficiency and stringency of hybridization reactions.

The term "hybridization probes" includes nucleic acids (such as oligonucleotides) capable of binding in a base-specific manner to a complementary strand of nucleic acid.

The term "kidney disease" or "kidney disorder" or analogously "renal disease" or "renal disorder" is intended to cover an acute or chronic abnormal loss of kidney function, such as renal failure, reduced glomerular filtration rate and glomerulonephritis. Glomerulonephritis may take the form of membranous glomerulonephritis which involves thickening of the glomerular basement membrane. Alternatively, glomerulonephritis may take the form of proliferative or mesangioproliferative glomerulonephritis, which is characterized by proliferation of cells in the mesangial matrix. In addition, glomerulonephritis may take the form of membranoproliferative glomerulonephritis which involves a combination of the foregoing changes. Glomerulosclerosis is a severe form of glomerulonephritis. Kidney disease or kidney disorders also include nephritis, nephropathy, hyperfiltration, mild microalbuminuria, clinical albuminuria, advanced clinical nephropathy, chronic renal insufficiency, injuries to renal papilla, tubular necrosis and diabetic nephropathy, all as differentially diagnosed by veterinarians of ordinary skill in the art. The term is not intended to encompass polycystic kidney disease of genetic origin.

The term "polynucleotide" or "oligonucleotide" means a polymer of nucleotides. The term encompasses DNA and RNA (including cDNA and mRNA) molecules, either single or double stranded and, if single stranded, its complementary sequence in either linear or circular form. The term also encompasses fragments, variants, homologs, and alleles, as appropriate for the sequences that have the same or substantially the same properties and perform the same or substantially the same function as the original sequence. The sequences may be fully complementary (no mismatches) when aligned or may have up to about a 30% sequence mismatch. Preferably, for polynucleotides, the chain contains from about 50 to 10,000 nucleotides, more preferably from about 150 to 3,500 nucleotides. Preferably, for oligonucleotides, the chain contains from about 2 to 100 nucleotides, more preferably from about 6 to 30 nucleotides. The exact size of a polynucleotide or oligonucleotide will depend on various factors and on the particular application and use of the polynucleotide or oligonucleotide. The term includes nucleotide polymers that are synthesized and that are isolated and purified from natural sources. The term "polynucleotide" is inclusive of "oligonucleotide."

The term "polypeptide," "peptide," or "protein" means a polymer of amino acids. The term encompasses naturally occurring and non-naturally occurring (synthetic) polymers and polymers in which artificial chemical mimetics are substituted for one or more amino acids. The term also encompasses fragments, variants, and homologs that have the same or substantially the same properties and perforin the same or substantially the same function as the original sequence. The term encompass polymers of any length, preferably polymers containing from about 2 to 1000 amino acids, more preferably from about 5 to 500 amino acids. The term includes amino acid polymers that are synthesized and that are isolated and purified from natural sources.

The term "probe" means (1) an oligonucleotide or polynucleotide, either RNA or DNA, whether occurring naturally as in a purified restriction enzyme digest or produced synthetically, that is capable of annealing with or specifically hybridizing to a polynucleotide with sequences complementary to the probe or (2) a peptide or polypeptide capable of specifically binding a particular protein or protein fragment to the substantial exclusion of other proteins or protein fragments. An oligonucleotide or polynucleotide probe may be either single or double stranded. The exact length of the probe will depend upon many factors, including temperature, source, and use. For example, for diagnostic applications, depending on the complexity of the target sequence, an oligonucleotide probe typically contains about 10 to 100, 15 to 50, or 15 to 25 nucleotides. In certain diagnostic applications, a polynucleotide probe contains about 100-1000, 300-600, nucleotides, preferably about 300 nucleotides. The probes herein are selected to be "substantially" complementary to different strands of a particular target sequence. This means that the probes must be sufficiently complementary to specifically hybridize or anneal with their respective target sequences under a set of predetermined conditions. Therefore, the probe sequence need not reflect the exact complementary sequence of the target. For example, a noncomplementary nucleotide fragment may be attached to the 5' or 3' end of the probe, with the remainder of the probe sequence being complementary to the target sequence. Alternatively, noncomplementary bases or longer sequences can be interspersed into the probe provided that the probe sequence has sufficient complementarity with the sequence of the target polynucleotide to specifically anneal to the target polynucleotide. A peptide or polypeptide probe may be any molecule to which the protein or peptide specifically binds, including DNA (for DNA binding proteins), antibodies, cell membrane receptors, peptides, cofactors, lectins, sugars, polysaccharides, cells, cell membranes, organelles and organellar membranes.

The terms "sample" and "specimen" mean any animal tissue or fluid containing, e.g., polynucleotides, polypeptides, antibodies, metabolites, and the like, including cells and other tissue containing DNA and RNA. Examples include: blood, cartilage, connective, epithelial, lymphoid, muscle, nervous, sputum, and the like. A sample may be solid or liquid and may be DNA, RNA, cDNA, bodily fluids such as blood or urine, cells, cell preparations or soluble fractions or media aliquots thereof, chromosomes, organelles, and the like.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof. A single package may be containers of individual food compositions physically associated such that they are considered a unit for manufacture, distribution, sale, or use.

The "specifically bind" means a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

The term "specifically hybridize" means an association between two single stranded polynucleotides of sufficiently complementary sequence to permit such hybridization under predetermined conditions generally used in the art (sometimes termed "substantially complementary"). For example, the term may refer to hybridization of a polynucleotide probe with a substantially complementary sequence contained within a single stranded DNA or RNA molecule according to an aspect of the invention, to the substantial exclusion of hybridization of the polynucleotide probe with single stranded polynucleotides of non-complementary sequence.

The term "stringent conditions" means (1) hybridization in 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C., (2) hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C.; with washes at 42° C. in 0.2×SSC and 0.1% SDS or washes with 0.015 M NaCl, 0.0015 M sodium citrate, 0.1% $Na_2SO_4$ at 50° C. or similar procedures employing similar low ionic strength and high temperature washing agents and similar denaturing agents.

The term "substance" means an element, compound, molecule, or a mixture thereof or any other material that could potentially be useful for diagnosing, prognosing, or modulating the onset or severity of a kidney disorder in an animal, including any drug, chemical entity, or biologic entity.

The term "useful variations" means (1) for a polynucleotide, the complements of the polynucleotide; the homologs of the polynucleotide and its complements; the variants of the polynucleotide, its complements, and its homologs; and the fragments of the polynucleotide, its complements, its homologs, and its variants and (2) for a polypeptide, the homologs of the polypeptide; the variants of the polypeptide and its homologs; and the fragments of the polynucleotide, its homologs, and its variants.

The term "variant" means (1) a polynucleotide sequence containing any substitution, variation, modification, replacement, deletion, or addition of one or more nucleotides from or to a polynucleotide sequence and that has the same or substantially the same properties and performs the same or substantially the same function as the original sequence and (2) a polypeptide sequence containing any substitution, variation, modification, replacement, deletion, or addition of one or more amino acids from or to a polypeptide sequence and that has the same or substantially the same properties and performs the same or substantially the same function as the original sequence. The term therefore includes single nucleotide polymorphisms (SNPs) and allelic variants and includes conservative and non-conservative amino acid substitutions in polypeptides. The term also encompasses chemical derivatization of a polynucleotide or polypeptide and substitution of nucleotides or amino acids with nucleotides or amino acids that do not occur naturally, as appropriate.

The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact a caregiver or instructor to obtain instructions on how to use the kit.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural references unless the context clearly dictates otherwise, e.g., reference to "a variant"

includes a plurality of variants. Further, defined terms include variations of the terms used in the proper grammatical context, e.g., the term "specifically binds" includes "specific binding" and other forms of the term. Similarly, the words "comprise," "comprises," and "comprising" are to be interpreted inclusively rather than exclusively.

Unless defined otherwise, all technical and scientific twos and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, is relevant prior art for the present invention and the right to challenge the accuracy and pertinence of such patents, patent applications, publications, and other references is specifically reserved.

In one embodiment, the present invention encompasses one or more genes or gene segments ("genes" as defined herein) that are differentially expressed in abnormal animals compared to a control value obtained from one or more normal animals. The invention is based upon the discovery of polynucleotides that are differentially expressed in abnormal animals compared to normal animals. The genes were identified by comparing the expression of genes in tissue samples taken from animals diagnosed as abnormal with genes in tissue samples from animals diagnosed as normal using Affymetrix GeneChip® technology.

The polynucleotides and genes are identified by measuring differences in gene expression from tissue samples taken from canines diagnosed as abnormal and having a kidney disorder against a control value, wherein the control value is obtained from a sample from one or more normal animals. Changes in gene expression can be determined by any method known to skilled artisans. Generally, changes in gene expression are determined by measuring transcription (determining the amount of mRNA produced by a gene) or measuring translation (determining the amount of protein produced by a gene). The amount of RNA or protein produced by a gene can be determined using any method known to skilled artisans for quantifying polynucleotides and proteins.

Generally, mRNA expression is determined using polymerase chain reaction (PCR) (including, without limitation, reverse transcription-PCR (RT-PCR) and quantitative real-time PCR (qPCR)), short or long oligonucleotide arrays, cDNA arrays, EST sequencing, Northern blotting, SAGE, MPSS, MS, bead arrays and other hybridization methods. The RNA measured is typically in the form of mRNA or reverse transcribed mRNA.

Protein or polypeptide expression is determined using various colormetric and spectroscopic assays and methods such as quantitative Western blots, ELISA, 2D-gels, gas or liquid chromatography, mass-spec, the lowry assay, the biuret assay, fluorescence assays, turbidimetric methods, the bicinchoninic assay, protein chip technology, infrared absorbance, ninhydrin, the Bradford assay, and ultraviolet absorbance.

In a preferred method, changes in gene expression are determined using Affymetrix Canine-1 and Canine-2 gene chips available from Affymetrix, Inc. and the instructions for using such chips to determine gene expression. Gene chips allow a large-scale study of biological processes and the measurement of activity within a cell at a certain point in time. Microarray analysis permits one to account for differences in phenotypes on a large-scale genetic basis. Actual measurement of gene expression products is a more accurate indicator of gene function than determining sequences per se. Microarray analysis is based upon quantifying the concentration of a gene's mRNA transcript in a cell at a given time. DNA is immobilized on a medium and labeled target mRNA is hybridized with probes on the array. Binding of the labeled mRNA to the probes is measured by laser analysis. The measurement is a count of photons emitted. The entire chip is scanned and digitally imaged. The image is processed to locate probes and to assign intensity measurements to each probe. In this manner up- and down-regulated genes may be determined. The analysis enables the skilled person to find groups of genes with similar expression profiles and to determine tissues with similar expression profiles. In this manner, genes that explain the observed differences in tissue samples can be identified.

Affymetrix Gene Chips typically employ probes of 25 bp and probe sets of 11 to 20 probes corresponding to a particular gene or EST. The chip is constructed with a perfect match and mismatch probe of 25 bp each, the former being perfectly complementary to a specific region of a gene and the latter having the $13^{th}$ by substituted to make a mismatch. A probe summarization algorithm is used to determine background correction, normalization and probe summarization, which is the conversion of probe values to probeset expression values. RMA is one of the algorithms that may be used for this purpose. The algorithm performs the last two steps of analysis, normalization and summarization of probe-level intensity measurements. The perfect match values are, therefore, background corrected, normalized and summarized into a set of expression measurements.

The raw data is analyzed using GeneSpring version 7.0 (GS) software (Agilent Corporation) and validated using the R-Bioconductor (RB) freeware. Both software packages are used to compute probe intensities from the CEL files generated by the Affymetrix Instrument. The Present/Absent/Marginal calls per probe and P-values are computed using the R-Bioconductor and GeneSpring software separately.

Generally, differential gene expression is determined by measuring the expression of at least one gene. Preferably, the expression of two or more differentially expressed genes is measured to provide a gene expression pattern or gene expression profile. More preferably, the expression of a plurality of differentially expressed genes is measured to provide additional information for a more significant gene expression pattern or profile.

The present invention provides a plurality of markers that together or alone are or can be used as markers of renal disease. In especially useful embodiments of the invention, a plurality of these markers can be selected and their mRNA expression may be measured simultaneously to provide expression profiles for use in various aspects of the inventions described in this application. In a preferred embodiment of the present methods and compositions, at least 2, 3, 4, 5, 6, 7, 8, 9, 10, or 11 markers are selected among lumican (LUM); collagen alpha 1 (III) chain, variant 12 (COL3A1); decorin (DCN); secreted frizzled-related protein 2 (sFRP2); matrilin-2 (Matn2); retinol binding protein 4 (rbp4); MMP-9; clusterin (CLU); transferrin (TF), Apo-C-1 (ApoC1); and inhibin beta A (INHBA) and can be used for determination of gene expression profiles employed in the practice of the methods of the invention. Each marker can be particularly linked to certain aspects of kidney disease.

In another embodiment of the invention, the level of gene expression can be alternatively determined by detecting the protein corresponding to the gene expression product. Secreted proteins of the denominated genes are preferred.

In another aspect, the invention provides a device suitable for detecting the expression of a plurality of genes differentially expressed in abnormal animals compared to a control values. The device comprises a substrate having a plurality of the oligonucleotide or polynucleotide probes of the present invention affixed to the substrate at known locations. The device is essentially an immobilized version of the oligonucleotide or polynucleotide probes described herein. The device is useful for rapid and specific detection of genes and polynucleotides and their expression patterns and profiles. Typically, such probes are linked to a substrate or similar solid support and a sample containing one or more polynucleotides (e.g., a gene, a PCR product, a ligase chain reaction (LCR) product, a DNA sequence that has been synthesized using amplification techniques, or a mixture thereof) is exposed to the probes such that the sample polynucleotide(s) can hybridize to the probes. Either the probes, the sample polynucleotide(s), or both, are labeled, typically with a fluorophore or other tag such as streptavidin, and detected using methods known to skilled artisans. If the sample polynucleotide(s) is labeled, hybridization may be detected by detecting bound fluorescence. If the probes are labeled, hybridization is typically detected by label quenching. If both the probe and the sample polynucleotide(s) are labeled, hybridization is typically detected by monitoring a color shift resulting from proximity of the two bound labels. A variety of labeling strategies and labels are known to skilled artisans, particularly for fluorescent labels. Preferably, the probes are immobilized on substrates suitable for forming an array (known by several names including DNA microarray, gene chip, biochip, DNA chip, and gene array) comparable to those known in the art.

The polypeptide probes may be made according to conventional methods, e.g., using the nucleotide sequence data provided for polynucleotides of the present invention and methods known in the art. Such methods include, but are not limited to, isolating polypeptide directly from cells, isolating or synthesizing DNA or RNA encoding the polypeptides and using the DNA or RNA to produce recombinant products, synthesizing the polypeptides chemically from individual amino acids, and producing polypeptide fragments by chemical cleavage of existing polypeptides.

In another aspect, the invention provides a device suitable for detecting the expression of a plurality of genes differentially expressed in abnormal animals compared to a control value. The device comprises a substrate having a plurality of the peptide or polypeptide probes of the present invention affixed to the substrate at known locations. The device is essentially an immobilized version of the peptide or polypeptide probes described herein. The device is useful for the rapid and specific detection of proteins and their expression patterns. Typically, such probes are linked to a substrate and a sample containing one or more proteins is exposed to the probes such that the sample proteins can hybridize to the probes. In certain embodiments, the probes, the sample proteins, or both, are labeled and detected, typically with a fluorophore or other agent known to skilled artisans. Generally, the same methods and instrumentation used for reading polynucleotide microarrays is applicable to protein arrays. Preferably, the probes are immobilized on a substrate suitable for forming an array.

Methods for determining the amount or concentration of protein in a sample are known to skilled artisans. Such methods include radioimmunoassays, competitive-binding assays, Western blot analysis, and ELISA assays. For methods that use antibodies, polyclonal and monoclonal antibodies are suitable. Such antibodies may be immunologically specific for a protein, protein epitope, or protein fragment.

Some embodiments of the invention utilize antibodies for the detection and quantification of proteins produced by expression of the polynucleotides of the present invention. Although proteins may be detected by immunoprecipitation, affinity separation, Western blot analysis, protein arrays, and the like, a preferred method utilizes ELISA technology wherein the antibody is immobilized on a solid support and a target protein or peptide is exposed to the immobilized antibody. Either the probe, or the target, or both, can be labeled using known methods.

In some embodiments, expression patterns or profiles of a plurality of genes differentially expressed in abnormal animals are observed utilizing an array of probes for detecting polynucleotides or polypeptides. In one embodiment, arrays of oligonucleotide or polynucleotide probes may be utilized, whereas another embodiment may utilize arrays of antibodies or other proteins that specifically bind to the differentially expressed gene products of the present invention. Such arrays may be commercially available or they may be custom made using methods known to skilled artisans, e.g., in-situ synthesis on a solid support or attachment of pre-synthesized probes to a solid support via microprinting techniques. In various embodiments, arrays of polynucleotides or polypeptides probes are custom made to specifically detect transcripts or proteins produced by the differentially expressed genes of the present invention.

In one embodiment, arrays of polynucleotide or polypeptide probes are custom made to specifically detect transcripts or proteins produced by two or more polynucleotides or genes identified in Table 2. These probes are designed to detect genes associated with lipid and glucose metabolism pathways in animals. In another embodiment, arrays of polynucleotide or polypeptide probes are custom made to specifically detect transcripts or proteins produced by two or more polynucleotides or genes identified in Tables 3-5. These probes are designed to detect genes that are particularly relevant to abnormal canines compared to normal canines.

These probes are exposed to a sample to form hybridization complexes that are detected and compared with those of a standard. The differences between the hybridization complexes from the sample and standard indicate differential expression of polynucleotides and therefore genes differentially expressed in abnormal canines compared to a control value in the sample. In a preferred embodiment, probes are made to specifically detect polynucleotides or fragments thereof produced by one or more of the genes or gene fragments identified by the present invention. Methods for detecting hybridization complexes are known to skilled artisans.

In another aspect, the invention provides a method for detecting the differential expression of genes differentially expressed in abnormal canines compared to normal canines in a sample. The method comprises (a) reacting a combination comprising a plurality of polypeptide probes with proteins in the sample under conditions that allow specific binding between the probes and the proteins to occur, wherein the proteins bound by the probes are differentially expressed in an abnormal canine compared to a normal canine; (b) optionally, reacting a combination comprising a plurality of polypeptide probes with proteins in a standard under conditions that allow specific binding between the probes and the proteins to occur, wherein the proteins bound by the probes are differentially expressed in an abnormal canine compared to a normal canine; (c) detecting specific binding in the sample and, optionally, the standard from step (b); and (d) comparing the specific binding in the sample with that of a standard, wherein differences between the specific binding in the standard and the sample indicate differential expression of genes differentially expressed in abnormal canines compared to normal canines in the sample.

These probes are exposed to a sample to form specific binding that is detected and compared with those of a standard. The differences between the specific binding from the sample and standard indicate differential expression of proteins and therefore genes differentially expressed in abnormal canines compared to normal canines, particularly abnormal-associated genes, in the sample. In a preferred embodiment, probes are made to specifically detect proteins or fragments thereof produced by one or more of the genes or gene fragments identified by the present invention.

In one embodiment, the method further comprises exposing the canine or sample to a test substance before reacting the polypeptides with the proteins. Then, the comparison is indicative of whether the test substance altered the expression of genes differentially expressed in abnormal canines compared to normal canines, particularly abnormal-associated genes, in the sample.

Example 1

Classification of Canines with Chronic Kidney Disease According to the Guidelines of the International Renal Interest Society In the Examples that follow, canines exhibiting clinical signs of chronic kidney disease were tested versus animals not exhibiting signs or symptoms of chronic kidney disease. Pathological diagnoses of chronic kidney disease were made based on the criteria set forth in Tables 1 and 2 below and in accordance with the guidelines of the International Renal Interest Society (IRIS).

Staging of chronic kidney disease (CKD) is undertaken following the diagnosis of CKD in order to facilitate appropriate treatment and monitoring of the subject animal. Staging is based initially on fasting plasma creatinine, assessed on at least two occasions in the stable animal. Canines demonstrating normal renal function and no clinical signs or symptoms of CKD were grouped as non-disease canines. Stage 1 in canines corresponds to prior classifications of early renal disease with no biochemical evidence of CKD to renal insufficiency, where no azotemia is detected, but where glomerular filtration rate (GFR) may be reduced and there may be a poor concentrating ability of the kidneys. Stage 2 corresponds to the prior classification of early renal failure. In Stage 2, mild azotemia is noted. Stage 3 corresponds to prior classification of uremic renal failure, where moderate azotemia is detected. Systemic signs of uremic renal failure may be present such as bone pain, uremic gastritis, anemia and metabolic acidosis. Stage 4 corresponds to end-stage renal failure, which is characterized by severe azotemia and increasing systemic clinical signs of uremic crisis.

Table 1 identifies the five categories of canines studied, respectively. A total of 42 dogs diagnosed as not having CKD were studied. A total of 14 Stage 1 canines exhibited minimal glomerulonephritis (GN). The number of dogs studied exhibiting advanced stages of CKD were: Stage 2 mild GN=24; Stage 3 moderate GN=8 and Stage 4 marked GN=13. Plasma creatinine levels for each of the groups of dogs are shown in Table 2 as mean and median plasma creatinine levels for each group of dogs.

TABLE 1

Staging for Canines

| IRIS CKD Staging | Plasma Creatinine range mg/dl |
|---|---|
| Non-Disease | <1.4 with no firm evidence of disease |
| Stage 1 | <1.4 (<125 µmol/l) with evidence of disease. Non-azotemic. Some other renal abnormality present (e.g. inadequate concentrating ability without identifiable non-renal cause; abnormal renal palpation and/or renal imagining findings; proteinuria of renal origin; abnormal renal biopsy |
| Stage 2 | 1.4 to 2.0 (125-179 µmol/l) Mild renal azotemia. Clinical signs usual mild or absent. |
| Stage 3 | 2.1 to 5.0 (180-439 µmol/l) Moderate renal azotemia. Many clinical signs may be present. |
| Stage 4 | >5.0 (>440 µmol/l) Sever renal azotemia. Many extra-renal clinical signs present. |

TABLE 2

Creatinine Levels

| Pathological Diagnosis | Mean Plasma Creatinine mg/dl | Median Plasma Creatinine mg/dl |
|---|---|---|
| Non-Disease (n = 42) | 0.8 | 0.7 |
| Minimal GN (n = 14) | 0.7 | 0.7 |
| Mild GN (n = 24) | 0.9 | 0.7 |
| Moderate GN (n = 8) | 1.5 | 1.5 |
| Marked GN (n = 13) | 6.7 | 6.2 |

Example 2

Candidate Selection Criteria

The raw data in the following examples was analyzed using GeneSpring version 7.0 (GS) software (Agilent Corporation) and validated using the R-Bioconductor (RB) freeware. Both software packages are used to compute probe intensities from the CEL files generated by the Affymetrix Instrument. The Present/Absent/Marginal calls per probe and P-values are computed using the R-Bioconductor and GeneSpring software separately.

The gene expression data is determined to be either "up" or "down"-regulated for any given analysis. The decision on whether a gene is "up" or "down" is based on the fold change, which is calculated as treatment intensity/control intensity for each individual probe. The fold change is considered down-regulated if its value is <½ and is up-regulated if it is >2.0. Also, a probe is considered significant for further scrutiny if it is called as present in only one of the conditions being compared (treatment or control) and is "absent" or "marginal" in the other and the fold change is significant according to the software used.

Example 3

RNA Isolation Procedures

Materials and Methods. The following general procedures may be used to isolate RNA from tissue samples of dogs and cats for gene expression profiling utilizing gene chips as further described in the Examples of this specification. It will be apparent to a person of ordinary skill in the art that these procedures or modifications thereof, as recognized within the art, can be applied to isolate RNA from tissue or body fluid samples for further gene expression analysis using a variety of analytical procedures available to a person of ordinary skill in the art, in particular microarray technologies.

Isolation of Ribonucleic Acid (RNA) from Tissue.

Tissue samples may be collected, frozen in liquid nitrogen, thawed and then, ground in a mortal and pestle, homogenized and transferred to a 50 ml conical flask. The homogenized tissue sample is then processed using a TRIzol® RNA extraction method according to the manufacturer's instructions (Invitrogen) to produce good quality RNA which is then subjected to further genomic analysis.

Materials: Ice, liquid nitrogen, frozen canine tissue, TRIzol® lysis reagent, chloroform minimum 99%, isopropyl alcohol, 70% ethanol (prepared with ethanol, absolute and deionized, RNase-free water), RNase Zap®, deionized water, RNA Storage Solution®, from Ambion.

Equipment: Ultra-Turrax T25 Power Homogenizer, Beckman Coulter Allegra 25R Centrifuge, Eppendorf Centrifuge, forceps, scalpel, hard cutting surface, i.e. cutting board, 1.5 mL DNase and RNase free/sterile microcentrifuge tubes, 50 mL DNase and RNase free/sterile disposable polypropylene tubes, P1000, P200, P20, P10 and P2 Rainin Pipetman pipettes, filter pipette tips for P1000, P200, P20, P10 and P2 pipettes, DNase and RNase free/sterile, and lint free wipes.

Preparations: Prepare 50 mL polypropylene tubes with 4 mL TRIzol® (one tube for each tissue selected for RNA isolation).

Tissue Homogenization: Fill a container capable of holding liquid nitrogen with 3-4 scoops of liquid nitrogen. Place a piece of frozen tissue immediately into the aforementioned container (the tissue should be about the size of a pea) and place the tissue into the appropriate labeled 50 mL polypropylene tube (that already contains 4 mL TRIzol®). Immediately begin homogenization using the Ultra-Turrax T25 Power Homogenizer. Homogenize on the highest setting (6) for 10-15 seconds. Cool the sample on ice for another 10-15 seconds and then repeat. Continue until the tissue is fully homogenized and the solution is cloudy. Upon complete homogenization, cap the 50 mL tube and return to the ice. Incubate the homogenized tissues at room temperature for 5 minutes before proceeding with the isolation procedure.

Example 4

RNA Preparation Procedures

RNA Isolation: The procedures given in the Invitrogen instructions provided with the TRIzol® reagent are generally followed. Separate the homogenized sample into four 1 mL aliquots in four 1.5 mL microcentrifuge tubes. Add 200 uL of chloroform to each 1 mL aliquot. Cap the tubes, vortex for 15 seconds and then shake up and down. The result should be a pink milky liquid. Incubate the tubes at room temperature for 2-3 minutes. Centrifuge the tubes for 15 minutes at 14,000 rpm and 4° C. Transfer the aqueous phase (top layer) to a sterile 1.5 mL microcentrifuge tube. The typical volume of the aqueous phase which should be transferred to the new tube is about 500 uL. Be sure not to transfer any of the intermediate or lower phase. Precipitate the RNA from solution by adding 500 uL of Isopropyl Alcohol to each microcentrifuge tube containing the aqueous layer. Shake the tubes up and down for at least 20 seconds. Incubate the samples at room temperature for 10 minutes. Centrifuge the samples for 10 minutes, 14,000 rpm at 4° C. Remove the supernatant carefully by aspirating off the liquid being sure not to lose the pellet. Add 1 mL of 70% ethanol to wash the pellet. Dislodge the pellet by flicking the tube (or tapping the tube on the bench top) and shake to mix. Centrifuge for 5 minutes, 8,200 rpm at 4° C. Remove the supernatant carefully by aspirating off the liquid being sure not to lose the pellet. Use a lint free wipe to carefully soak up excess ethanol to make sure the pellet is dry. Resuspend each pellet into 30 uL of RNA Storage Solution. Mix gently by pipetting until the RNA goes back into solution and then store at −80° C. It may be necessary to vortex the sample for a few seconds at a low speed to facilitate the resuspension of the RNA. If this is necessary, spin down the samples, using the microcentrifuge, prior to freezing.

RNA Cleaning: The procedures given in the RNeasy® Mini Handbook are followed.

RNA Isolation from Cells Cultured in OptiCell Chambers Using the RNeasy Mini Kit. Cells cultured from mammalian cell lines are used to isolate good quality RNA which is then used for future downstream genomic analysis. All work related to the culturing of the cells is to be done under strict aseptic conditions.

Reagents: 10×PBS, deionized $H_2O$, absolute ethanol, RNA Storage Solution, β-Mercaptoethanol, RNase Zap®, Buffer RLT, and Buffer RW1 and Buffer RPE (provided in the RNeasy Mini Kit).

Equipment/Materials: RNeasy Mini Kit, QIAshredder spin columns, OptiCell knife, 20 mL sterile syringe, OptiCell tips, Cell scraper, P1000 Pipetman pipette, Rainin, P200 Pipetman pipette, Rainin, 100-100 uL filtered pipette tips, 1-200 uL filtered pipette tips, sterile transfer pipettes, 55 mL sterile solution basin, 1.5 mL sterile microcentrifuge tubes, and Eppendorf Microcentrifuge.

Solutions: Buffer RLT (stock provided in RNeasy Mini Kit); —Add 100 uL of β-Mercaptoethanol per 10 mL of Buffer RLT prior to beginning protocol. 70% Ethanol: Make 50 mL of 70% ethanol by adding 35 mL absolute ethanol to 15 mL deionized, RNase-free water. 1×PBS: RNase-free water. Filter the solution using a 0.22 um filter.

Procedure: Removing Cells from the OptiCell Chamber (proceed one OptiCell at a time). Check the cells under a microscope to ensure that the cells are alive before isolating RNA. Remove and discard the cell culture medium. Using the OptiCell knife, cut away the top membrane exposing the cells on the lower membrane. Wash the membrane to which the cells are attached three times with 1×PBS. Pipette 600 uL of the Buffer RLT solution (containing β-Mercaptoethanol) onto the center of the membrane to which the cells are attached. Using the cell scraper, gently spread the Buffer RLT over the entire surface of the membrane, and then collect the liquid in one corner. Pipette off the entire volume of Buffer RLT and place into a QIAshredder spin column.

RNA Isolation: Centrifuge the QIAshredder spin columns at 14,000 rpm for 2 minutes. Discard the spin column but keep the collection tube and its contents. Add 600 uL of 70% ethanol to the collection tube and mix well by pipetting (the total volume now=1.2 mL). Transfer 600 uL of the cell lysate to an RNeasy mini column and centrifuge for 15 seconds at 14,000 rpm. Discard the flow through but keep the collection tube and the spin column. Transfer the remaining volume of cell lysate (~600 uL) to the spin column and repeat the centrifugation. Discard the flow through but keep the collection tube and the spin column. Add 700 uL Buffer RW1 to the spin column. Centrifuge for 15 seconds at 14,000 rpm to wash the column. Discard the flow through and the collection tube. Transfer the spin column to a new 2 mL collection tube and add 500 uL Buffer RPE to the column. Centrifuge for 15 seconds at 14,000 rpm. Discard the flow through, keep the collection tube/column. Add another 500 uL Buffer RPE to the column. Centrifuge for 2 minutes at 14,000 rpm. Transfer the spin column to a 1.5 mL collection tube. Add 30 uL of RNA Storage Solution directly to the silica gel membrane and centrifuge for 1 minute at 14,000 rpm to elute the RNA. Store the final RNA at −70° C.

RNA 6000 Nano Assay.

Using the Agilent 2100 Bioanalyzer and the RNA 6000 Nano Assay, analyze RNA isolated from cultured mammalian cells, lymphocytes or tissues for quality.

Reagents: RNA 6000 Nano gel matrix, RNA 6000 Nano dye concentrate, RNA 6000 Nano Marker, (all of the above reagents are contained in the RNA 6000 Nano Assay kit, Agilent), RNA 6000 ladder, RNase Zap, and RNase-free water, from Ambion.

Equipment/Other Materials: Agilent Chip Priming Station, Agilent, RNA 6000 chip, Agilent, electrode cleaners, P2, P10, P200, and P1000 Rainin Pipetman pipettes, sterile, DNase/RNase free filtered pipette tips, 1.5 mL microcentrifuge tubes, sterile, vortex, IKA vortex mixer, microcentrifuge, and heating block.

Procedure: The procedure is given in the Reagent Kit Guide, RNA 6000 Nano Assay, Edition November 2003, by Agilent Technologies. The procedures are followed as given in the Guide, with the following modifications: Preparing the Gel, pg. 17—rather than separating the filtered gel into aliquots of 65 uL each, keep the stock filtered gel in the original microcentrifuge tube and aliquot the 65 uL as needed. Loading the RNA 6000 Nano Marker, pg. 22—add 1 uL of RNase-free water (instead of RNA 6000 Nano Marker) to each sample well that will not contain sample. Not only will this conserve the amount of Marker used but also serves as a negative control to see that none of the reagents are contaminated, including the RNase-free water. Loading the Ladder and Samples, pg. 23—heat denature the samples and RNA 6000 Ladder for an additional 30 seconds (total of 2.5 minutes) at 71° C. Starting the Chip Run, pg. 26—choose the "Eukaryote Total RNA Nano" option from the assay menu.

Example 5

Affymetrix GeneChip Expression Analysis

Gene expression is analyzed using Affymetrix Canine 1 and Canine 2 GeneChip® Arrays which are commercially available from Affymetrix, Inc., Santa Clara, Calif. 95051.

Total RNA is reverse transcribed into cDNA. The cDNA is used to generate cRNA which is fragmented and used as probes for GeneChip hybridization. The gene chip is washed and the hybridization signal is measured with an Affymetrix laser scanner. The hybridization data is then validated and normalized for further analysis in accordance with instructions from the manufacturer.

Materials: Affymetrix provides most of the reagents and kit. Other reagents listed in the Affymetrix Manual but not supplied in the kit may be obtained separately (refer to GeneChip Expression Analysis Technical Manual (701021 Rev.4) for details), RNase Zap® and deionized water.

Equipment: Eppendorf microcentrifuge, 1.5 mL DNase and RNase free/sterile microcentrifuge tubes, 50 mL DNase and RNase free/sterile disposable polypropylene tubes, P1000, P200, P20, P10 and P2 Rainin Pipetman pipettes, Filter pipette tips for P1000, P200, P20, P10 and P2 pipettes, DNase and RNase free/sterile, and Peltier Thermal Cycler PTC-200.

Procedure: follow all procedures exactly as described in GeneChip Expression Analysis Technical Manual (Affymetrix Copyright 1999-2003). Use 5 microgram of total RNA for the first strand cDNA synthesis. Use either Peltier Thermal Cycler PTC-200 or heat block for temperature control on reactions and probe denaturing. The quality control is performed using RNA NanoDrop chips with BioAnalyer 2100. Use 100 Format (Midi Array) for the canine genechip.

Example 6

Gene Expression in Dogs with Chronic Kidney Disease

Studies were conducted in accordance with the previous Examples 1-5 using dogs having various stages of chronic kidney disease to determine the underlying gene expression differences between dogs with normal renal function and dogs having minimal, mild, moderate and marked glomerulonephritis corresponding to Stages 1 through 4 as presented on Table 1. Procedures as described in the Examples of this specification were used to prepare tissue and bodily fluid samples from 42 dogs having normal renal function, 14 dogs having minimal glomerulonephritis, 24 dogs having mild glomerulonephritis, 8 dogs having moderate glomerulonephritis and 13 dogs having marked glomerulonephritis, as determined by plasma creatinine levels presented in Table 2 and by clinical observation.

Based on gene expression data comparing the dogs with normal renal function versus dogs having glomerulonephritis, as defined in the preceding examples, the five genes listed on Table 3 were identified as meeting the selection criteria of Example 2 as potential biomarkers of chronic kidney disorders in dogs. The genes include lumican (LUM); collagen alpha 1 (III) chain, variant 12 (COL3A1); Decorin (DCN); secreted frizzled-related protein 2 (SFRP2); and Matrilin-2 (Matn2). Analogous human synonyms and mRNA and protein accession numbers are listed on Table 3 for each gene. Each of the proteins is a secreted protein.

TABLE 3

List of Potential Biomarkers

| Gene | Symbol in Canine/Human | Human Synonyms | Canine Synonym | Gene Description | mRNA | Protein |
|---|---|---|---|---|---|---|
| Lumican | LUM | LDC; SLRR2D | | | XM_539716.2 | XP_539716.1 |
| Collagen alpha 1 (III) chain, variant 12 | COL3A1 | EDS4A; FLJ34534 | | | XM_858055.1 | XP_863148 |

TABLE 3-continued

List of Potential Biomarkers

| Gene | Symbol in Canine/Human | Human Synonyms | Canine Synonym | Gene Description | mRNA | Protein |
|---|---|---|---|---|---|---|
| Decorin | DCN | CSCD; DSPG2; PG40; PGII; PGS2; SLRR1B | | | NM_001003228.1 | NP_001003228.1 |
| SFRP2 | SFRP2 | FRP-2; SARP1; SDF-5 | | secreted frizzled-related protein 2 | NM_001002987.1 | NP_001002987.1 |
| Matrilin-2 | Matn2 | Crtm2; MGC102477; matrilin-2 | | matrilin 2 | XM_548552.2 | XP_548552.2 |

TABLE 4

List of Potential Biomarkers

| Gene | Symbol in Canine/Human | Human Synonyms | Canine Synonym | Gene Description | mRNA | Protein |
|---|---|---|---|---|---|---|
| Retinol Binding Protein 4 | Rbp4 | Rbp-4 | | retinol binding protein 4, plasma | XM_534969.2 | XP_534969.2 |
| MMP-9 | MMP9 | CLG4B; GELB; MMP-9 | | matrix metallopeptidase 9 (gelatinase B, 92 kDa gelatinase, 92 kDa type IV collagenase) | NM_001003219.1 | NP_001003219.1 |
| Clusterin | CLU | AAG4; APOJ; CLI; KUB1; MGC24903; SGP-2; SGP2; SP-40; TRPM-2; TRPM2 | GP80 | | NM_001003370.1 | NP_001003370.1 |

TABLE 5

List of Potential Biomarkers

| Gene | Symbol in Canine/Human | Human Synonyms | Canine Synonym | Gene Description | mRNA | Protein |
|---|---|---|---|---|---|---|
| Transferrin | TF | DKFZp781D0156; PRO1557; PRO2086 | | | XM_534268 | XP_534268 |
| Apo-C-I | APOC1 | | | apolipoprotein C-I | XM_533643 | XP_533643 |
| Inhibin beta A | INHBA | EDF; FRP | | | XM_540364 | XP_540364 |

What is claimed is:

1. A method of treating, ameliorating, or delaying the progression of a kidney disorder in a canine, comprising the steps of:
   (a) diagnosing the kidney disorder by measuring the level of expression of at least one biomarker in a biological sample from the canine, wherein the at least one biomarker is selected from secreted frizzle-related protein-2 (SFRP2); matrilin-2 (Matn2); lumican (LUM); retinol binding protein 4 (rbp4); transferrin (TF); Apo-C-1 (ApoC1); and inhibin beta A (INHBA), and wherein the test sample is a sample of solid kidney tissue or a bodily fluid;
   (b) identifying the canine as having a kidney disorder wherein differences in expression of one or more biomarkers in the sample relative to a control value for expression in a sample from a normal animal indicates the existence of a kidney disorder, and wherein the differences in expression are determined with a custom array consisting of two or more probes specific to the biomarkers selected from matrilin-2 (Matn2); lumican (LUM); retinol binding protein 4 (rbp4); transferrin (TF); Apo-C-1 (ApoC1); and inhibin beta A (INHBA); and
   (c) treating, ameliorating, or delaying the progression of the kidney disorder in the canine identified in step (b);
   wherein the kidney disorder is indicated by a significant difference in expression of one or more biomarkers relative to control expression values wherein a significant difference in the case of increased expression is an increase of at least twofold and in the case of decreased expression is a decrease of at least 50% and wherein one or more biomarkers is selected from: matrilin-2 (Matn2); lumican (LUM); retinol binding protein 4 (rbp4); transferrin (TF); Apo-C-1 (ApoC1); and inhibin beta A (INHBA), and
   wherein the canine has normal renal function, wherein normal renal function is determined by one or more of: glomular filtration rate, urine protein level, blood creatinine level, urine creatinine level, creatinine clearance and blood urea nitrogen.

2. The method of claim 1, wherein the differential expression of step (b) is determined with a panel of one or more antibodies that specifically bind to the at least one biomarker.

3. The method of claim 1, wherein the differential expression of step (b) is determined by immunoassay to detect the at least one biomarker.

4. The method of claim 3, wherein the immunoassay is selected from the group consisting of a competitive binding assay, a non-competitive binding assay, a radioimmunoassay, an enzyme linked immunosorbent assay (ELISA), a sandwich assay, a precipitin reaction, a gel diffusion immunodiffusion assay, an agglutination assay, a fluorescent immunoassay, chemiluminescence immunoassay, immunoPCR immunoassay, a protein A or protein G immunoassay, Northern blot analysis, Western blot analysis, bead-based multiplexed assay and an immunoelectrophoresis assay.

5. The method of claim 1, further comprising use of one or more conventional diagnostic measurement selected from the group consisting of: determining levels of albumin, determining levels of serum cystatin C, determining levels of blood creatinine, determining levels of urinary creatinine, determining levels of creatinine clearance, determining levels of urinary protein, determining levels of blood urea nitrogen and determining glomerular filtration rate.

* * * * *